(12) United States Patent
Ozaki

(10) Patent No.: US 11,999,988 B2
(45) Date of Patent: Jun. 4, 2024

(54) METHOD OF INCREASING LIPID PRODUCTIVITY IN NANNOCHLOROPSIS BY INTRODUCING A GENE ENCODING BOTH A THIOREDOXIN DOMAIN AND A THIOREDOXIN REDUCTASE DOMAIN

(71) Applicant: Kao Corporation, Tokyo (JP)

(72) Inventor: Tatsuro Ozaki, Wakayama (JP)

(73) Assignee: Kao Corporation, Tokyo (JP)

( * ) Notice: Subject to any disclaimer, the term of this patent is extended or adjusted under 35 U.S.C. 154(b) by 196 days.

(21) Appl. No.: 17/278,805

(22) PCT Filed: Sep. 27, 2019

(86) PCT No.: PCT/JP2019/038111
§ 371 (c)(1),
(2) Date: Mar. 23, 2021

(87) PCT Pub. No.: WO2020/071265
PCT Pub. Date: Apr. 9, 2020

(65) Prior Publication Data
US 2022/0033865 A1    Feb. 3, 2022

(30) Foreign Application Priority Data
Oct. 1, 2018    (JP) ................................. 2018-186684

(51) Int. Cl.
| | | |
|---|---|---|
| C12P 7/6409 | (2022.01) | |
| C12N 1/12 | (2006.01) | |
| C12N 9/02 | (2006.01) | |
| C12N 15/82 | (2006.01) | |
| C12R 1/89 | (2006.01) | |

(52) U.S. Cl.
CPC .............. *C12P 7/6409* (2013.01); *C12N 1/12* (2013.01); *C12N 9/0051* (2013.01); *C12N 15/82* (2013.01); *C12R 2001/89* (2021.05)

(58) Field of Classification Search
None
See application file for complete search history.

(56) References Cited

U.S. PATENT DOCUMENTS

| | | |
|---|---|---|
| 2017/0073711 A1 | 3/2017 | Iwai et al. |
| 2017/0114376 A1 | 4/2017 | Ozaki et al. |
| 2018/0245110 A1 | 8/2018 | Sugihara |
| 2019/0071698 A1 | 3/2019 | Sugihara |

FOREIGN PATENT DOCUMENTS

| | | |
|---|---|---|
| JP | JP WO2015/137449 | 9/2015 |
| JP | JP WO2015/194628 | 12/2015 |
| WO | WO 2016/193959 A2 | 12/2016 |
| WO | WO 2017/043419 A1 | 3/2017 |
| WO | WO 2017/183421 A1 | 10/2017 |

OTHER PUBLICATIONS

Accession A0A1S6KMA4. May 10, 2017 (Year: 2017).*
Accession A0A221C9C8. Oct. 25, 2017 (Year: 2017).*
Chica et al. Curr Opin Biotechnol. Aug. 2005; 16(4):378-84. (Year: 2005).*
Singh et al. Curr Protein Pept Sci. 2017, 18, 1-11 (Year: 2017).*
Li, FW et al., The origin and evolution of phototropins. Front Plant Sci. Aug. 12, 2015;6:637. doi: 10.3389/fpls.2015.00637. PMID: 26322073; PMCID: PMC4532919.
International Search Report for PCT/JP2019/038111; I.A. fd Sep. 27, 2019, mailed Dec. 10, 2019 from the Japan Patent Office, Tokyo, Japan.
International Preliminary Report on Patentability (IPRP), Chapter I of the Patent Cooperation Treaty, including the Written Opinion, for PCT/JP2019/038111; I.A. fd Sep. 27, 2019, issued Mar. 23, 2021, by the International Bureau of WIPO, Geneva, Switzerland.
Corteggiani Carpinelli, E, et al. "Chromosome scale genome assembly and transcriptome profiling of *Nannochloropsis gaditana* in nitrogen depletion." Mol Plant. Feb. 2014;7(2):323-35. doi: 10.1093/mp/sst120. Epub Aug. 21, 2013. PMID: 23966634.
Serrato AJ, et al. "A novel NADPH thioredoxin reductase, localized in the chloroplast, which deficiency causes hypersensitivity to abiotic stress in *Arabidopsis thaliana*." J Biol Chem. Oct. 15, 2004;279(42):43821-7. doi: 10.1074/jbc.M404696200. Epub Jul. 28, 2004. PMID: 15292215.
Database GenBank [online], Accession No. EWM21431, https://www.ncbi.nlm.nih.gov/protein/EWM21431, Feb. 14, 2014 uploaded, [retrieved on Nov. 29, 2019], Definition: thioredoxin reductase [Nannochloropsis gaditana].
Database GenBank [online], Accession No. EWM26110, https://www.ncbi.nlm.nih.gov/protein/EWM26110, Feb. 14, 2014 uploaded, [retrieved on Nov. 29, 2019], Definition: long chain acyl-CoA synthetase [Nannochloropsis gaditana].
Liang, F, et al., "Effects of overexpressing photosynthetic carbon flux control enzymes in the cyanobacterium *Synechocystis* PCC 6803." Metab Eng. Nov. 2016;38:56-64. doi: 10.1016/j.ymben.2016.06.005. Epub Jun. 18, 2016. PMID: 27328433.
Driever, SM et al., "Increased SBPase activity improves photosynthesis and grain yield in wheat grown in greenhouse conditions." Philos Trans R Soc Lond B Biol Sci. Sep. 26, 2017;372(1730):20160384. doi: 10.1098/rstb.2016.0384. PMID: 28808101; PMCID: PMC5566882.
Notice of Reasons for Refusal, for JP Appl No. 2020-550384, issued Jul. 25, 2023, from the Japan Patent Office, Tokyo, Japan.
Tanaka, T., "Application of marine diatoms to next-generation biofuels," Biotechnology, (2012) 90(7), p. 392-395.
Sasaki, S., "A female researcher's drifting; Investigating the relationship between plants and light and discovering the key enzyme for fatty acid synthesis," Chemical and Biological, (2012), 50(10), 756-760.

(Continued)

*Primary Examiner* — Christian L Fronda
(74) *Attorney, Agent, or Firm* — Sterne, Kessler, Goldstein & Fox P.L.L.C.

(57) ABSTRACT

A method of producing lipids, containing the steps of:
culturing an alga in which expression of a gene encoding a protein containing a thioredoxin domain and a thioredoxin reductase domain is enhanced, and
producing fatty acids or lipids containing the same as components.

18 Claims, No Drawings
Specification includes a Sequence Listing.

(56) References Cited

OTHER PUBLICATIONS

Buchanan, B, "Role of Light in the Regulation of Chloroplast Enzymes," Ann. Rev. Plant Physiol., Jun. 1980, 31:341-374.
Sasaki Y, et al., "Link between light and fatty acid synthesis: thioredoxin-linked reductive activation of plastidic acetyl-CoA carboxylase." Proc Natl Acad Sci U S A. Sep. 30, 1997;94(20):11096-101. doi: 10.1073/pnas.94.20.11096.

* cited by examiner

METHOD OF INCREASING LIPID PRODUCTIVITY IN NANNOCHLOROPSIS BY INTRODUCING A GENE ENCODING BOTH A THIOREDOXIN DOMAIN AND A THIOREDOXIN REDUCTASE DOMAIN

TECHNICAL FIELD

The present invention relates to a method of producing lipids.

BACKGROUND ART

Fatty acids are one kind of the principal components of lipids. In vivo, fatty acids are bonded to glycerin via an ester bond to form lipids such as triacylglycerol (hereinafter, also merely referred to as "TAG"). Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents or disinfectants. Cationic surfactants such as alkylamine salts and mono- or dialkyl-quaternary amine salts, as other higher alcohol derivatives, are commonly used for fiber treatment agents, hair conditioning agents or disinfectants. Further, benzalkonium type quaternary ammonium salts are commonly used for disinfectants, antiseptics, or the like. Furthermore, fats and oils derived from plants are also used as raw materials of biodiesel fuels.

As mentioned above, fatty acids are widely used in various applications. Therefore, attempts have been made on improving productivity of the fatty acids or the lipids in vivo by using plants and the like. Furthermore, an example of fundamental characteristics depending on the applications and usefulness of fatty acids includes the number of carbon atoms. Therefore, controlling of the number of carbon atoms of the fatty acids, namely, a chain length thereof has also been attempted.

In recent years, researches on renewable energy have been promoted toward realization of a sustainable society. In particular, photosynthetic microorganisms are expected as biofuel organisms without competing with grain in addition to an effect on reducing carbon dioxide.

Especially in recent years, algae attract attention due to its usefulness in biofuel production. The algae can produce lipids that can be used as the biodiesel fuels through photosynthesis, and do not compete with foods. Therefore, the algae attract attention as next-generation biomass resources. Moreover, it is also reported that the algae have higher lipid productivity and lipid accumulation ability in comparison with plants.

Plants, and algae such as photosynthetic microorganisms are known to fix carbon by carrying out photosynthesis through the Calvin-Benson-Bassham cycle (hereinafter also referred to as "CBB cycle"). The CBB cycle consists of 13 reactions and one carbon dioxide molecule is fixed per reaction cycle. The resulting photosynthetic product is utilized not only as a biological component but also as an energy source. It has therefore been attempted to control produced biomass by reinforcing the CBB cycle so as to increase the photosynthetic ability of plants, algae, or the like (Non-Patent Literatures 1 and 2).

CITATION LIST

Non-Patent Literatures

Non-Patent Literature 1: Liang F. and Lindblad P., Metab Eng. 2016 November; 38:56-64
Non-Patent Literature 2: Driever S. M. et al., Philos Trans R Soc Land B Biol Sci. 2017 Sep. 26; 372(1730)

SUMMARY OF INVENTION

The present invention relates to a method of producing lipids, containing the steps of:
culturing a transformant of an alga wherein expression of a gene encoding a protein containing a thioredoxin domain (hereinafter, also referred to as "TRX domain") and a thioredoxin-reductase domain (hereinafter, also referred to as "TR domain") is enhanced, and
producing lipids.

Further, the present invention relates to a transformant of an alga wherein expression of a gene encoding a protein containing a TRX domain and a TR domain.

MODE FOR CARRYING OUT THE INVENTION

In view of ample knowledge not yet having been obtained concerning relationship between control of photosynthetic ability by reinforcing CBB cycle and fatty acid synthesis, the present inventors conducted a thorough investigation in this regard.

Thioredoxin is known to exhibit activity of reducing various target proteins. Particularly in chloroplasts, thioredoxin is known to be reduced by ferredoxin-thioredoxin reductase (thioredoxin reductase) and the reduced thioredoxin reduces enzyme proteins and the like involved in the CBB cycle, thereby regulating enzyme activity of target proteins. The present inventors therefore focused on thioredoxin, which is considered to be involved in control of the CBB cycle, and attempted to increase productivity of lipids by enhancing expression of thioredoxin.

The present inventors first carried out a localization analysis using a reporter gene on the basis of sequence information on all the genes of *Nannochloropsis oceanica* and identified thioredoxins presumed to function in chloroplasts. Among the identified thioredoxins, the inventors focused particularly on proteins having both a TRX domain and a TR domain (hereinafter also referred to as "TRTRX") and found that when expression of TRTRX is enhanced in cells of algae, productivity of produced fatty acids and lipids containing the same as constituent components is significantly improved.

The present invention was completed based on these findings.

The present invention relates to providing a method of producing lipids, which improves productivity of fatty acids or lipids containing the same as components.

Further, the present invention relates to providing a transformant in which productivity of fatty acids or lipids containing the same as components is improved.

In the transformant of the present invention, expression of a protein containing the TRX domain and the TR domain is enhanced, and as a result, production amount of lipids can be increased. Therefore, according to the method of producing lipids of the present invention, productivity of fatty acids or lipids containing the same as components can be improved.

Moreover, expression of a protein containing the TRX domain and the TR domain is enhanced in the transformant of the present invention, and thereby the transformant of the present invention is excellent in the productivity of fatty acids or lipids containing the same as components.

Other and further features and advantages of the invention will appear more fully from the following description.

The term "lipid(s)" in the present specification, covers a simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, the fatty acid group in molecules of a simple lipid and a complex lipid is expressed as "fatty acid residue". Then, unless otherwise specified, a term "fatty acid" is used as a generic term for "free fatty acid", and "fatty acid residue" contained in a salt or an ester compound, or the like.

Moreover, a term "fatty acids or lipids containing the same as components" in the present specification is generically used including "free fatty acids" and "lipids having the fatty acid residues". The weight (production amount) of the fatty acids can be measured according to the method used in Examples.

Herein, in the present specification, the term "fatty acid" is not particularly limited as long as it is an aliphatic carboxylic acid, but the number of carbon atoms of an acyl group is preferably 2 or more and 22 or less, more preferably 4 or more and 22 or less, more preferably 6 or more and 22 or less, more preferably 8 or more and 22 or less, more preferably 10 or more and 22 or less, and further preferably 12 or more and 20 or less.

Further in the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in the present specification, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

In the present specification, the term "TRTRX" means a protein containing a TRX domain and a TR domain. TRTRX is a protein (enzyme) possessing the functions of two proteins, namely, thioredoxin and thioredoxin reductase. In chloroplasts, thioredoxin reductase is generally reduced by ferredoxin or NADPH that have been reduced in Photochemical System I, and thioredoxin is then reduced by the reduced thioredoxin reductase. Reduced thioredoxin reduces target protein by a dithiol-disulfide exchange reaction and controls the activity of the target protein.

Further, in the present invention, the term "TRTRX gene" means a gene containing a DNA encoding the TRX domain and the TR domain.

The term "TRX domain" in the present specification means a region consisting of a conserved amino acid sequence necessary for thioredoxin activity (hereinafter, also referred to as "TRX activity"), and the term "TR domain" means a region consisting of a conserved amino acid sequence necessary for thioredoxin reductase activity (hereinafter, also referred to as "TR activity"). Further, the term "TRX activity" in the present specification means activity of reducing target protein by a dithiol-disulfide exchange reaction, and the term "TR activity" means enzyme activity of reducing thioredoxin.

In addition, whether an amino acid sequence has a TRX domain or a TR domain can be confirmed by performing an analysis on the CDD v3.16-50369 PSSMs database using the NCBI Conserved Domain Search program (www.ncbi.nlm.nih.gov/Structure/cdd/wrpsb.cgi), by setting the "Expect Value (e-value) threshold" to 0.010000. With regard to the CDD v3.16-50369 PSSMs database, as one type of the "TRX domain" used in the present invention can be mentioned "Thioredoxin_like superfamily (Accession No. cl00388)" and as one type of the "TR domain" can be mentioned "TRX_reduct (Accession No. TIGR01292)". From a viewpoint of TRX activity and TR activity, e-value is preferably 0.01 or less, more preferably $1 \times 10^{-5}$ or less, more preferably $1 \times 10^{-10}$ or less, and further preferably $1 \times 10^{-20}$ or less. Further, from a viewpoint of TRX activity and TR activity, the TRX domain and the TR domain preferably contain a motif of cysteine-arbitrary amino acid-arbitrary amino acid-cysteine (CXXC) respectively, the TRX domain more preferably contains a motif sequence of cysteine-glycine-proline-cysteine (CGPC), and the TR domain more preferably contains a motif sequence of cysteine-alanine-isoleucine-cysteine (CAIC).

It can be confirmed whether a protein used for the present invention has TRX activity and TR activity, for example, by analyzing a gene encoding a protein containing the TRX domain or the TR domain according to a method described in Serrato A. J., et al., The Journal of Biological Chemistry, 2004, vol. 279(42).

The TRTRX used for the present invention is not particularly limited as long as the TRTRX is a protein (enzyme) containing the TRX domain and the TR domain, and which can improve lipid productivity of algae by enhancing the expression.

Examples of the TRX domain and the TR domain preferred for the present invention include a TRX domain consisting of any one of the amino acid sequences selected from the group consisting of the following amino acid sequences (A) to (D), and a TR domain consisting of any one of the amino acid sequences selected from the group consisting of the following amino acid sequences (E) to (H).

(A) the amino acid sequence at positions 529 to 629 of the amino acid sequence set forth in SEQ ID NO: 1;

(B) an amino acid sequence having 60% or more identity with the amino acid sequence (A), and constituting the TRX domain having TRX activity;
(C) the amino acid sequence at positions 525 to 625 of the amino acid sequence set forth in SEQ ID NO: 3;
(D) an amino acid sequence having 60% or more identity with the amino acid sequence (C), and constituting the TRX domain having TRX activity;
(E) the amino acid sequence at positions 137 to 448 of the amino acid sequence set forth in SEQ ID NO: 1;
(F) an amino acid sequence having 60% or more identity with the amino acid sequence (E), and constituting the TR domain having TR activity;
(G) the amino acid sequence at positions 134 to 445 of the amino acid sequence set forth in SEQ ID NO: 3; and
(H) an amino acid sequence having 60% or more identity with the amino acid sequence (G), and constituting the TR domain having TR activity.

As the TRTRX used for the present invention, a protein containing the TRX domain consisting of the amino acid sequence (A) or (B) and the TR domain consisting of the amino acid sequence (E) or (F), a protein containing the TRX domain consisting of the amino acid sequence (A) or (B) and the TR domain consisting of the amino acid sequence (G) or (H), a protein containing the TRX domain consisting of the amino acid sequence (C) or (D) and the TR domain consisting of the amino acid sequence (E) or (F), and a protein containing the TRX domain consisting of the amino acid sequence (C) or (D) and the TR domain consisting of the amino acid sequence (G) or (H) are preferred. Among them, a protein containing the TRX domain consisting of the amino acid sequence (A) or (B) and the TR domain consisting of the amino acid sequence (E) or (F), and a protein containing the TRX domain consisting of the amino acid sequence (C) or (D) and the TR domain consisting of the amino acid sequence (G) or (H) are more preferred.

Further, as the TRTRX used for the present invention, the following proteins (I) to (L) are more preferred. Herein, the proteins (I) and (J) are included in the protein containing the TRX domain consisting of the amino acid sequence (A) or (B) and the TR domain consisting of the amino acid sequence (E) or (F). Further, the proteins (K) and (L) are included in the protein containing the TRX domain consisting of the amino acid sequence (C) or (D) and the TR domain consisting of the amino acid sequence (G) or (H).
(I) a protein consisting of the amino acid sequence set forth in SEQ ID NO: 1;
(J) a protein consisting of an amino acid sequence having 60% or more identity with the amino acid sequence of the protein (I), and containing a TRX domain and a TR domain having TRX activity and TR activity;
(K) a protein consisting of the amino acid sequence set forth in SEQ ID NO: 3; and
(L) a protein consisting of an amino acid sequence having 60% or more identity with the amino acid sequence of the protein (K), and containing a TRX domain and a TR domain having TRX activity and TR activity.

The amino acid sequence set forth in SEQ ID NO: 1, and the amino acid sequence set forth in SEQ ID NO: 3 are explained below.

The protein (I) consisting of the amino acid sequence set forth in SEQ ID NO: 1 is a TRTRX (hereinafter, also referred to as "NoTRTRX") derived from *Nannochloropsis oceanica* strain NIES-2145 being algae belonging to the genus *Nannochloropsis oceanica*.

The TRX domain consisting of the amino acid sequence at positions 529 to 629 of the amino acid sequence set forth in SEQ ID NO: 1 (the amino acid sequence (A)) has TRX activity. Further, the TR domain consisting of the amino acid sequence at positions 137 to 448 of the amino acid sequence set forth in SEQ ID NO: 1 (the amino acid sequence (E)) has TR activity. Furthermore, the protein consisting of the amino acid sequence set forth in SEQ ID NO: 1 (the protein (I)) contains the TRX domain and the TR domain (e-values thereof show $1.51 \times 10^{-29}$ and $2.47 \times 10^{-136}$ respectively, and each of them has the CGPC motif sequence or the CAIC motif sequence), and show TRX activity and TR activity.

The protein (K) consisting of the amino acid sequence set forth in SEQ ID NO: 3 is a TRTRX (hereinafter, also referred to as "NgTRTRX") derived from *Nannochloropsis gaditana* strain CCMP526 being algae belonging to the genus *Nannochloropsis gaditana*.

The TRX domain consisting of the amino acid sequence at positions 525 to 625 of the amino acid sequence set forth in SEQ ID NO: 3 (the amino acid sequence (C)) has TRX activity. Further, the TR domain consisting of the amino acid sequence at positions 134 to 445 of the amino acid sequence set forth in SEQ ID NO: 3 (the amino acid sequence (G)) has TR activity. Furthermore, the protein consisting of the amino acid sequence set forth in SEQ ID NO: 3 (the protein (K)) contains the TRX domain and the TR domain (e-values thereof show $3.04 \times 10^{-31}$ and $6.61 \times 10^{-134}$ respectively, and each of them has the CGPC motif sequence or the CAIC motif sequence), and show TRX activity and TR activity.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a domain or a protein can be used in which TRX activity or TR activity is kept and a part of the amino acid sequence is subjected to mutation.

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the Splicing overlap extension (SOE)-PCR reaction (Horton et al., Gene 77, 61-68, 1989), the ODA method (Hashimoto-Gotoh et al., Gene, 152, 271-276, 1995), and the Kunkel method (Kunkel, T. A., Proc. Natl. Acad. Sci. USA, 1985, 82, 488). Further, commercially available kits such as Site-Directed Mutagenesis System Mutan-Super Express Km kit (Takara Bio), Transformer™ Site-Directed Mutagenesis kit (Clontech Laboratories), and KOD-Plus-Mutagenesis Kit (TOYOBO) can also be utilized. Furthermore, an objective gene can also be obtained by introducing a genetic mutation at random, and then performing an evaluation of the enzyme activities and a gene analysis thereof by an appropriate method.

In the amino acid sequence (B), the identity with the amino acid sequence (A) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity of the TRX domain.

Further, specific examples of the amino acid sequence (B) include an amino acid sequence in which 1 or several (for example 1 or more and 40 or less, preferably 1 or more and 35 or less, more preferably 1 or more and 30 or less, further preferably 1 or more and 25 or less, furthermore preferably 1 or more and 20 or less, furthermore preferably 1 or more and 15 or less, furthermore preferably 1 or more and 10 or less, furthermore preferably 1 or more and 9 or less, furthermore preferably 1 or more and 7 or less, furthermore preferably 1 or more and 5 or less, furthermore preferably 1 or more and 3 or less, furthermore preferably 1 or 2, and furthermore preferably 1) amino acids are deleted, substituted, inserted or added to the amino acid sequence (A), and constituting the TRX domain having TRX activity.

In the amino acid sequence (D), the identity with the amino acid sequence (C) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity of the TRX domain.

Further, specific examples of the amino acid sequence (D) include an amino acid sequence in which 1 or several (for example 1 or more and 40 or less, preferably 1 or more and 35 or less, more preferably 1 or more and 30 or less, further preferably 1 or more and 25 or less, furthermore preferably 1 or more and 20 or less, furthermore preferably 1 or more and 15 or less, furthermore preferably 1 or more and 10 or less, furthermore preferably 1 or more and 9 or less, furthermore preferably 1 or more and 7 or less, furthermore preferably 1 or more and 5 or less, furthermore preferably 1 or more and 3 or less, furthermore preferably 1 or 2, and furthermore preferably 1) amino acids are deleted, substituted, inserted or added to the amino acid sequence (C), and constituting the TRX domain having TRX activity.

In the amino acid sequence (F), the identity with the amino acid sequence (E) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TR activity of the TR domain.

Further, specific examples of the amino acid sequence (F) include an amino acid sequence in which 1 or several (for example 1 or more and 124 or less, preferably 1 or more and 109 or less, more preferably 1 or more and 93 or less, further preferably 1 or more and 78 or less, furthermore preferably 1 or more and 62 or less, furthermore preferably 1 or more and 46 or less, furthermore preferably 1 or more and 31 or less, furthermore preferably 1 or more and 28 or less, furthermore preferably 1 or more and 21 or less, furthermore preferably 1 or more and 15 or less, furthermore preferably 1 or more and 9 or less, furthermore preferably 1 or more and 6 or less, and furthermore preferably 1 or more and 3 or less) amino acids are deleted, substituted, inserted or added to the amino acid sequence (E), and constituting the TR domain having TR activity.

In the amino acid sequence (H), the identity with the amino acid sequence (G) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TR activity of the TR domain.

Further, specific examples of the amino acid sequence (H) include an amino acid sequence in which 1 or several (for example 1 or more and 124 or less, preferably 1 or more and 109 or less, more preferably 1 or more and 93 or less, further preferably 1 or more and 78 or less, furthermore preferably 1 or more and 62 or less, furthermore preferably 1 or more and 46 or less, furthermore preferably 1 or more and 31 or less, furthermore preferably 1 or more and 28 or less, furthermore preferably 1 or more and 21 or less, furthermore preferably 1 or more and 15 or less, furthermore preferably 1 or more and 9 or less, furthermore preferably 1 or more and 6 or less, and furthermore preferably 1 or more and 3 or less) amino acids are deleted, substituted, inserted or added to the amino acid sequence (G), and constituting the TR domain having TR activity.

In the protein (J), the identity with the amino acid sequence of the protein (I) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity and TR activity.

Further, specific examples of the protein (J) include a protein in which 1 or several (for example 1 or more and 254 or less, preferably 1 or more and 222 or less, more preferably 1 or more and 190 or less, further preferably 1 or more and 158 or less, furthermore preferably 1 or more and 127 or less, furthermore preferably 1 or more and 94 or less, furthermore preferably 1 or more and 63 or less, furthermore preferably 1 or more and 57 or less, furthermore preferably 1 or more and 44 or less, furthermore preferably 1 or more and 31 or less, furthermore preferably 1 or more and 19 or less, furthermore preferably 1 or more and 12 or less, and furthermore preferably 1 or more and 6 or less) amino acids are deleted, substituted, inserted or added to the amino acid sequence of the protein (I), containing the TRX domain and the TR domain, and having TRX activity TR activity.

In the protein (L), the identity with the amino acid sequence of the protein (K) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity and TR activity.

Further, specific examples of the protein (L) include a protein in which 1 or several (for example 1 or more and 253 or less, preferably 1 or more and 221 or less, more preferably 1 or more and 189 or less, further preferably 1 or more and 158 or less, furthermore preferably 1 or more and 126 or less, furthermore preferably 1 or more and 95 or less, furthermore preferably 1 or more and 63 or less, furthermore preferably 1 or more and 56 or less, furthermore preferably 1 or more and 44 or less, furthermore preferably 1 or more and 31 or less, furthermore preferably 1 or more and 18 or less, furthermore preferably 1 or more and 12 or less, and furthermore preferably 1 or more and 6 or less) amino acids are deleted, substituted, inserted or added to the amino acid sequence of the protein (K), containing the TRX domain and the TR domain, and having TRX activity TR activity.

In addition, the TRTRX used in the present invention may be a protein consisting of an amino acid sequence obtained by addition of a signal peptide involved in protein transport, an amino acid sequence that is known to increase protein stability or the like to the amino acid sequence containing the TRX domain and the TR domain. Further, the TRTRX used in the present invention may be a protein, for example, consisting of an amino acid sequence wherein a putative chloroplast transit signal sequence present on a region on the N-terminal side of the amino acid sequence of the proteins (I) to (L) is changed to another chloroplast transit signal sequence that functions in the host. In prediction of localization using ChloroP (www.cbs.dtu.dk/services/ChloroP/), the amino acid sequence at positions 1 to 35 of the amino acid sequence set forth in SEQ ID NO: 1 is predicted to be a chloroplast transit signal sequence. In fact, the present inventors verified that addition of the amino acid sequence at positions 1 to 100 of the amino acid sequence set forth in SEQ ID NO: 1 to the N-terminal end of a reporter protein can cause the reporter protein to localize to chloroplasts. Since the CS-score in the ChloroP analysis is high, it is predicted that the amino acid sequence at positions 1 to 49 or at positions 1 to 117 of SEQ ID NO: 3 is also a chloroplast-transit signal sequence.

The full length of the TRTRX containing the TRX domain and the TR domain used for the present invention is not particularly limited, but 2,000 or less amino acid residues are preferable, 1,500 or less amino acid residues are more preferable, 1,000 or less amino acid residues are more preferable, 800 or less amino acid residues are more preferable, 700 or less amino acid residues are more preferable, and 650 or less amino acid residues are further preferable.

Further, the full length of the TRX domain is, from a viewpoint of containing the TRX domain and the TR domain, preferably 200 or more amino acid residues, more preferably 300 or more amino acid residues, and further preferably 400 or more amino acid residues.

The protein consisting of the TRX domain, TR domain, or the amino acid sequence containing the same can be obtained by chemical techniques, genetic engineering techniques or the like that are ordinarily carried out. For example, as for the TRTRX, a natural product-derived protein can be obtained through isolation, purification and the like from an alga having the TRTRX gene on a genome, such as *Nannochloropsis oceanica* and *Nannochloropsis gaditana*. In addition, the protein consisting of the amino acid sequence containing the TRX domain and the TR domain can be obtained by artificial chemical synthesis based on the amino acid sequence set forth in SEQ ID NO: 1 or 3. Alternatively, as a recombinant protein, protein consisting of the amino acid sequence containing the TRX domain and the TR domain may also be prepared by gene recombination technologies.

The TRTRX used for the present invention may be used alone or in combination with two or more kinds thereof. Further, the TRX domain or the TR domain contained in the TRTRX may be used one kind or in combination with two or more kinds of the TRX domain or the TR domain.

Note that the algae such as *Nannochloropsis* can be obtained from culture collection such as private or public research institutes or the like. For example, *Nannochloropsis oceanica* strain NIES-2145 can be obtained from National Institute for Environmental Studies (NIES). Further, *Nannochloropsis gaditana* strain CCMP526 can be obtained from National Center for Marine Algae and Microbiota.

In the present invention, expression of the TRTRX is preferably enhanced by using a gene encoding the TRTRX, according to a method described below.

The gene encoding the TRTRX that can be used for the present invention is a gene containing a nucleotide sequence consisting of a DNA encoding the TRX domain and the TR domain (preferably, a nucleotide sequence encoding any one of amino acid sequences selected from the group consisting of the amino acid sequences (A) to (D), and a nucleotide sequence encoding any one of amino acid sequences selected from the group consisting of the amino acid sequences (E) to (H). Specific examples of the nucleotide sequence consisting of a DNA encoding the TRX domain and the TR domain include the following nucleotide sequences (a) to (d) and the following nucleotide sequences (e) to (h).

(a) the nucleotide sequence at positions 1585 to 1887 of the nucleotide sequence set forth in SEQ ID NO: 2;
(b) a nucleotide sequence having 60% or more identity with the nucleotide sequence (a), and encoding an amino acid sequence constituting the TRX domain having TRX activity;
(c) the nucleotide sequence at positions 1573 to 1875 of the nucleotide sequence set forth in SEQ ID NO: 4;
(d) a nucleotide sequence having 60% or more identity with the nucleotide sequence (c), and encoding an amino acid sequence constituting the TRX domain having TRX activity;
(e) the nucleotide sequence at positions 409 to 1344 of the nucleotide sequence set forth in SEQ ID NO: 2;
(f) a nucleotide sequence having 60% or more identity with the nucleotide sequence (e), and encoding an amino acid sequence constituting the TR domain having TR activity;
(g) the nucleotide sequence at positions 400 to 1335 of the nucleotide sequence set forth in SEQ ID NO: 4; and
(h) a nucleotide sequence having 60% or more identity with the nucleotide sequence (g), and encoding an amino acid sequence constituting the TR domain having TR activity.

As the TRTRX gene used for the present invention, a gene containing the nucleotide sequence (a) or (b) which encodes an amino acid sequence constituting the TRX domain, and the nucleotide sequence (e) or (f) which encodes an amino acid sequence constituting the TR domain, a gene containing the nucleotide sequence (a) or (b) which encodes an amino acid sequence constituting the TRX domain, and the nucleotide sequence (g) or (h) which encodes an amino acid sequence constituting the TR domain, a gene containing the nucleotide sequence (c) or (d) which encodes an amino acid sequence constituting the TRX domain, and the nucleotide sequence (e) or (f) which encodes an amino acid sequence constituting the TR domain, and a gene containing the nucleotide sequence (c) or (d) which encodes an amino acid sequence constituting the TRX domain, and the nucleotide sequence (g) or (h) which encodes an amino acid sequence constituting the TR domain are preferred. Among them, a gene containing the nucleotide sequence (a) or (b) which encodes an amino acid sequence constituting the TRX domain, and the nucleotide sequence (e) or (f) which encodes an amino acid sequence constituting the TR domain, and a gene containing the nucleotide sequence (c) or (d) which encodes an amino acid sequence constituting the TRX domain, and the nucleotide sequence (e) or (f) which encodes an amino acid sequence constituting the TR domain are more preferred.

Further, as the TRTRX gene used for the present invention, the following DNA (i) to (l) are more preferred. Herein, the DNA (i) and (j) are included in a gene containing the nucleotide sequence (a) or (b) which encodes an amino acid sequence constituting the TRX domain, and the nucleotide sequence (e) or (f) which encodes an amino acid sequence constituting the TR domain. Further, the DNA (k) and (l) are included in a gene containing the nucleotide sequence (c) or (d) which encodes an amino acid sequence constituting the TRX domain, and the nucleotide sequence (g) or (h) which encodes an amino acid sequence constituting the TR domain.

(i) a DNA consisting of the nucleotide sequence set forth in SEQ ID NO: 2;
(j) a DNA consisting of a nucleotide sequence having 60% or more identity with the nucleotide sequence of the DNA (i), and encoding a protein containing the TRX domain and the TR domain having TRX activity and TR activity;
(k) a DNA consisting of the nucleotide sequence set forth in SEQ ID NO: 4; and
(l) a DNA consisting of a nucleotide sequence having 60% or more identity with the nucleotide sequence of the DNA (k), and encoding a protein containing the TRX domain and the TR domain having TRX activity and TR activity.

The DNA (i) consisting of the nucleotide sequence set forth in SEQ ID NO: 2 is a gene encoding the protein consisting of the amino acid sequence set forth in SEQ ID NO: 1, and which is a TRTRX gene derived from *Nannochloropsis oceanica* strain NIES-2145 (hereinafter, also referred to as "NoTRTRX gene").

The DNA (k) consisting of the nucleotide sequence set forth in SEQ ID NO: 4 is a gene encoding the protein consisting of the amino acid sequence set forth in SEQ ID NO: 3, and which is a TRTRX gene derived from *Nannochloropsis gaditana* strain CCMP526 (hereinafter, also referred to as "NgTRTRX gene").

In the nucleotide sequence (b), the identity with the nucleotide sequence of the nucleotide sequence (a) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity of the TRX domain.

Further, the nucleotide sequence (b) is also preferably a nucleotide sequence in which 1 or several (for example 1 or more and 121 or less, preferably 1 or more and 106 or less, more preferably 1 or more and 90 or less, further preferably 1 or more and 75 or less, further preferably 1 or more and 60 or less, further preferably 1 or more and 45 or less, further preferably 1 or more and 30 or less, further preferably 1 or more and 27 or less, further preferably 1 or more and 21 or less, further preferably 1 or more and 15 or less, further preferably 1 or more and 9 or less, further preferably 1 or more and 6 or less, and furthermore preferably 1 or more and 3 or less) nucleotides are deleted, substituted, inserted or added to the nucleotide sequence (a), and encoding an amino acid sequence constituting the TRX domain having TRX activity.

In the nucleotide sequence (d), the identity with the nucleotide sequence of the nucleotide sequence (c) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity of the TRX domain.

Further, the nucleotide sequence (d) is also preferably a nucleotide sequence in which 1 or several (for example 1 or more and 121 or less, preferably 1 or more and 106 or less, more preferably 1 or more and 90 or less, further preferably 1 or more and 75 or less, further preferably 1 or more and 60 or less, further preferably 1 or more and 45 or less, further preferably 1 or more and 30 or less, further preferably 1 or more and 27 or less, further preferably 1 or more and 21 or less, further preferably 1 or more and 15 or less, further preferably 1 or more and 9 or less, further preferably 1 or more and 6 or less, and furthermore preferably 1 or more and 3 or less) nucleotides are deleted, substituted, inserted or added to the nucleotide sequence (c), and encoding an amino acid sequence constituting the TRX domain having TRX activity.

In the nucleotide sequence (f), the identity with the nucleotide sequence of the nucleotide sequence (e) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TR activity of the TR domain.

Further, the nucleotide sequence (f) is also preferably a nucleotide sequence in which 1 or several (for example 1 or more and 374 or less, preferably 1 or more and 327 or less, more preferably 1 or more and 280 or less, further preferably 1 or more and 234 or less, further preferably 1 or more and 187 or less, further preferably 1 or more and 140 or less, further preferably 1 or more and 93 or less, further preferably 1 or more and 84 or less, further preferably 1 or more and 65 or less, further preferably 1 or more and 46 or less, further preferably 1 or more and 28 or less, further preferably 1 or more and 18 or less, and furthermore preferably 1 or more and 9 or less) nucleotides are deleted, substituted, inserted or added to the nucleotide sequence (e), and encoding an amino acid sequence constituting the TR domain having TR activity.

In the nucleotide sequence (h), the identity with the nucleotide sequence of the nucleotide sequence (g) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TR activity of the TR domain.

Further, the nucleotide sequence (h) is also preferably a nucleotide sequence in which 1 or several (for example 1 or more and 374 or less, preferably 1 or more and 327 or less, more preferably 1 or more and 280 or less, further preferably 1 or more and 234 or less, further preferably 1 or more and 187 or less, further preferably 1 or more and 140 or less, further preferably 1 or more and 93 or less, further preferably 1 or more and 84 or less, further preferably 1 or more and 65 or less, further preferably 1 or more and 46 or less, further preferably 1 or more and 28 or less, further preferably 1 or more and 18 or less, and furthermore preferably 1 or more and 9 or less) nucleotides are deleted, substituted, inserted or added to the nucleotide sequence (g), and encoding an amino acid sequence constituting the TR domain having TR activity.

In the DNA (j), the identity with the nucleotide sequence of the DNA (i) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity and TR activity.

Further, the DNA (j) is also preferably a gene in which 1 or several (for example 1 or more and 763 or less, preferably 1 or more and 667 or less, more preferably 1 or more and 572 or less, further preferably 1 or more and 477 or less, further preferably 1 or more and 381 or less, further preferably 1 or more and 286 or less, further preferably 1 or more and 190 or less, further preferably 1 or more and 171 or less, further preferably 1 or more and 133 or less, further preferably 1 or more and 95 or less, further preferably 1 or more and 57 or less, further preferably 1 or more and 38 or less, and furthermore preferably 1 or more and 19 or less) nucleotides are deleted, substituted, inserted or added to the nucleotide sequence set forth in SEQ ID NO: 2, and encoding a protein containing the TRX domain and the TR domain having TRX activity and TR activity.

Furthermore, the DNA (j) is also preferably a gene capable of hybridizing with a DNA consisting of the nucleotide sequence complementary with the DNA (i) under a stringent condition, and encoding a protein containing the TRX domain and the TR domain having TRX activity and TR activity.

In the DNA (l), the identity with the nucleotide sequence of the DNA (k) is 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more, in view of TRX activity and TR activity.

Further, the DNA (l) is also preferably a gene in which 1 or several (for example 1 or more and 760 or less, preferably 1 or more and 665 or less, more preferably 1 or more and 570 or less, further preferably 1 or more and 475 or less, further preferably 1 or more and 380 or less, further preferably 1 or more and 285 or less, further preferably 1 or more and 190 or less, further preferably 1 or more and 171 or less, further preferably 1 or more and 133 or less, further preferably 1 or more and 95 or less, further preferably 1 or more and 57 or less, further preferably 1 or more and 38 or less, and furthermore preferably 1 or more and 19 or less) nucleotides are deleted, substituted, inserted or added to the nucleotide sequence set forth in SEQ ID NO: 4, and encoding a protein containing the TRX domain and the TR domain having TRX activity and TR activity.

Furthermore, the DNA (l) is also preferably a gene capable of hybridizing with a DNA consisting of the nucleotide sequence complementary with the DNA (k) under a stringent condition, and encoding a protein containing the TRX domain and the TR domain having TRX activity and TR activity.

Examples of a mutation include deletion, substitution, insertion and addition of a nucleotide. Specific examples of a method of introducing the mutation into a nucleotide sequence includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer™ Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

In addition, the TRTRX gene used in the present invention may be a gene consisting of a DNA obtained by addition of a DNA encoding a signal peptide involved in protein transport, a protein that is known to increase protein stability, or the like, to the DNA encoding the TRX domain and the TR domain. Further, the TRTRX gene used in the present invention may be a DNA consisting of a nucleotide sequence, wherein a nucleotide sequence encoding a putative chloroplast transit signal sequence present on a region on the 5' side in the nucleotide sequence of the DNAs (i) to (l) is changed to another nucleotide sequence encoding a chloroplast transit signal sequence that functions in the host. In prediction of localization using ChloroP (www.cbs.dtu.dk/services/ChloroP/), the nucleotide sequence at positions 1 to 105 of the nucleotide sequence set forth in SEQ ID NO: 2 is predicted to encode a chloroplast transit signal sequence. In fact, the present inventors verified that addition of the nucleotide sequence at positions 1 to 300 of the nucleotide sequence set forth in SEQ ID NO: 2 to the 5' end of a nucleotide sequence encoding a reporter protein can cause the reporter protein to localize to chloroplasts. Further, it is predicted that the nucleotide sequence at positions 1 to 147 or at positions 1 to 351 of the nucleotide sequence set forth in SEQ ID NO: 4 encodes a chloroplast transit signal sequence, due to its high CS-score by ChloroP analysis.

The full length of the TRTRX gene that can be used for the present invention is not particularly limited, but 6,000 or less nucleotides are preferable, 4,500 or less nucleotides are more preferable, 3,000 or less nucleotides are more preferable, 2,400 or less nucleotides are more preferable, 2,100 or less nucleotides are more preferable, and 1,900 or less nucleotides are further preferable.

Further, the full length of the DNA encoding the TRX domain is, from a viewpoint of containing a DNA encoding the TRX domain and a DNA encoding the TR domain, preferably 600 or more nucleotides, more preferably 900 or more nucleotides, and further preferably 1,200 or more nucleotides.

A DNA encoding the TRX domain, a DNA encoding the TR domain, and a gene containing a nucleotide sequence consisting thereof can be obtained by genetic engineering techniques that are ordinarily carried out. For example, the TRTRX gene can be artificially synthesized based on the amino acid sequence set forth in SEQ ID NO: 1 or 3, or the nucleotide sequence set forth in SEQ ID NO: 2 or 4. The synthesis of the TRTRX gene can be achieved by utilizing, for example, the services of Invitrogen. Further, the gene can also be obtained by cloning from an alga having a TRTRX gene on a genome, such as a *Nannochloropsis oceanica* and a *Nannochloropsis gaditana*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. In addition, depending on the type of the host to be used, a part of the nucleotide sequence set forth in SEQ ID NO: 2 or 4 may be optimized. For example, GeneArt Gene Synthesis service from Thermo Fisher Scientific can be used therefor.

The TRTRX gene used for the present invention may be used alone or in combination with two or more kinds thereof. Further, a DNA encoding the TRX domain or the TR domain which is contained in the TRTRX gene may be used alone or in combination with two or more kinds of a DNA encoding the TRX domain or the TR domain.

The transformant of the present invention can be obtained by introducing the TRTRX gene into a host according to an ordinarily method. Specifically, the transformant can be produced by preparing a recombinant vector or a gene expression cassette which is capable of expressing the gene in a host cell, introducing this vector or cassette into the host cell, and thereby transforming the host cell. In the transformant of the present invention, it is preferred that expression of the gene is enhanced.

The TRTRX gene to be introduced into each of hosts is preferably optimized in codon in accordance with use frequency of codon in the host to be used. Information of codons used in each of organisms is available from Codon Usage Database (www.kazusa.or.jp/codon/).

Further, the transformant of the present invention can be obtained by, in a host having the TRTRX gene on a genome, modifying expression regulation region of the gene by an ordinary method thereby enhancing expression of the gene. Specifically, it can be prepared by interchanging a promoter sited upstream of the TRTRX gene present on a genome of the host with that having higher promoter activity, or the like.

In the transformant of the present invention, from viewpoints of improving photosynthetic ability and improving lipid productivity, it is also preferred that expression of at least one kind or two or more kinds of proteins involved in the pathway of fatty acid (FA) synthesis and the pathway of TAG synthesis is enhanced, in addition to the TRTRX. Specific examples of the proteins involved in the pathway of fatty acids synthesis and the pathway of TAG synthesis include an acetyl-CoA carboxylase (hereinafter, also referred to as "ACC"), an acyl-carrier protein (hereinafter, also referred to as "ACP"), a holo-ACP synthase (phosphopantetheinyl transferases), an ACP-malonyltransferase (hereinafter, also referred to as "MAT"), a β-ketoacyl-ACP synthase (hereinafter, also referred to as "KAS"), a β-ketoacyl-ACP reductase (hereinafter, also referred to as "KAR"), a hydroxyacyl-ACP dehydratase (hereinafter, also referred to as "HD"), an enoyl-ACP reductase (hereinafter, also referred to as "MR"), an acyl-ACP thioesterase (hereinafter, also referred to as "TE"), an acyl-CoA synthetase (hereinafter, also referred to as "ACS"), a glycerol-3-phosphate dehydrogenase (hereinafter, also referred to as "G3PDH"), an acyltransferase (hereinafter, also referred to as "AT") such as a glycerol-3-phosphate acyltransferase (hereinafter, also referred to as "GPAT"), a lysophosphatidic acid acyltransferase (hereinafter, also referred to as "LPAAT"), and diacylglycerol acyltransferase, and a phosphatidate phosphatase (hereinafter, also referred to as "PAP").

From viewpoints of improving photosynthetic ability and improving lipid productivity, it is preferred that expression of at least one kind or two or more kinds of proteins selected from the ACC, the ACP, the MS, the TE, the ACS, and the AT, in addition to the TRTRX, is enhanced, more preferred that expression of at least one kind or two or more kinds of proteins selected from the TE, the ACS, and the AT is enhanced, further preferred that expression of at least one kind or two or more kinds of proteins selected from the TE, the ACS, and the DGAT is enhanced. Further, from viewpoints of improving photosynthetic ability and improving lipid productivity, it is preferred that expression of the DGAT is enhanced, more preferred that expression of the ACS and the DGAT is enhanced, and further preferred that expression of the TE, the ACS and the DGAT is enhanced.

The TE that can be used in the present invention is not particularly limited, but needs to be a protein having acyl-ACP thioesterase activity (hereinafter, also referred to as "TE activity"). Herein, the term "TE activity" means an activity of hydrolyzing the thioester bond of the acyl-ACP.

A TE is an enzyme that hydrolyzes the thioester bond of the acyl-ACP synthesized by a fatty acid synthase such as the KAS to produce a free fatty acid. The function of the TE terminates the fatty acid synthesis on the ACP, and then the thus-hydrolyzed fatty acid is supplied to the synthesis of polyunsaturated fatty acids or TAG or the like.

Therefore, lipid productivity of the transformant to be used for the lipid production, particularly productivity of the fatty acids can be further improved by enhancing expression of the TE, in addition to the TRTRX.

To date, it is known that a TE shows different reaction specificities depending on the number of carbon atoms and the number of unsaturated bonds of the acyl group (fatty acid residue) constituting an acyl-ACP being a substrate. Therefore, TE is considered to be an important factor in determining the fatty acid composition of an organism. In particular, when a host originally having no gene encoding a TE is used, enhancing expression of a gene encoding the TE (hereinafter, also referred to as "TE gene") is preferable.

The TE that can be used in the present invention can be appropriately selected from ordinary TEs and proteins functionally equivalent to the TEs, according to a kind of host or the like. Specific examples thereof include a TE derived from *Nannochloropsis oceanica* (SEQ ID NO: 37, the nucleotide sequence of a gene encoding the same: SEQ ID NO: 38). Moreover, as the proteins functionally equivalent to them, a protein consisting of an amino acid sequence having 50% or more (preferably 70% or more, more preferably 80% or more, and further preferably 90% or more) identity with the amino acid sequence of the TE described above, and having TE activity, can be also used.

The TE activity of the protein can be confirmed by, for example, introducing a DNA produced by linking the TE gene to the downstream of a promoter which functions in a host cell such as *Escherichia coli*, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by using a gas chromatographic analysis or the like.

Alternatively, the TE activity can be measured by introducing a DNA produced by linking the TE gene to the downstream of a promoter which functions in a host cell such as *Escherichia coli*, into a host cell, culturing the thus-obtained cell under the conditions suitable for the expression of the introduced TE gene, and subjecting a disruption liquid of the cell to a reaction which uses acyl-ACPs, as substrates, prepared according to the method of Yuan et al. (Yuan L. et al., Proc. Natl. Acad. Sci. U.S.A., 1995, vol. 92 (23), p. 10639-10643).

The AT that can be used in the present invention is not particularly limited, but needs to be a protein having acyltransferase activity (hereinafter, also referred to as "AT activity"). Herein, the term "AT activity" means the activity to catalyze the acylation of a glycerol compound such as a glycerol-3-phosphate, a lysophosphatidic acid, and a diacylglycerol.

An AT is a protein catalyzing the acylation of a glycerol compound such as a glycerol-3-phosphate, a lysophosphatidic acid and a diacylglycerol. Fatty acyl-CoA, in which a free fatty acid is bonded to CoA, or acyl-ACP is catalyzed by each AT to be incorporated into a glycerol backbone. Then, the three fatty acid molecules are ester-bonded to one glycerol molecule to produce and accumulate TAG.

Therefore, lipid productivity of the transformant to be used for the lipid production, particularly productivity of the fatty acids can be further improved by enhancing expression of the AT, in addition to the TRTRX.

To date, it is known that there are several ATs showing different reaction specificities depending on the number of carbon atoms and the number of unsaturated bonds of the acyl group (fatty acid residue) constituting a fatty acyl-CoA or a fatty acyl-ACP being a substrate. Therefore, AT is considered to be an important factor in determining the fatty acid composition of an organism. In particular, when a host originally having no gene encoding an AT (hereinafter, also referred to as "AT gene") is used, enhancing expression of an AT gene is preferable.

The AT that can be used in the present invention can be appropriately selected from ordinary ATs and proteins functionally equivalent to the ATs, according to a kind of host or the like. Specific examples thereof include a DGAT derived from *Nannochloropsis oceanica* (SEQ ID NO: 33, the nucleotide sequence of a gene encoding the same: SEQ ID NO: 34; or SEQ ID NO: 76, the nucleotide sequence of a gene encoding the same: SEQ ID NO: 77). Moreover, as the proteins functionally equivalent to them, a protein consisting of an amino acid sequence having 50% or more (preferably 70% or more, more preferably 80% or more, and further preferably 90% or more) identity with the amino acid sequence of the DGAT described above, and having AT activity, can be also used.

The ACS that can be used in the present invention is not particularly limited, but needs to be a protein having acyl-CoA synthetase activity (hereinafter, also referred to as "ACS activity"). Here, the term "ACS activity" means activity of bonding a free fatty acid and a CoA to produce an acyl-CoA.

The ACS is a protein involved synthesis of acyl-CoA by adding CoA to a biosynthesized fatty acid (free fatty acid). Therefore, lipid productivity of the transformant to be used for the lipid production, particularly productivity of the fatty acids can be further improved by enhancing expression of the ACS, in addition to the TRTRX.

The ACS that can be used in the present invention can be appropriately selected from ordinary ACSs and proteins functionally equivalent to the ACSs, according to a kind of host or the like. Specific examples thereof include a long chain acyl-CoA synthetase (hereinafter, also merely referred to as "LACS") derived from *Nannochloropsis oceanica* (SEQ ID NO: 35, the nucleotide sequence of a gene encoding the same (hereinafter, also referred to as "LACS gene"): SEQ ID NO: 36) and the like. Moreover, as the proteins functionally equivalent to them, a protein consisting of an amino acid sequence having 50% or more (preferably 70% or more, more preferably 80% or more, and further preferably 90% or more) identity with the amino acid sequence of the LACS derived from *Nannochloropsis oceanica*, and having ACS activity, can be also used.

In the transformant of the present invention, from viewpoints of improving photosynthesis and improving lipid productivity, expression of at least one kind or two or more kinds of proteins involved in the CBB cycle, in addition to the TRTRX, is preferably enhanced. Examples of the proteins involved in the CBB cycle include a protein such as a fructose-1,6-bisphosphate aldolase (hereinafter, also referred to as "FBA"), a transketolase (hereinafter, also referred to as "TK") and a ribose-5-phosphate isomerase (hereinafter, also referred to as "RPI").

The TK that can be used for the present invention is not particularly limited, but needs to be a protein having transketolase activity (hereinafter, also referred to as "TK activity"). Herein, the term "TK activity" means activity of transferring the ketol group of ketose to the aldehyde group of aldose.

In the present specification, the TK is a protein (enzyme) that catalyzes, in the CBB cycle, a reaction of producing an erythrose-4-phosphate and a xylulose-5-phosphate from a fructose-6-phosphate and a glyceraldehyde-3-phosphate, and a reaction of producing a xylulose-5-phosphate and a ribose-5-phosphate from a sedoheptulose-7-phosphate and a glyceraldehyde-3-phosphate. By promoting such reactions, the CBB cycle is reinforced and production of photosynthetic products and the like from carbon dioxide can be enhanced. Accordingly, it is speculated that by enhancing expression of the TK in addition to the TRTRX, the photosynthetic ability in a transformant can be improved, and consequently, the enhanced photosynthetic ability can lead to an improvement in lipid productivity.

The TK that can be used in the present invention can be appropriately selected from ordinary TKs and proteins functionally equivalent to the TKs, according to a kind of host or the like. Specific examples thereof include a TK derived from *Nannochloropsis oceanica* (SEQ ID NO: 27, the nucleotide sequence of a gene encoding the same (hereinafter, also referred to as "TK gene"): SEQ ID NO: 28). Moreover, as the proteins functionally equivalent to them, a protein consisting of an amino acid sequence having 50% or more (preferably 70% or more, more preferably 80% or more, and further preferably 90% or more) identity with the amino acid sequence of the TK described above, and having TK activity, can be also used.

It can be confirmed whether the protein to be used for the present invention has TK activity by, for example, a method described in Plant Physiol. (1989) 90, 814-819 and the like. Specifically, it is confirmed by preparing solution containing target proteins by an ordinary method, and analyzing a formation of an erythrose-4-phosphate and a xylulose-5-phosphate from mixture of a fructose-6-phosphate and a glyceraldehyde-3-phosphate, or a formation of a xylulose-5-phosphate and a ribose-5-phosphate from mixture of a sedoheptulose-7-phosphate and a glyceraldehyde-3-phosphate.

The FBA that can be used for the present invention is not particularly limited, but needs to be a protein having fructose-1,6-bisphosphate aldolase activity (hereinafter, also referred to as "FBA activity"). Herein, the term "FBA activity" means activity of condensing glyceraldehyde-3-phosphate and dihydroxyacetone phosphate or condensing erythrose-4-phosphate and dihydroxyacetone phosphate.

In the present specification, the FBA is a protein (enzyme) that catalyzes, in the CBB cycle, a reaction of producing a fructose-1,6-bisphosphate from a glyceraldehyde-3-phosphate and dihydroxyacetone phosphate, and a reaction of producing a sedoheptulose-1,7-bisphosphate from an erythrose-4-phosphate and dihydroxyacetone phosphate. By promoting such reactions, the CBB cycle is reinforced and production of photosynthetic products and the like from carbon dioxide can be enhanced. Accordingly, it is speculated that by enhancing expression of the FBA in addition to the TRTRX, the photosynthetic ability in a transformant can be enhanced, and consequently, the enhanced photosynthetic ability can lead to an improvement in lipid productivity.

The FBA that can be used in the present invention can be appropriately selected from ordinary FBAs and proteins functionally equivalent to the FBAs, according to a kind of host or the like. Specific examples thereof include a TK derived from *Nannochloropsis oceanica* (SEQ ID NO: 29, the nucleotide sequence of a gene encoding the same (hereinafter, also referred to as "FBA gene"): SEQ ID NO: 30). Moreover, as the proteins functionally equivalent to them, a protein consisting of an amino acid sequence having 50% or more (preferably 70% or more, more preferably 80% or more, and further preferably 90% or more) identity with the amino acid sequence of the FBA described above, and having FBA activity, can be also used.

It can be confirmed whether the protein to be used in the present invention has the FBA activity by, for example, a method described in Plant Physiol. (1989) 90, 814-819 and the like. Specifically, it is confirmed by preparing solution containing target proteins by an ordinary method, and analyzing a formation of a fructose-1,6-bisphosphate from mixture of a glyceraldehyde-3-phosphate and a dihydroxyacetone phosphate, or a formation of a sedoheptulose-1,7-bisphosphate from mixture of an erythrose-4-phosphate and a dihydroxyacetone phosphate.

The RPI that can be used for the present invention is not particularly limited, but needs to be a protein having ribose-5-phosphate isomerase activity (hereinafter, also referred to as "RPI activity"). Herein, the term "RPI activity" means activity of converting an aldehyde group of an aldose to a keto group.

In the present specification, the RPI is a protein (enzyme) which catalyzes a reaction of conversion of a ribulose-5-phosphate from a ribose-5-phosphate. By promoting such a reaction, the CBB cycle is reinforced and production of photosynthetic products and the like from carbon dioxide can be enhanced. Accordingly, it is speculated that by enhancing expression of the RPI in addition to the TRTRX, the photosynthetic ability in a transformant can be enhanced, and consequently, the enhanced photosynthetic ability can lead to an improvement in lipid productivity.

The RPI that can be used in the present invention can be appropriately selected from ordinary RPIs and proteins functionally equivalent to the RPIs, according to a kind of host or the like. Specific examples thereof include an RPI derived from *Nannochloropsis oceanica* (SEQ ID NO: 31, the nucleotide sequence of a gene encoding the same (hereinafter, also referred to as "RPI gene"): SEQ ID NO: 32). Moreover, as the proteins functionally equivalent to them, a protein consisting of an amino acid sequence having 50% or more (preferably 70% or more, more preferably 80% or more, and further preferably 90% or more) identity with the amino acid sequence of the RPI described above, and having RPI activity, can be also used.

It can be confirmed whether the protein to be used for the present invention has RPI activity by, for example, a method described in The Plant Journal (2006) 48, 606-618 and the like. Specifically, it is confirmed by preparing solution containing target proteins, and analyzing a formation of a ribulose-5-phosphate from mixture of a ribose-5-phosphate.

The amino acid sequence information of the TE, the AT, the LACS, the TK, the FBA, and the RPI, and the nucleotide sequence information of the genes encoding the same can be obtained from, for example, National Center for Biotechnology Information (NCBI), or the like.

Further, the transformant in which expression of the TE gene, the AT gene, the LACS gene, the TK gene, the FBA gene, or the RPI gene is enhanced can be prepared by an ordinary method. For example, the transformant can be prepared by a method similar to the above-described method for enhancing expression of the TRTRX gene, such as a method for introducing the each gene into a host, a method for modifying expression regulation regions of the gene in the host having the each gene on a genome, or the like.

The gene to be introduced into each of hosts is preferably optimized in codon in accordance with use frequency of codon in the host to be used. Information of codons used in each of organisms is available from Codon Usage Database (www.kazusa.or.jp/codon/).

In the present specification, a cell in which expression of a gene encoding the objective protein is enhanced is also referred to as the "transformant", and a cell in which expression a gene encoding the objective protein is not enhanced is also referred to as the "host" or "wild type strain".

In the transformant used for the present invention, total amount of each fatty acid amount (total fatty acid amount) is significantly improved compared to that in the host itself.

The productivity of fatty acids and lipids of the host and the transformant can be measured by the method used in Examples.

A method of preparing the transformant of the present invention is explained. However, the present invention is not limited thereto.

The host for the transformant can be appropriately selected from ordinarily used hosts. For example, microorganisms (such as algae including microalgae) can be used as the host in the present invention. Among them, algae are more preferable.

As for algae or microalgae used for the present invention, from a viewpoint of establishment of a gene recombinant technique, algae belonging to the genus *Chlamydomonas*, algae belonging to the genus *Chlorella*, algae belonging to the genus *Phaeodactylum*, and algae belonging to the genus *Nannochloropsis* are preferred. Furthermore, from a viewpoint of lipid productivity, algae belonging to the phylum Heterokontophyta are also preferred, and algae belonging to the class Eustigmatophyceae are more preferred. Specific examples of algae belonging to the class Eustigmatophyceae include algae belonging to the genus *Nannochloropsis*, algae belonging to the genus *Monodopsis*, algae belonging to the genus *Vischeria*, algae belonging to the genus *Chlorobotrys*, and *Goniochloris*. Among them, from a viewpoint of lipid productivity, algae belonging to the genus *Nannochloropsis* is preferable. Specific examples of the algae belonging to the genus *Nannochloropsis* include *Nannochloropsis oceanica*,

*Nannochloropsis oculata, Nannochloropsis gaditana, Nannochloropsis salina, Nannochloropsis limnetica, Nannochloropsis granulata, Nannochloropsis* sp., and the like. Among them, from a viewpoint of lipid productivity, *Nannochloropsis oceanica* or *Nannochloropsis gaditana* is preferable, and *Nannochloropsis oceanica* is more preferable.

A vector for use as the plasmid vector for gene expression or a vector containing the gene expression cassette (plasmid) may be any vector capable of introducing the gene encoding the objective protein into a host, and expressing the objective gene in the host cell. For example, a vector which has expression regulation regions such as a promoter and a terminator in accordance with the type of the host to be used, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include pUC18 (manufactured by Takara Bio), pUC19 (manufactured by Takara Bio), pUC118 (manufactured by Takara Bio), P66 (*Chlamydomonas* Center), P-322 (*Chlamydomonas* Center), pPha-T1 (see Journal of Basic Microbiology, 2011, vol. 51, p. 666-672) and pJET1 (manufactured by COSMO BIO). In particular, in the case of using the algae belonging to the genus *Nannochloropsis* as the host, pUC18, pPha-T1 or pJET1 is preferably used. Moreover, when the host is the algae belonging to the genus *Nannochloropsis*, the host can be transformed, with referring to the method described in Proceedings of the National Academy of Sciences of the United States of America, 2011, vol. 108(52), by using the DNA fragment (gene expression cassette) consisting of the objective gene, a promoter and a terminator.

Moreover, a kind of promoter regulating expression of the gene encoding an objective protein introduced into the expression vector can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), a promoter of Rubisco operon (rbc), PSI reaction center protein (psaA and psaB), D1 protein of PSII (psbA), c-phycocyanin β subunit (cpcB), cauliflower mosaic virus 35S RNA promoter, promoters for housekeeping genes (e.g., tubulin promoter, actin promoter and ubiquitin promoter), *Brassica napus* or *Brassica rapa*-derived Napin gene promoter, a RubisCO promoter derived from plants, a promoter of a violaxanthin/(chlorophyll a)-binding protein gene derived from the genus *Nannochloropsis* (VCP1 promoter, VCP2 promoter) (Proceedings of the National Academy of Sciences of the United States of America, 2011, vol. 108(52)), a promoter of an oleosin-like protein LDSP (lipid droplet surface protein) gene derived from the genus *Nannochloropsis* (Astrid Vieler, et al., PLOS Genetics, 2012; 8(11): e1003064. doi: 10.1371), a promoter of a glutamine synthetase gene derived from the genus *Nannochloropsis* (GS promoter), and a promoter of an ammonium transporter gene derived from the genus *Nannochloropsis* (AMT promoter). In a case where algae belonging to the genus *Nannochloropsis* are used as a host in the present invention, a tubulin promoter, a heat shock protein promoter, a promoter of a violaxanthin/chlorophyll a-binding protein gene (VCP1 promoter, VCP2 promoter), and a promoter of an oleosin-like protein LDSP gene derived from the genus *Nannochloropsis*, a promoter of an ACP (acyl-carrier protein) gene (ACP promoter), a promoter of a desaturase gene, a promoter of an AT (acyltransferase) gene (AT promoter), a GS promoter and an AMT promoter can be preferably used. In addition, algae belonging to the genus *Nannochloropsis* have been generally known to efficiently produce lipids under nutrient (in particular, nitrogen)-depleted conditions and/or high light conditions. Thus, it is more preferable to use a promoter that can be strongly expressed under such conditions. From a viewpoint of expressing under the nitrogen-depleted conditions or the high light conditions, a promoter of a gene involved in the fatty acid synthetic pathway or the TAG synthetic pathway, or a promoter of a gene involved in nitrogen assimilation is preferred, the promoter of the LDSP gene, the ACP promoter, the promoter of the desaturase gene, the AT promoter, the GS promoter, and the AMT promoter are more preferred, and the promoter of the LDSP gene, the GS promoter and the AMT promoter are further preferred.

Moreover, a kind of selection marker for confirming introduction of the gene encoding an objective protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, a gentamicin resistance gene, and a hygromycin resistance gene. Further, it is also possible to use a deletion of an auxotrophy-related gene or the like as the selection marker gene.

Introduction of the gene encoding an objective protein to the vector can be conducted by an ordinary technique such as restriction enzyme treatment and ligation.

The method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. In a case where an alga belonging to the genus *Nannochloropsis* is used as a host, transformation can also be performed by using the electroporation method described in Randor Radakovits, et al., Nature Communications, DOI: 10.1038/ncomms1688, 2012, or the like.

The selection of a transformant having an objective gene fragment introduced therein can be carried out by utilizing the selection marker or the like. For example, the selection can be carried out by using an indicator whether a transformant acquires the drug resistance as a result of introducing a drug resistance gene into a host cell together with an objective DNA fragment upon the transformation. Further, the introduction of an objective DNA fragment can also be confirmed by PCR method using a genome as a template or the like.

In a host having the TRTRX gene on a genome, a method of modifying expression regulation regions of the genes and thereby enhancing expression of the genes is explained.

The "expression regulation region" indicates the promoter, the terminator or untranslated region, in which these sequences are generally involved in regulation of the expression amount (transcription amount, translation amount) of the gene adjacent thereto. In a host having the TRTRX gene on a genome, productivity of fatty acids can be improved by modifying expression regulation regions of the genes and enhancing expression of the genes.

Specific examples of the method of modifying the expression regulation regions include interchange of promoters. In the host having the TRTRX gene on the genome, expression of the gene can be enhanced by interchanging the promoter of the gene with a promoter having higher transcriptional activity.

As for the host, among the species described above, one containing the TRTRX gene on a genome can be preferably used.

The promoter used for promoter interchanging is not particularly limited, and can be appropriately selected from promoters that are higher in the transcriptional activity than the promoter of the TRTRX gene, and suitable for production of fatty acids.

In a case where an alga belonging to the genus *Nannochloropsis* is used as a host, a tubulin promoter, a heat shock protein promoter, a promoter of the violaxanthin/(chlorophyll a)-binding protein gene (VCP1 promoter, VCP2 promoter), a promoter of an oleosin-like protein LDSP gene derived from the genus *Nannochloropsis*, a GS promoter, and an AMT promoter can preferably be used. From a viewpoint of improvement in lipid productivity, a promoter of a gene which is involved in the pathway of fatty acid biosynthesis or TAG biosynthesis, and a promoter of a gene which is involved in the pathway of nitrogen assimilation is preferable, and the promoter of the LDSP gene, the ACP promoter, the promoter of a desaturase gene, the AT promoter, the GS promoter, and the AMT promoter are more preferable, and the promoter of the LDSP gene are further preferable.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. As a result, the target promoter on the genome is substituted with other promoter fragment, and the promoter can be modified.

The method of modifying a target promoter according to such homologous recombination can be conducted with, for example, referring to literature such as Methods in molecular biology, 1995, vol. 47, p. 291-302. In particular, in the case where the host is the algae belonging to the genus *Nannochloropsis*, specific region in a genome can be modified, with referring to literature such as Proceedings of the National Academy of Sciences of the United States of America, 2011, vol. 108(52), by homologous recombination method.

In the transformant of the present invention, productivity of fatty acids or lipids containing the same as components, especially total fatty acid amount after culturing for a certain period, is improved in comparison with that in the host in which expression of the TRTRX gene is not enhanced. Accordingly, when the transformant of the present invention is cultured under suitable conditions and then the fatty acids or the lipids containing the same as components are collected from an obtained cultured product, the fatty acids or the lipids containing the same as components can be efficiently produced.

Herein, the term "cultured product" means liquid medium and a transformant subjected to cultivation.

The culture condition of the transformant of the present invention can be appropriately selected in accordance with the type of the host to be used for a transformation, and any ordinary used culture conditions for the host can be employed. Further, from a viewpoint of the production efficiency of fatty acids, for example, precursor substances involved in the fatty acid biosynthesis system, such as glycerol, acetic acid, or glucose, may be added to the medium.

In the present invention, as a medium used for culturing the algae, a medium based on natural seawater or artificial seawater, or a commercially available culture medium may be used. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the range of an amount of the transformant to be seeded is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the range of the culture temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, the range of light intensity during the light irradiation is preferably 1 to 4,000 $\mu mol/m^2/s$, more preferably 10 to 2,500 $\mu mol/m^2/s$, further preferably 100 to 2,500 $\mu mol/m^2/s$, further preferably 200 to 2,500 $\mu mol/m^2/s$, and further preferably 250 to 2,500 $\mu mol/m^2/s$, and furthermore preferably 300 to 2,500 $\mu mol/m^2/s$. Moreover, an interval of the light irradiation is not particularly limited. From the viewpoints in a manner similar to the viewpoints described above, the irradiation is preferably performed under a light and dark cycle. In 24 hours, the range of the light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the range of the concentration is preferably 0.03 (which is the same degree as the concentration under atmospheric conditions) to 10%, more preferably from 0.05 to 5%, further preferably from 0.1 to 3%, and furthermore preferably from 0.3 to 1%.

A concentration of carbonate is not particularly limited. When sodium hydrogen carbonate is used, for example, from viewpoints of the growth promotion and the improvement in the productivity of fatty acids, the range of the concentration of sodium hydrogen carbonate is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. From viewpoints of the algal growth promotion, the improvement in fatty acid productivity, and reduction of production cost, the range of the culture time is preferably from 3 to 90 days, more preferably from 7 to 30 days, and further preferably from 14 to 21 days. The culture may be performed in any of aerated and agitated culture, shaking culture or static culture. From a viewpoint of improving air-permeability, aerated and agitated culture is preferred.

A method of collecting the lipids from the cultured product is appropriately selected from an ordinary method. For example, lipid components can be isolated and collected from the above-described cultured product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain a fatty acid or a fatty acid compound, and more preferably contain a fatty acid having 2 or more and 22 or less carbon atoms or a fatty acid ester compound thereof, more preferably contain a fatty acid having 4 or more and 22 or less carbon atoms or a fatty acid ester compound thereof, more preferably contain a fatty acid having 6 or more and 22 or less carbon atoms or a fatty acid ester compound thereof, more preferably contain a fatty acid having 8 or more and 22 or less carbon atoms or a fatty acid ester compound thereof, more preferably contain a fatty acid having 10 or more and 22 or less carbon atoms or a fatty acid ester compound thereof, and further preferably contain a fatty acid having 12 or more and 20 or less carbon atoms or a fatty acid ester compound thereof in view of usability thereof.

From a viewpoint of productivity, the fatty acid ester compound contained in lipids is preferably a simple lipid or a complex lipid, more preferably a simple lipid, and further preferably a TAG.

The fatty acid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing fatty acids, methods of improving fatty acid productivity, algae, transformants and methods of preparing transformants, described below.

<1> A method of producing lipids, containing the steps of:
culturing an alga in which expression of a gene encoding a protein containing a TRX domain and a TR domain is enhanced, and
producing fatty acids or lipids containing the same as components.

<2> A method of improving lipid productivity, containing enhancing expression of a gene encoding a protein containing a TRX domain and a TR domain, to improve total fatty acid amount produced in an algal cell.

<3> The method described in the above item <1> or <2>, wherein the gene encoding the protein containing the TRX domain and the TR domain is introduced into a host to enhance expression of the gene.

<4> A method of producing lipids, containing the steps of:
culturing a transformant of an alga into which a gene encoding a protein containing a TRX domain and a TR domain is introduced, and producing fatty acids or lipids containing the same as components.

<5> A method of improving lipid productivity, containing the steps of
introducing a gene encoding a protein containing a TRX domain and a TR domain into a host to prepare a transformant of an alga, and
improving total fatty acid amount produced in a transformant cell.

<6> The method described in any one of the above items <1> to <5>, wherein the alga is an alga belonging to the phylum Heterokontophyta, preferably an alga belonging to the class Eustigmatophyceae.

<7> The method described in the above item <6>, wherein the alga belonging to the class Eustigmatophyceae is an alga belonging to the genus *Nannochloropsis*.

<8> The method described in the above item <7>, wherein the alga belonging to the genus *Nannochloropsis* is at least an alga selected from the group consisting of *Nannochloropsis oceanica, Nannochloropsis oculata, Nannochloropsis gaditana, Nannochloropsis salina, Nannochloropsis limnetica, Nannochloropsis granulata, Nannochloropsis* sp., preferably *Nannochloropsis* oceanica.

<9> The method described in any one of the above items <1> to <8>, wherein the TRX domain is a TRX domain containing a CXXC motif sequence, preferably containing a CGPC motif sequence.

<10> The method described in any one of the above items <1> to <9>, wherein the TR domain is a TR domain containing a CXXC motif sequence, preferably containing a CAIC motif sequence.

<11> The method described in any one of the above items <1> to <10>, wherein full length of the protein containing the TRX domain and the TR domain is preferably 2,000 or less amino acid residues, more preferably 1,500 or less amino acid residues, more preferably 1,000 or less amino acid residues, more preferably 800 or less amino acid residues, more preferably 700 or less amino acid residues, and further preferably 650 or less amino acid residues.

<12> The method described in any one of the above items <1> to <11>, wherein full length of the protein containing the TRX domain and the TR domain is 200 or more amino acid residues, preferably 300 or more amino acid residues, and more preferably 400 or more amino acid residues.

<13> The method described in any one of the above items <1> to <12>, wherein full length of the gene encoding the protein containing the TRX domain and the TR domain is preferably 6,000 or less nucleotides, more preferably 4,500 or less nucleotides, more preferably 3,000 or less nucleotides, more preferably 2,400 or less nucleotides, more preferably 2,100 or less nucleotides, and further preferably 1,900 or less nucleotides.

<14> The method described in any one of the above items <1> to <13>, wherein full length of the gene encoding the protein containing the TRX domain and the TR domain is 600 or more nucleotides, preferably 900 or more nucleotides, and more preferably 1,200 or more nucleotides.

<15> The method described in any one of the above items <1> to <14>, wherein the TRX domain is a domain consisting of any one of amino acid sequences selected from the group consisting of the following amino acid sequences (A) to (D):

(A) the amino acid sequence at positions 529 to 629 of the amino acid sequence set forth in SEQ ID NO: 1;
(B) an amino acid sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the amino acid sequence (A), and constituting the TRX domain having TRX activity;
(C) the amino acid sequence at positions 525 to 625 of the amino acid sequence set forth in SEQ ID NO: 3; and
(D) an amino acid sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the amino acid sequence (C), and constituting the TRX domain having TRX activity.

<16> The method described in the above item <15>, wherein the amino acid sequence (B) is an amino acid sequence in which 1 or several, preferably 1 or more and 40 or less, more preferably 1 or more and 35 or less, further preferably 1 or more and 30 or less, furthermore preferably 1 or more and 25 or less, furthermore preferably 1 or more and 20 or less, furthermore preferably 1 or more and 15 or less, furthermore preferably 1 or more and 10 or less, furthermore preferably 1 or more and 9 or less, furthermore preferably 1 or more and 7 or less, furthermore preferably 1 or more and 5 or less, furthermore preferably 1 or more and 3 or less, furthermore preferably 1 or 2, and furthermore preferably 1 amino acid is deleted, substituted, inserted or added to the amino acid sequence (A), and constituting the TRX domain having TRX activity.

<17> The method described in the above item <15>, wherein the amino acid sequence (D) is an amino acid sequence in which 1 or several, preferably 1 or more and 40 or less, more preferably 1 or more and 35 or less, further preferably 1 or more and 30 or less, furthermore preferably 1 or more and 25 or less, furthermore preferably 1 or more and 20 or less, furthermore preferably 1 or more and 15 or less, furthermore preferably 1 or more and 10 or less, furthermore preferably 1 or more and 9 or less, furthermore preferably 1 or more and 7 or less, furthermore preferably 1 or more and 5 or less, furthermore preferably 1 or more and 3 or less, furthermore preferably 1 or 2, and furthermore preferably 1 amino acid is deleted, substituted, inserted or added to the amino acid sequence (C), and constituting the TRX domain having TRX activity.

<18> The method described in any one of the above items <1> to <17>, wherein a DNA encoding the TRX domain is a DNA consisting of any one of nucleotide sequences selected from the group consisting of the following nucleotide sequences (a) to (d):

(a) the nucleotide sequence at positions 1585 to 1887 of the nucleotide sequence set forth in SEQ ID NO: 2;
(b) a nucleotide sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the nucleotide sequence (a), and encoding an amino acid sequence constituting the TRX domain having TRX activity;
(c) the nucleotide sequence at positions 1573 to 1875 of the nucleotide sequence set forth in SEQ ID NO: 4; and
(d) a nucleotide sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the nucleotide sequence (c), and encoding an amino acid sequence constituting the TRX domain having TRX activity.

<19> The method described in the above item <18>, wherein the nucleotide sequence (b) is a nucleotide sequence in which 1 or several, preferably 1 or more and 121 or less, more preferably 1 or more and 106 or less, further preferably 1 or more and 90 or less, further preferably 1 or more and 75 or less, further preferably 1 or more and 60 or less, further preferably 1 or more and 45 or less, further preferably 1 or more and 30 or less, further preferably 1 or more and 27 or less, further preferably 1 or more and 21 or less, further preferably 1 or more and 15 or less, further preferably 1 or more and 9 or less, further preferably 1 or more and 6 or less, and furthermore preferably 1 or more and 3 or less nucleotides are deleted, substituted, inserted or added to the nucleotide sequence (a), and encoding an amino acid sequence constituting the TRX domain having TRX activity.

<20> The method described in the above item <18>, wherein the nucleotide sequence (d) is a nucleotide sequence in which 1 or several, preferably 1 or more and 121 or less, more preferably 1 or more and 106 or less, further preferably 1 or more and 90 or less, further preferably 1 or more and 75 or less, further preferably 1 or more and 60 or less, further preferably 1 or more and 45 or less, further preferably 1 or more and 30 or less, further preferably 1 or more and 27 or less, further preferably 1 or more and 21 or less, further preferably 1 or more and 15 or less, further preferably 1 or more and 9 or less, further preferably 1 or more and 6 or less, and furthermore preferably 1 or more and 3 or less nucleotides are deleted, substituted, inserted or added to the nucleotide sequence (c), and encoding an amino acid sequence constituting the TRX domain having TRX activity.

<21> The method described in any one of the above items <1> to <20>, wherein the TR domain is a domain consisting of any one of amino acid sequences selected from the group consisting of the following amino acid sequences (E) to (H):

(E) the amino acid sequence at positions 137 to 448 of the amino acid sequence set forth in SEQ ID NO: 1;

(F) an amino acid sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the amino acid sequence (E), and constituting the TR domain having TR activity;

(G) the amino acid sequence at positions 134 to 445 of the amino acid sequence set forth in SEQ ID NO: 3; and (H) an amino acid sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the amino acid sequence (G), and constituting the TR domain having TR activity.

<22> The method described in the above item <21>, wherein the amino acid sequence (F) is an amino acid sequence in which 1 or several, preferably 1 or more and 124 or less, more preferably 1 or more and 109 or less, further preferably 1 or more and 93 or less, furthermore preferably 1 or more and 78 or less, furthermore preferably 1 or more and 62 or less, furthermore preferably 1 or more and 46 or less, furthermore preferably 1 or more and 31 or less, furthermore preferably 1 or more and 28 or less, furthermore preferably 1 or more and 21 or less, furthermore preferably 1 or more and 15 or less, furthermore preferably 1 or more and 9 or less, furthermore preferably 1 or more and 6 or less, and furthermore preferably 1 or more and 3 or less amino acid is deleted, substituted, inserted or added to the amino acid sequence (E), and constituting the TR domain having TR activity.

<23> The method described in the above item <21>, wherein the amino acid sequence (H) is an amino acid sequence in which 1 or several, preferably 1 or more and 124 or less, more preferably 1 or more and 109 or less, further preferably 1 or more and 93 or less, furthermore preferably 1 or more and 78 or less, furthermore preferably 1 or more and 62 or less, furthermore preferably 1 or more and 46 or less, furthermore preferably 1 or more and 31 or less, furthermore preferably 1 or more and 28 or less, furthermore preferably 1 or more and 21 or less, furthermore preferably 1 or more and 15 or less, furthermore preferably 1 or more and 9 or less, furthermore preferably 1 or more and 6 or less, and furthermore preferably 1 or more and 3 or less amino acid is deleted, substituted, inserted or added to the amino acid sequence (G), and constituting the TR domain having TR activity.

<24> The method described in any one of the above items <1> to <23>, wherein a DNA encoding the TR domain is a DNA consisting of any one of nucleotide sequences selected from the group consisting of the following nucleotide sequences (e) to (h):

(e) the nucleotide sequence at positions 409 to 1344 of the nucleotide sequence set forth in SEQ ID NO: 2;

(f) a nucleotide sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the nucleotide sequence (e), and encoding an amino acid sequence constituting the TR domain having TR activity;

(g) the nucleotide sequence at positions 400 to 1335 of the nucleotide sequence set forth in SEQ ID NO: 4; and (h) a nucleotide sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the nucleotide sequence (g), and encoding an amino acid sequence constituting the TR domain having TR activity.

<25> The method described in the above item <24>, wherein the nucleotide sequence (f) is a nucleotide sequence in which 1 or several, preferably 1 or more and 374 or less, more preferably 1 or more and 327 or less, further preferably 1 or more and 280 or less, further preferably 1 or more and 234 or less, further preferably 1 or more and 187 or less, further preferably 1 or more and 140 or less, further preferably 1 or more and 93 or less, further preferably 1 or more and 84 or less, further preferably 1 or more and 65 or less, further preferably 1 or more and 46 or less, further preferably 1 or more and 28 or less, further preferably 1 or more and 18 or less, and furthermore preferably 1 or more and 9 or less nucleotides are deleted, substituted, inserted or added to the nucleotide sequence (e), and encoding an amino acid sequence constituting the TR domain having TR activity.

<26> The method described in the above item <24>, wherein the nucleotide sequence (h) is a nucleotide sequence in which 1 or several, preferably 1 or more and 374 or less, more preferably 1 or more and 327 or less, further preferably 1 or more and 280 or less, further preferably 1 or more and 234 or less, further preferably 1 or more and 187 or less, further preferably 1 or more and 140 or less, further preferably 1 or more and 93 or less, further preferably 1 or more and 84 or less, further preferably 1 or more and 65 or less, further preferably 1 or more and 46 or less, further preferably 1 or more and 28 or less, further preferably 1 or more and 18 or less, and furthermore preferably 1 or more and 9 or less nucleotides are deleted, substituted, inserted or added to the nucleotide sequence (g), and encoding an amino acid sequence constituting the TR domain having TR activity.

<27> The method described in any one of the above items <1> to <26>, wherein the protein containing the TRX domain and the TR domain is any one of the proteins selected from the group consisting of the following proteins (I) to (L):

(I) a protein consisting of the amino acid sequence set forth in SEQ ID NO: 1;
(J) a protein consisting of an amino acid sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the amino acid sequence of the protein (I), and containing the TRX domain and the TR domain having TRX activity and TR activity;
(K) a protein consisting of the amino acid sequence set forth in SEQ ID NO: 3; and
(L) a protein consisting of an amino acid sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the amino acid sequence of the protein (K), and containing the TRX domain and the TR domain having TRX activity and TR activity.

<28> The method described in the above item <27>, wherein the protein (J) is a protein which consists of an amino acid sequence in which 1 or several, preferably 1 or more and 254 or less, more preferably 1 or more and 222 or less, further preferably 1 or more and 190 or less, furthermore preferably 1 or more and 158 or less, furthermore preferably 1 or more and 127 or less, furthermore preferably 1 or more and 95 or less, furthermore preferably 1 or more and 63 or less, furthermore preferably 1 or more and 57 or less, furthermore preferably 1 or more and 44 or less, furthermore preferably 1 or more and 31 or less, furthermore preferably 1 or more and 19 or less, furthermore preferably 1 or more and 12 or less, and furthermore preferably 1 or more and 6 or less amino acids are deleted, substituted, inserted or added to the amino acid sequence of the protein (I), and containing the TRX domain and the TR domain having TRX activity and TR activity.

<29> The method described in the above item <27>, wherein the protein (L) is a protein which consists of an amino acid sequence in which 1 or several, preferably 1 or more and 253 or less, more preferably 1 or more and 221 or less, further preferably 1 or more and 189 or less, furthermore preferably 1 or more and 158 or less, furthermore preferably 1 or more and 126 or less, furthermore preferably 1 or more and 94 or less, furthermore preferably 1 or more and 63 or less, furthermore preferably 1 or more and 56 or less, furthermore preferably 1 or more and 44 or less, furthermore preferably 1 or more and 31 or less, furthermore preferably 1 or more and 18 or less, furthermore preferably 1 or more and 12 or less, and furthermore preferably 1 or more and 6 or less amino acids are deleted, substituted, inserted or added to the amino acid sequence of the protein (K), and containing the TRX domain and the TR domain having TRX activity and TR activity.

<30> The method described in any one of the above items <1> to <29>, wherein the gene encoding the protein containing the TRX domain and the TR domain is a gene consisting of any one of the DNAs selected from the group consisting of the following DNA (i) to (l):

(i) a DNA consisting of the nucleotide sequence set forth in SEQ ID NO: 2;
(j) a DNA consisting of a nucleotide sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the nucleotide sequence of the DNA (i), and encoding a protein containing the TRX domain and the TR domain having TRX activity and TR activity;
(k) a DNA consisting of the nucleotide sequence set forth in SEQ ID NO: 4; and
(l) a DNA consisting of a nucleotide sequence having 60% or more, preferably 65% or more, more preferably 70% or more, further preferably 75% or more, further preferably 80% or more, further preferably 85% or more, further preferably 90% or more, further preferably 91% or more, further preferably 93% or more, further preferably 95% or more, further preferably 97% or more, further preferably 98% or more, and furthermore preferably 99% or more identity with the nucleotide sequence of the DNA (k), and encoding a protein containing the TRX domain and the TR domain having TRX activity and TR activity.

<31> The method described in the above item <30>, wherein the DNA (j) is a gene consisting of a nucleotide sequence in which 1 or several, preferably 1 or more and 763 or less, more preferably 1 or more and 667 or less, further preferably 1 or more and 572 or less, further preferably 1 or more and 477 or less, further preferably 1 or more and 381 or less, further preferably 1 or more and 286 or less, further preferably 1 or more and 190 or less, further preferably 1 or more and 171 or less, further preferably 1 or more and 133 or less, further preferably 1 or more and 95 or less, further preferably 1 or more and 57 or less, further preferably 1 or more and 38 or less, and furthermore preferably 1 or more and 19 or less nucleotides are deleted, substituted, inserted or added to the nucleotide sequence of the DNA (i), and encoding a protein containing the TRX domain and the TR domain having TRX activity and TR activity.

<32> The method described in the above item <30>, wherein the DNA (l) is a gene consisting of a nucleotide sequence in which 1 or several, preferably 1 or more and 760 or less, more preferably 1 or more and 665 or less, further preferably 1 or more and 570 or less, further preferably 1 or more and 475 or less, further preferably 1 or more and 380 or less, further preferably 1 or more and 285 or less, further preferably 1 or more and 190 or less, further preferably 1 or more and 171 or less, further preferably 1 or more and 133 or less, further preferably 1 or more and 95 or less, further preferably 1 or more and 57 or less, further preferably 1 or more and 38 or less, and furthermore preferably 1 or more and 19 or less nucleotides are deleted, substituted, inserted or added to the nucleotide sequence of the DNA (k), and encoding a protein containing the TRX domain and the TR domain having TRX activity and TR activity.

<33> The method described in any one of the above items <1> to <32>, wherein expression of at least one kind or two or more kinds of proteins involved in fatty acid synthetic pathway or TAG synthetic pathway is enhanced in the alga.

<34> The method described in the above item <33>, wherein at least one kind or two or more kinds of the proteins involved in fatty acid synthetic pathway or TAG synthetic pathway are at least one kind or two or more kinds of proteins selected from the group consisting of an ACC, an ACP, a holo-ACP synthase (phosphopantetheinyl transferases), a MAT, a KAS, a KAR, a HD, a KAR, a TE, an ACS, a G3PDH, an AT (GPAT, LPAAT, DGAT or the like), and a PAP, preferably are at least one kind or two or more kinds of proteins selected from the group consisting of an ACC, an ACP, a KAS, a TE, an ACS, and an AT (GPAT, LPAAT, DGAT or the like), more preferably are at least one kind or two or more kinds of proteins selected from the group consisting of a TE, an ACS and an AT (GPAT, LPAAT, DGAT or the like), and further more preferably are at least one kind or two or more kinds of proteins selected from the group consisting of a TE, an ACS and a DGAT.

<35> The method described in any one of the above items <1> to <34>, wherein expression of the DGAT, preferably the ACS and the DGAT, and more preferably the TE, the ACS and the DGAT is enhanced in the alga.

<36> The method described in the above item <34> or <35>, wherein the TE is the following protein (M) or (N):
(M) a protein consisting of the amino acid sequence set forth in SEQ ID NO: 37; or
(N) a protein consisting of an amino acid sequence having 50% or more, preferably 70% or more, more preferably 80% or more, and further preferably 90% or more identity with the amino acid sequence of the protein (M), and having TE activity.

<37> The method described in any one of the above items <34> to <36>, wherein the ACS is the following protein (O) or (P):
(O) a protein consisting of the amino acid sequence set forth in SEQ ID NO: 35; or
(P) a protein consisting of an amino acid sequence having 50% or more, preferably 70% or more, more preferably 80% or more, and further preferably 90% or more identity with the amino acid sequence of the protein (O), and having ACS activity.

<38> The method described in any one of the above items <34> to <37>, wherein the AT is any one of the ATs selected form the group consisting of the following proteins (Q) to (T):
(Q) a protein consisting of the amino acid sequence set forth in SEQ ID NO: 33;
(R) a protein consisting of an amino acid sequence having 50% or more, preferably 70% or more, more preferably 80% or more, and further preferably 90% or more identity with the amino acid sequence of the protein (Q), and having AT activity;
(S) a protein consisting of the amino acid sequence set forth in SEQ ID NO: 76; and
(T) a protein consisting of an amino acid sequence having 50% or more, preferably 70% or more, more preferably 80% or more, and further preferably 90% or more identity with the amino acid sequence of the protein (S), and having AT activity <39> The method described in any one of the above items <1> to <38>, wherein expression of at least one kind or two or more kinds of proteins involved in the CBB cycle is enhanced in the alga.

<40> The method described in the above item <39>, wherein at least one kind or two or more kinds of the proteins involved in the CBB cycle is at least one kind or two or more kinds of proteins selected from the group consisting of a TK, a FBA and an RPI.

<41> The method described in any one of the above items <1> to <40>, wherein expression of the TK, preferably the TK and the FBA, and more preferably the TK, the FBA and the RPI is enhanced in the alga.

<42> The method described in the above item <40> or <41>, wherein the TK is the following protein (U) or (V):
(U) a protein consisting of the amino acid sequence set forth in SEQ ID NO: 27; or
(V) a protein consisting of an amino acid sequence having 50% or more, preferably 70% or more, more preferably 80% or more, and further preferably 90% or more identity with the amino acid sequence of the protein (U), and having TK activity.

<43> The method described in any one of the above items <40> to <42>, wherein the FBA is the following protein (W) or (X):
(W) a protein consisting of the amino acid sequence set forth in SEQ ID NO: 29; or
(X) a protein consisting of an amino acid sequence having 50% or more, preferably 70% or more, more preferably 80% or more, and further preferably 90% or more identity with the amino acid sequence of the protein (W), and having FBA activity.

<44> The method described in any one of the above items <40> to <43>, wherein the RPI is the following protein (Y) or (Z):
(Y) a protein consisting of the amino acid sequence set forth in SEQ ID NO: 31; or
(Z) a protein consisting of an amino acid sequence having 50% or more, preferably 70% or more, more preferably 80% or more, and further preferably 90% or more identity with the amino acid sequence of the protein (Y), and having RPI activity.

<45> The method described in any one of the above items <1> to <44>, wherein the lipids contain a fatty acid or a fatty acid ester compound thereof, preferably a fatty acid having 2 or more and 22 or less carbon atoms or a fatty acid ester compound thereof, more preferably a fatty acid having 4 or more and 22 or less carbon atoms or a fatty acid ester compound thereof, more preferably a fatty acid having 6 or more and 22 or less carbon atoms or a fatty acid ester compound thereof, more preferably a fatty acid having 8 or more and 22 or less carbon atoms or a fatty acid ester compound thereof, more preferably a fatty acid having 10 or more and 22 or less carbon atoms or a fatty acid ester compound thereof, and more preferably a fatty acid having 12 or more and 20 or less carbon atoms or a fatty acid ester compound thereof.

<46> The method described in any one of the above items <1> to <45>, wherein expression of the gene is enhanced by a promoter which strongly expresses under nutrient-depleted conditions or high light conditions, preferably a promoter of a gene involved in fatty acid synthetic pathway or TAG synthetic pathway, or a promoter of a gene involved in nitrogen assimilation, more preferably a promoter of a LDSP gene, an ACP promoter, a promoter of a desaturase gene, an AT promoter, a GS promoter or an AMT promoter, or further preferably a promoter of a LDSP gene, a GS promoter, or an AMT promoter.

<47> The method described in any one of the above items <1> to <46>, wherein the alga is cultured under the conditions in which light intensity is in a range of 1 to 4,000 μmol/m$^2$/s, preferably 10 to 2,500 μmol/m$^2$/s, more preferably 100 to 2,500 μmol/m$^2$/s, more preferably 200 to 2,500 μmol/m$^2$/s, more preferably 250 to 2,500 μmol/m$^2$/s, and more preferably 300 to 2,500 μmol/m$^2$/s.

<48> The method described in any one of the above items <1> to <47>, wherein the alga is cultured by using a f/2 medium wherein concentrations of a nitrogen source and a phosphorus source are reinforced.

<49> An alga wherein expression of a gene encoding a protein containing a TRX domain and a TR domain is enhanced, and total fatty acid amount produced in a cell is improved.

<50> A transformant of an alga, wherein a gene encoding a protein containing a TRX domain and a TR domain is introduced into a host.

<51> A method of preparing a transformant of an alga, containing introducing a gene encoding a protein containing a TRX domain and a TR domain into a host.

<52> The alga, the transformant of the alga, and the method of preparing the same described in any one of the above items <49> to <51>, wherein the alga is an alga belonging to the phylum Heterokontophyta, preferably an alga belonging to the class Eustigmatophyceae.

<53> The alga, the transformant of the alga, and the method of preparing the same described in the above item <52>, wherein the alga belonging to the class Eustigmatophyceae is an alga belonging to the genus *Nannochloropsis*.

<54> The alga, the transformant of the alga, and the method of preparing the same described in the above item <53>, wherein the alga belonging to the genus *Nannochloropsis* is at least an alga selected from the group consisting of *Nannochloropsis oceanica, Nannochloropsis oculata, Nannochloropsis gaditana, Nannochloropsis salina, Nannochloropsis limnetica, Nannochloropsis granulata, Nannochloropsis* sp., preferably *Nannochloropsis oceanica*.

<55> The alga, the transformant of the alga, and the method of preparing the same described in any one of the above items <49> to <54>, wherein the TRX domain is the TRX domain specified in any one of the above items <9> and <15> to <20>.

<56> The alga, the transformant of the alga, and the method of preparing the same described in any one of the above items <49> to <55>, wherein the TR domain is the TR domain specified in any one of the above items <10> and <21> to <26>.

<57> The alga, the transformant of the alga, and the method of preparing the same described in any one of the above items <49> to <56>, wherein the protein containing the TRX domain and the TR domain is the protein specified in any one of the above items <11>, <12>, and <27> to <29>.

<58> The alga, the transformant of the alga, and the method of preparing the same described in any one of the above items <49> to <57>, wherein the gene encoding the protein containing the TRX domain and the TR domain is the gene specified in any one of the above items <13>, <14>, and <30> to <32>.

<59> The alga, the transformant of the alga, and the method of preparing the same described in any one of the above items <49> to <58>, wherein expression of at least one kind or two or more kinds of proteins involved in fatty acid synthetic pathway or TAG synthetic pathway is enhanced in the alga.

<60> The alga, the transformant of the alga, and the method of preparing the same described in the above item <59>, wherein at least one kind or two or more kinds of the proteins involved in fatty acid synthetic pathway or TAG synthetic pathway are at least one kind or two or more kinds of proteins selected from the group consisting of an ACC, an ACP, a holo-ACP synthase (phosphopantetheinyl transferases), a MAT, a KAS, a KAR, a HD, a KAR, a TE, an ACS, a G3PDH, an AT (GPAT, LPAAT, DGAT or the like), and a PAP, preferably are at least one kind or two or more kinds of proteins selected from the group consisting of an ACC, an ACP, a KAS, a TE, an ACS, and an AT (GPAT, LPAAT, DGAT or the like), more preferably are at least one kind or two or more kinds of proteins selected from the group consisting of a TE, an ACS and an AT (GPAT, LPAAT, DGAT or the like), and further more preferably are at least one kind or two or more kinds of proteins selected from the group consisting of a TE, an ACS and a DGAT.

<61> The alga, the transformant of the alga, and the method of preparing the same described in any one of the above items <49> to <60>, wherein expression of the DGAT, preferably the ACS and the DGAT, and more preferably the TE, the ACS and the DGAT is enhanced in the alga.

<62> The alga, the transformant of the alga, and the method of preparing the same described in the above item <60> or <61>, wherein the TE is the protein specified in the above item <36>.

<63> The alga, the transformant of the alga, and the method of preparing the same described in any one of the above items <60> to <62>, wherein the ACS is the protein specified in the above item <37>.

<64> The alga, the transformant of the alga, and the method of preparing the same described in any one of the above items <60> to <63>, wherein the DGAT is the protein specified in the above item <38>.

<65> The alga, the transformant of the alga, and the method of preparing the same described in any one of the above items <49> to <64>, wherein expression of at least one kind or two or more kinds of proteins involved in the CBB cycle is enhanced in the alga.

<66> The alga, the transformant of the alga, and the method of preparing the same described in the above item <65>, wherein at least one kind or two or more kinds of the proteins involved in the CBB cycle is at least one kind or two or more kinds of proteins selected from the group consisting of a TK, a FBA and an RPI.

<67> The alga, the transformant of the alga, and the method of preparing the same described in any one of the above items <49> to <66>, wherein expression of the TK, preferably the TK and the FBA, and more preferably the TK, the FBA and the RPI is enhanced in the alga.
<68> The alga, the transformant of the alga, and the method of preparing the same described in the above item <66> or <67>, wherein the TK is the protein specified in the above item <42>.
<69> The alga, the transformant of the alga, and the method of preparing the same described in any one of the above items <66> to <68>, wherein the FBA is the protein specified in the above item <43>.
<70> The alga, the transformant of the alga, and the method of preparing the same described in any one of the above items <66> to <69>, wherein the RPI is the protein specified in the above item <44>.
<71> The alga, the transformant of the alga, and the method of preparing the same described in any one of the above items <49> to <70>, wherein expression of the gene is enhanced by a promoter which strongly expresses under nutrient-depleted conditions or high light conditions, preferably a promoter of a gene involved in fatty acid synthetic pathway or TAG synthetic pathway, or a promoter of a gene involved in nitrogen assimilation, more preferably a promoter of a LDSP gene, an ACP promoter, a promoter of a desaturase gene, an AT promoter, a GS promoter or an AMT promoter, or further preferably a promoter of a LDSP gene, a GS promoter, or an AMT promoter.
<72> Use of the alga, the transformant of the alga, or the transformant prepared by the method of preparing the same, described in any one of the above items <49> to <71>, for producing lipids.
<73> The use described in the above item <72>, wherein the lipids contain a fatty acid or a fatty acid ester compound thereof, preferably a fatty acid having 2 or more and 22 or less carbon atoms or a fatty acid ester compound thereof, more preferably a fatty acid having 4 or more and 22 or less carbon atoms or a fatty acid ester compound thereof, more preferably a fatty acid having 6 or more and 22 or less carbon atoms or a fatty acid ester compound thereof, more preferably a fatty acid having 8 or more and 22 or less carbon atoms or a fatty acid ester compound thereof, more preferably a fatty acid having 10 or more and 22 or less carbon atoms or a fatty acid ester compound thereof, and more preferably a fatty acid having 12 or more and 20 or less carbon atoms or a fatty acid ester compound thereof.

EXAMPLES

Hereinafter, the present invention will be described more in detail with reference to Examples, but the present invention is not limited thereto. Herein, the nucleotide sequences of the primers used in Examples are shown in Tables 1 and 2.

TABLE 1

| SEQ ID NO: | Sequence (5' -> 3') |
|---|---|
| SEQ ID NO: 10 | CTTTTTTGTGAAGCAATGGCCAAGCTGACCAGCGC |
| SEQ ID NO: 11 | TTTCCCCCATCCCGATTAGTCCTGCTCCTCGGCCAC |

TABLE 1-continued

| SEQ ID NO: | Sequence (5' -> 3') |
|---|---|
| SEQ ID NO: 12 | CGAGCTCGGTACCCGACTGCGCATGGATTGACCGA |
| SEQ ID NO: 13 | TGCTTCACAAAAAAGACAGCTTCTTGAT |
| SEQ ID NO: 14 | TCGGGATGGGGGAAAAAAACCTCTG |
| SEQ ID NO: 15 | ACTCTAGAGGATCCCCTTTCGTAAATAAATCAGCTC |
| SEQ ID NO: 16 | GGGATCCTCTAGAGTCGACC |
| SEQ ID NO: 17 | CGGGTACCGAGCTCGAATTC |
| SEQ ID NO: 18 | CGAGCTCGGTACCCGTTCTTCCGCTTGTTGCTGCC |
| SEQ ID NO: 19 | TGTTGATGCGGGCTGAGATTGGTGG |
| SEQ ID NO: 20 | GCTTCTGTGGAAGAGCCAGTG |
| SEQ ID NO: 21 | GGCAAGAAAGCTGGGGAAAAGACAGG |
| SEQ ID NO: 22 | CCAGCTTTTCTTGCCACTGCGCATGGATTGACCGA |
| SEQ ID NO: 23 | TTCTTCCGCTTGTTGCTGCCGATGGCGGCCATGGTCTC |
| SEQ ID NO: 24 | CTTTCGTAAATAAATCAGCTCCTCCTCGGAGAAGCGAAAG |
| SEQ ID NO: 25 | CAGCCCGCATCAACAATGGCTAATACCCGCCACACCAAC |
| SEQ ID NO: 26 | CTCTTCCACAGAAGCTCACATATCCAAGGCTTCTATAAT |

TABLE 2

| SEQ ID NO: | Sequence (5' -> 3') |
|---|---|
| SEQ ID NO: 46 | CTTTTTTGTGAAGCAATGGTCGAGATTCGAAGCAT |
| SEQ ID NO: 47 | TTTCCCCCATCCCGATCAGAAGAACTCGTCCAACA |
| SEQ ID NO: 48 | CTTTTTTGTGAAGCAATGACACAAGAATCCCTGTTAC |
| SEQ ID NO: 49 | TTTCCCCCATCCCGATCAGGCGCCGGGGCGGTGTC |
| SEQ ID NO: 50 | CTTTTTTGTGAAGCAATGAGCCCAGAACGACGCCC |
| SEQ ID NO: 51 | TTTCCCCCATCCCGATCAGATCTCGGTGACGGGCAGG |
| SEQ ID NO: 52 | CGAGCTCGGTACCCGGTGTGTCCTGCGTGTTGATCAGTAG |
| SEQ ID NO: 53 | TTTTAGGGGGTGGTCGAGTTGCTGTGGTG |
| SEQ ID NO: 54 | GAAAGATCCAAGAGAGACGAGTAG |
| SEQ ID NO: 55 | AGGACCGAATCGAGGCTCTGATAAATGAGG |
| SEQ ID NO: 56 | CCTCGATTCGGTCCTTTCTTCCGCTTGTTGCTGCCGATG |
| SEQ ID NO: 57 | CGAGCTCGGTACCCGCGCAAAAAACAGACAAACTT |
| SEQ ID NO: 58 | TTTTGAAGTGTTCGGCGAGGAAAGGTTTCCTGTG |
| SEQ ID NO: 59 | TTTGGAAGAGAGTTTGCTGTTTGTAAG |
| SEQ ID NO: 60 | TGTTACATCGGCGCTTGCTTGACTTGG |
| SEQ ID NO: 61 | AGCGCCGATGTAACAGTGTGTCCTGCGTGTTGATCAG |

TABLE 2-continued

| SEQ ID NO: | Sequence (5' -> 3') |
|---|---|
| SEQ ID NO: 62 | CGCAAAAAACAGACAAACTTCGTCACTCAC |
| SEQ ID NO: 63 | CAGCCCGCATCAACAATGGCTCGCCTCTTCGTCACCG |
| SEQ ID NO: 64 | CTCTTCCACAGAAGCTTAGTACTTATACCCCTTCACG |
| SEQ ID NO: 65 | GACCACCCCCTAAAAATGGTTGCTAAAGCTGCTTTTGCC |
| SEQ ID NO: 66 | TCTCTTGGATCTTTCTTACAGATAGGCCTTGGCCTCCTTG |
| SEQ ID NO: 67 | CCGAACACTTCAAAAATGAGCCGCCAAAAGACTCTCTTTT |
| SEQ ID NO: 68 | AAACTCTCTTCCAAACTACTTCTTATTGATGACGTCGATG |
| SEQ ID NO: 69 | GACCACCCCCTAAAAATGACGCCGCAAGCCGACATCAC |
| SEQ ID NO: 70 | TCTCTTGGATCTTTCTTACTCAATGGACAACGGGC |
| SEQ ID NO: 71 | CAGCCCGCATCAACAATGCCCGCCTACACGACGACATC |
| SEQ ID NO: 72 | CTCTTCCACAGAAGCCTACTTGTAGAGATTGGCGATG |
| SEQ ID NO: 73 | CAGCCCGCATCAACAATGAGAATACCTTCCCTTATCC |
| SEQ ID NO: 74 | CTCTTCCACAGAAGCCTACGTCGTGCCCATGTTCA |
| SEQ ID NO: 75 | GTGTGTCCTGCGTGTTGATCAGTAGATGCGCAAG |

Example 1

Preparation of plasmid for NoTRTRX gene expression, Transformation into *Nannochloropsis*, and Lipid production by the transformant 1. Construction of Plasmid for Zeocin Resistance Gene Expression A zeocin resistance gene (SEQ ID NO: 5), and a tubulin promoter sequence (SEQ ID NO: 6) derived from *Nannochloropsis gaditana* strain CCMP 526 described in a literature (Randor Radakovits, et al., Nature Communications, D01:10.1038/ncomms1688, 2012) were artificially synthesized. Using the thus-synthesized DNA fragments as a template, and a pair of the primers set forth in SEQ ID NO: 10 and SEQ ID NO: 11, and a pair of the primers set forth in SEQ ID NO: 12 and SEQ ID NO: 13 shown in Table 1, PCRs were carried out, to amplify the zeocin resistance gene and the tubulin promoter sequence, respectively. Further, using a genome DNA of *Nannochloropsis oceanica* strain NIES-2145 as a template, and a pair of the primers set forth in SEQ ID NO: 14 and SEQ ID NO: 15 shown in Table 1, PCR was carried out to amplify a heat shock protein terminator sequence (SEQ ID NO: 7). Furthermore, using a plasmid vector pUC19 (manufactured by Takara Bio) as a template, and a pair of the primers set forth in SEQ ID NO: 16 and SEQ ID NO: 17 shown in Table 1, PCR was carried out to amplify a fragment of the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression. Herein, the expression plasmid consisted of the pUC19 vector sequence and an insert sequence in which the tubulin promoter sequence, the zeocin resistance gene and the heat shock protein terminator sequence were linked in this order.

2. Obtaining NoTRTRX Gene, and Construction of Plasmid for NoTRTRX Gene Expression Total RNA of *Nannochloropsis oceanica* strain NIES-2145 was extracted. The cDNA was obtained by reverse transcription using the total RNA, and SuperScript (trademark) III First-Strand Synthesis SuperMix for qRT-PCR (manufactured by invitrogen). Using the above cDNA as a template, and a pair of the primers set forth in SEQ ID NO: 25 and SEQ ID NO: 26 shown in Table 1, PCR was carried out to obtain the NoTRTRX gene fragment consisting of the nucleotide sequence set forth in SEQ ID NO: 2. Further, using a genome DNA of *Nannochloropsis oceanica* strain NIES-2145 as a template, and a pair of the primers set forth in SEQ ID NO: 18 and SEQ ID NO: 19, and a pair of the primers set forth in SEQ ID NO: 20 and SEQ ID NO: 21 shown in Table 1, PCRs were carried out to obtain a LDSP promoter sequence fragment (SEQ ID NO: 8), and a VCP1 terminator fragment (SEQ ID NO: 9). Furthermore, using the plasmid for zeocin resistance gene expression as a template, and a pair of the primers set forth in SEQ ID NO: 22 and SEQ ID NO: 17 shown in Table 1, PCR was carried out to amplify a fragment containing the cassette for zeocin resistance gene expression (the tubulin promoter sequence, the zeocin resistance gene, and the heat shock protein terminator sequence) and the pUC19 sequence.

The NoTRTRX gene fragment, and the fragment containing the LDSP promoter fragment, the VCP1 terminator fragment, and the zeocin resistance gene expression cassette and pUC19 sequence were fused by a method in a manner similar to that described above, and thereby a plasmid for NoTRTRX gene expression was constructed. Herein, the expression plasmid consisted of the pUC19 vector sequence and an insert sequence in which the LDSP promoter sequence, the NoTRTRX gene, the VCP1 terminator sequence, the tubulin promoter sequence, the zeocin resistance gene and the heat shock protein terminator sequence were linked in this order.

3. Introduction of a Cassette for NoTRTRX Gene Expression into *Nannochloropsis*, and Culturing the Transformant.

Using the plasmid for the NoTRTRX gene expression as a template, and a pair of the primers set forth in SEQ ID NO: 23 and SEQ ID NO: 24 shown in Table 1, PCR was carried out to amplify a cassette for NoTRTRX gene expression (a DNA fragment containing the LDSP promoter sequence, the NoTRTRX gene, the VCP1 terminator sequence, the tubulin promoter sequence, the zeocin resistance gene, and the heat shock protein terminator sequence).

The amplified fragment was purified using High Pure PCR Product Purification Kit (manufactured by Roche Applied Science). Herein, sterilized water was used for elution upon purification without using an elution buffer included in the kit.

About $1 \times 10^9$ cells of *Nannochloropsis oceanica* strain NIES-2145 were washed with 384 mM sorbitol solution to remove a salt, and the resultant was used as a host cell for transformation. The cassette for NoTRTRX gene expression as amplified above was mixed by about 500 ng with the host cell respectively, and electroporation was carried out under the conditions of 50 pF, 500Ω and 2,200 v/2 mm. After twenty four hours recovery cultivation in f/2 liquid medium (75 mg of NaNO$_3$, 6 mg of NaH$_2$PO$_4$·2H$_2$O, 0.5 µg of vitamin B12, 0.5 µg of biotin, 100 µg of thiamine, 10 mg of Na$_2$SiO$_3$·9H$_2$O, 4.4 mg of Na$_2$EDTA·2H$_2$O, 3.16 mg of FeCl$_3$·6H$_2$O, 12 µg of CoSO$_4$·7H$_2$O, 21 µg of ZnSO$_4$·7H$_2$O, 180 µg of MnC$_{12}$·4H$_2$O, 7 µg of CuSO$_4$·5H$_2$O, 7 µg of Na$_2$MoO$_4$·2H$_2$O/artificial sea water 1 L), the resultant was inoculated in f/2 agar medium containing 2 µg/mL of zeocin, and cultured for two to three weeks under 12 h/12 h light-dark conditions at 25° C. under an atmosphere of 0.3% CO$_2$. Each strain containing the cassette for NoTRTRX gene expression (NoTRTRX transgenic strain) was selected from the resultant colonies by a PCR method. The selected strain was inoculated to 20 mL of medium in which a nitrogen concentration in the f/2 medium was reinforced 15 times, and a phosphorus concentration therein was reinforced 5 times (hereinafter, referred to as "N15P5 medium"), and subjected to shaking culture for three weeks under the 12 h/12 h light-dark conditions at 25° C. under the atmosphere of 0.3% CO$_2$.

Then, 2 mL of the culture fluid was inoculated to 18 mL of medium in which a nitrogen concentration in the f/2 medium was reinforced 5 times, and a phosphorus concentration therein was reinforced 5 times (hereinafter, referred to as "N5P5 medium"), and subjected to shaking culture for five days under the 12 h/12 h light-dark conditions, about 100 µmol/m$^2$/s light intensity, at 25° C. under the atmosphere of 0.3% CO$_2$, to prepare preceding culture fluid. A 96-well plate and an Infinite M200 PRO (TECAN, Inc.) were used to measure turbidity at 750 nm (hereinafter, also referred to as "OD$_{750}$"). The last preceding culture fluid was inoculated to 18 mL of N5P5 medium so that the final concentration of OD$_{750}$ is 0.1, and was cultured for 5 days under the same conditions to prepare a pre-culture fluid. Herein, the light intensity was set as the normal light conditions (100 µmol/m$^2$/s). The pre-culture fluid was likewise inoculated to 18 mL of N5P5 medium so that the final concentration of OD$_{750}$ is 0.1, and was subjected to main culture under the same conditions. In addition, as a negative control, an experiment was also conducted on the wild type strain, *Nannochloropsis oceanica* strain NIES-2145. The wild-type strain was cultured (N=2), and 8 independent lines for NoTRTRX transgenic strain were cultured.

4. Extraction of Lipid from Culture Fluid of *Nannochloropsis*, and Analysis of Fatty Acids Contained Therein After the start, the main culture was sampled over time to extract lipids by the method below.

To 0.25 mL of the culture fluid, 50 µL of 1 mg/mL glyceryl triheptadecanoate (manufacture by SIGMA) solution in chloroform as an internal standard was added, and then 0.5 mL of chloroform and 1 mL of methanol were further added. The mixture was vigorously stirred and then was left for 10 minutes. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette. A nitrogen gas was blown onto the resultant chloroform layer to be dried into solid, then 50 µL of chloroform was added thereto to be re-suspended. Then, 0.5 mL of 14% boron trifluoride solution (manufactured by SIGMA) was added thereto, and the mixture was stirred and kept warm at 80° C. for 30 minutes. Thereafter, 0.5 mL of hexane and 0.5 mL of saturated saline were added thereto, and the mixture was vigorously stirred and then was left for 10 minutes at room temperature. Then, the hexane layer being upper layer was collected to obtain fatty acid esters.

The obtained fatty acid esters were provided for gas chromatographic analysis. The measuring conditions are described below.

<Gas Chromatography Conditions>

Analysis apparatus: 7890A (manufactured by Agilent Technologies)
Capillary column: DB-1 MS 30 m×200 µm×0.25 µm (manufactured by J&W Scientific)
Mobile phase: high purity helium
Oven temperature: maintained for 0.5 minutes at 150° C.→150 to 220° C. (temperature increase at 40° C./minute)→220 to 320° C. (temperature increase at 20° C./minute)→maintained for 2 minutes at 320° C. (post run: 2 minute)
Injection port temperature: 300° C.
Injection method: split injection (split ratio: 75:1)
Amount of injection: 1 µL
Cleaning vial: methanol/chloroform
Detection method: FID
Detector temperature: 300° C.

In addition, each fatty acid methyl ester was identified by subjecting each fatty acid methyl ester standard to gas chromatography under the same conditions and comparing their retention times. Further, gas chromatography-mass spectroscopy was optionally used for the identification.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of fatty acid methyl esters having 17 carbon atoms derived from the internal standard, and carried out corrections between the samples, and then the amount of each of the fatty acids per liter of the culture fluid was calculated. Further, sum of the amounts of each of the fatty acids was regarded as total fatty acid amount. Herein, the term "total fatty acid amount" in Example means sum of the amounts of C12:0, C14:0, C16:1, C16:0, C18:n and C20:n. Further, the term "n" designates an integer of 0 to 5, and the term "Cx:n" designates a total of each fatty acid having Cx:0, Cx:1, Cx:2, Cx:3, Cx:4 and Cx:5.

Table 3 shows the results. Note that in the Table below, the wild-type strain is designated as "WT", and the NoTRTRX transgenic strain is designated as "TRTRX". The days described in Table 3 indicate culturing days, and "TFA yield" indicates total fatty acid amount.

TABLE 3

| | | TFA yield (mg/L) | | | | |
|---|---|---|---|---|---|---|
| | | 7 days | 10 days | 14 days | 17 days | 21 days |
| WT | 1 | 363.9 | 709.8 | 1219.3 | 1516.4 | 1778.8 |
| | 2 | 431.6 | 772.6 | 1287.0 | 1578.1 | 1844.1 |
| | Average | 397.8 | 741.2 | 1253.2 | 1547.2 | 1811.5 |
| TRTRX | Line 1 | 386.6 | 784.9 | 1291.3 | 1632.0 | 1891.6 |
| | Line 2 | 414.4 | 790.5 | 1243.8 | 1599.3 | 2066.5 |
| | Line 3 | 412.9 | 783.8 | 1273.0 | 1634.3 | 1972.1 |
| | Line 5 | 418.8 | 781.3 | 1266.2 | 1611.2 | 1918.3 |
| | Line 6 | 433.9 | 776.2 | 1265.5 | 1615.9 | 1919.7 |
| | Line 8 | 376.3 | 715.0 | 1222.3 | 1447.8 | 1840.5 |
| | Line 10 | 370.4 | 742.6 | 1250.7 | 1517.2 | 1906.9 |
| | Line 11 | 411.1 | 802.6 | 1336.5 | 1617.4 | 1951.8 |
| | Average | 403.0 | 772.1 | 1268.7 | 1584.4 | 1933.4 |

As is apparent from Table 3, in the strain into which the NoTRTRX gene was introduced (hereinafter, also referred to as "NoTRTRX strain"), fatty acid productivity was tend to increase compared to that in the wild-type strain. From the result, it indicated that lipid productivity is improved by enhancing expression of the NoTRTRX gene.

Example 2

Re-Culturing of NoTRTRX Strain Line 11, and Analysis of Lipids

The wild type strain and NoTRTRX strain line 11 were subjected again to preceding culture, pre-culture, and main culture by using methods in a manner similar to Example 1. In addition, regarding the light intensity, culturing was carried out under two conditions, namely, normal light conditions (100 μmol/m$^2$/s) and high light conditions (300 μmol/m$^2$/s) (preceding culture was carried out under the normal light conditions only, and pre-culture and main culture were carried out under the two conditions). The results of culturing under the normal light conditions are shown in Table 4, and the results of culturing under high light conditions are shown in Table 5. In addition, the total fatty acid amount ("TFA yield" in the tables) was indicated in the form of average value±standard deviation. The days described in Tables 4 and 5 indicate culturing days, and "TFA yield" indicates total fatty acid amount.

TABLE 4

| (100 μmol/m$^2$/s) (N = 2) | | | | | |
|---|---|---|---|---|---|
| TEA yield (mg/L) | | | | | |
| | 7 days | 10 days | 14 days | 17 days | 21 days |
| WT | 510.9 ± 12.8 | 865.8 ± 23.0 | 1347.1 ± 8.3 | 1652.8 ± 33.8 | 2013.0 ± 57.5 |
| TRTRX | 563.9 ± 8.3 | 983.0 ± 52.9 | 1557.8 ± 30.4 | 1920.3 ± 23.3 | 2319.9 ± 9.0 |

TABLE 5

| (300 μmol/m$^2$/s) (N = 2) | | | | | |
|---|---|---|---|---|---|
| TEA yield (mg/L) | | | | | |
| | 7 days | 10 days | 14 days | 17 days | 21 days |
| WT | 889.6 ± 16.6 | 1262.3 ± 37.1 | 1599.2 ± 124.3 | 1791.2 ± 38.7 | 2009.3 ± 87.4 |
| TRTRX | 1065.1 ± 30.1 | 1560.5 ± 51.5 | 2092.2 ± 72.4 | 2281.4 ± 48.9 | 2583.0 ± 41.6 |

As is apparent from Tables 4 and 5, it was shown that fatty acid productivity in NoTRTRX strain line 11 was largely improved as compared with that in the wild-type strain. Further, the effect of improving productivity was more significant in the high light conditions.

Example 3

Preparation of transformant of *Nannochloropsis* into which TAG synthetic pathway, fatty acid (FA) synthetic pathway, CBB cycle gene, and NoTRTRX gene were introduced, and Production of lipids by transformant 1. Construction of a Plasmid for TAG Synthetic Pathway Genes (DGAT and LACS Genes) Expression Using the cDNA derived from *Nannochloropsis oceanica* strain NIES-2145 prepared in 2. of Example 1 as a template, and a pair of the primers set forth in SEQ ID NO: 71 and SEQ ID NO: 72 shown in Table 2, PCR was carried out to amplify a LACS gene (nucleotide sequence: SEQ ID NO: 36, amino acid sequence: SEQ ID NO: 35) fragment. By a method in a manner similar to that in 2. of Example 1, a plasmid for LACS gene expression was constructed by using the amplified fragments. Herein, the plasmid consisted of the pUC19 vector sequence and an insert sequence in which the LDSP promoter sequence, the LACS gene, the VCP1 terminator sequence, the tubulin promoter sequence, the zeocin resistance gene and the heat shock protein terminator sequence were linked in this order.

Using the cDNA derived from *Nannochloropsis oceanica* strain NIES-2145 as a template, and a pair of the primers set forth in SEQ ID NO: 69 and SEQ ID NO: 70 shown in Table 2, PCR was carried out to obtain a DGAT gene (nucleotide sequence: SEQ ID NO: 34, amino acid sequence: SEQ ID NO: 33) fragment. Further, using a genomic DNA of *Nannochloropsis oceanica* strain NIES-2145 prepared in 1. of Example 1 as a template, and a pair of the primers set forth in SEQ ID NO: 52 and SEQ ID NO: 53, and a pair of the primers set forth in SEQ ID NO: 54 and SEQ ID NO: 55 shown in Table 2, PCRs were carried out to obtain a GS promoter sequence fragment (SEQ ID NO: 42) and a LDSP terminator sequence fragment (SEQ ID NO: 43), respectively. Furthermore, using the plasmid for LACS gene expression as a template, and a pair of the primers set forth in SEQ ID NO: 17 shown in Table 1 and SEQ ID NO: 56 shown in Table 2, PCR was carried out to amplify a fragment (a plasmid fragment for LACS gene expression) containing the cassette for LACS gene expression (the LDSP promoter sequence, the LACS gene, and the VCP1 terminator sequence), the cassette for zeocin resistance gene expression (the tubulin promoter sequence, the zeocin resistance gene, and the heat shock protein terminator sequence) and the pUC19 sequence.

The DGAT gene fragment, the GS promoter sequence fragment, the LDSP terminator sequence fragment, and the fragment of the plasmid for LACS gene expression were fused by a method in a manner similar to that described above, and thereby a plasmid for TAG synthetic pathway gene (the DGAT gene and the LACS gene) expression was constructed. Herein, the expression plasmid consisted of the pUC19 vector sequence and an insert sequence in which the GS promoter sequence, the DGAT gene, the LDSP terminator sequence, the LDSP promoter sequence, the LACS gene, the VCP1 terminator sequence, the tubulin promoter sequence, the zeocin resistance gene and the heat shock protein terminator sequence were linked in this order.

2. Construction of Plasmid for Fatty Acid (FA) Synthetic Pathway Gene (TE Gene)

Using the cDNA derived from *Nannochloropsis oceanica* strain NIES-2145 prepared in 2. of Example 1 as a template, and a pair of the primers set forth in SEQ ID NO: 73 and SEQ ID NO: 74 shown in Table 2, PCR was carried out to amplify a TE gene (nucleotide sequence: SEQ ID NO: 38, amino acid sequence: SEQ ID NO: 37) fragment. By a method in a manner similar to that in 2. of Example 1, a plasmid for TE gene expression (zeocin resistance) was constructed by using the amplified fragment. Herein, the plasmid consisted of the pUC19 vector sequence and an insert sequence in which the LDSP promoter sequence, the TE gene, the VCP1 terminator sequence, the tubulin promoter sequence, the zeocin resistance gene and the heat shock protein terminator sequence were linked in this order.

Using thus-constructed plasmid for TE gene expression (zeocin resistance) as a template, and a pair of the primers set forth in SEQ ID NO: 13 and SEQ ID NO: 14 shown in Table 1, PCR was carried out to amplify a fragment of the plasmid for TE gene expression. Further, a paromomycin resistance gene (SEQ ID NO: 39) was artificially synthesized. Using thus-synthesized DNA fragment of the paromomycin resistance gene as a template, and a pair of the primers set forth in SEQ ID NO: 46 and SEQ ID NO: 47 shown in Table 2, PCR was carried out to amplify a fragment of the paromomycin resistance gene. These two fragments were fused by a method in a manner similar to that in Example 1, thereby a plasmid for TE gene expression (paromomycin resistance) was constructed. Herein, the expression plasmid consisted of the pUC19 vector sequence and an insert sequence in which the LDSP promoter sequence, the TE gene, the VCP1 terminator sequence, the tubulin promoter sequence, the paromomycin resistance gene and the heat shock protein terminator sequence were linked in this order.

3. Construction of Plasmid for CBB Cycle Gene (RPI, TK, and FBA Gene) Expression Using the cDNA derived from *Nannochloropsis oceanica* strain NIES-2145 prepared in 2. of Example 1 as a template, and a pair of the primers set forth in SEQ ID NO: 65 and SEQ ID NO: 66, and a pair of the primers set forth in SEQ ID NO: 63 and SEQ ID NO: 64 shown in Table 2, PCRs were carried out to amplify a TK gene (nucleotide sequence: SEQ ID NO: 28, amino acid sequence: SEQ ID NO: 27) fragment and a FBA gene (nucleotide sequence: SEQ ID NO: 30, amino acid sequence: SEQ ID NO: 29) fragment. By a method in a manner similar to that in 1. of Example 3, a plasmid for the TK gene and the FBA gene expression was constructed by using the amplified fragments. Herein, the plasmid consisted of the pUC19 vector sequence and an insert sequence in which the GS promoter sequence, the TK gene, the LDSP terminator sequence, the LDSP promoter sequence, the FBA gene, the VCP1 terminator sequence, the tubulin promoter sequence, the zeocin resistance gene and the heat shock protein terminator sequence were linked in this order.

Using the cDNA derived from *Nannochloropsis oceanica* strain NIES-2145 as a template, and a pair of the primers set forth in SEQ ID NO: 67 and SEQ ID NO: 68 shown in Table 2, PCR was carried out to obtain an RPI gene (nucleotide sequence: SEQ ID NO: 32, amino acid sequence: SEQ ID NO: 31) fragment. Further, using the genomic DNA of *Nannochloropsis oceanica* strain NIES-2145 prepared in 1. of Example 1 as a template, and a pair of the primers set forth in SEQ ID NO: 57 and SEQ ID NO: 58, and a pair of the primers set forth in SEQ ID NO: 59 and SEQ ID NO: 60 shown in Table 2, PCRs were carried out to obtain an AMT promoter sequence fragment (SEQ ID NO: 44) and a desaturase (DES) terminator sequence fragment (SEQ ID NO: 45), respectively. Furthermore, using the plasmid for TK gene and FBA gene expression as a template, and a pair of the primers set forth in SEQ ID NO: 17 shown in Table 1 and SEQ ID NO: 61 shown in Table 2, PCR was carried out to amplify a fragment (a fragment of the plasmid for TK gene and FBA gene expression) consisted of a cassette for TK gene expression (the GS promoter sequence, the TK gene, the LDSP terminator sequence), a cassette for FBA gene expression (the LDSP promoter sequence, the FBA gene, the VCP1 terminator sequence), a cassette for zeocin gene expression (the tubulin promoter sequence, the zeocin resistance gene, the heat shock protein terminator sequence), and pUC19 sequence.

The RPI gene fragment, the AMT promoter sequence fragment, DES terminator sequence fragment, and the fragment of the plasmid for TK gene and FBA gene expression were fused by a method in a manner similar to that described above, a plasmid (zeocin resistance) for CBB cycle gene (RPI gene, TK gene, FBA gene) expression was constructed. Herein, the expression plasmid consisted of the pUC19 vector sequence and an insert sequence in which the AMT promoter sequence, the RPI gene, the DES terminator sequence, the GS promoter sequence, the TK gene, the LDSP terminator sequence, the LDSP promoter sequence, the FBA gene, the VCP1 terminator sequence, the tubulin promoter sequence, the zeocin resistance gene and the heat shock protein terminator sequence were linked in this order.

Using thus-constructed plasmid for CBB cycle gene expression (zeocin resistance) as a template, and a pair of the primers set forth in SEQ ID NO: 13 and SEQ ID NO: 14 shown in Table 1, PCR was carried out to amplify a fragment of the plasmid for CBB cycle gene expression. Further, a hygromycin resistance gene (SEQ ID NO: 40) was artificially synthesized. Using thus-synthesized DNA fragment of the hygromycin resistance gene as a template, and a pair of the primers set forth in SEQ ID NO: 48 and SEQ ID NO: 49 shown in Table 2, PCR was carried out to amplify a hygromycin resistance gene fragment. These two fragments were fused by a method in a manner similar to that in Example 1, thereby a plasmid for CBB cycle gene expression (hygromycin resistance) was constructed. Herein, the expression plasmid consisted of the pUC19 vector sequence and an insert sequence in which the AMT promoter sequence, the RPI gene, the DES terminator sequence, the GS promoter sequence, the TK gene, the LDSP terminator sequence, the LDSP promoter sequence, the FBA gene, the VCP1 terminator sequence, the tubulin promoter sequence, the hygromycin resistance gene and the heat shock protein terminator sequence were linked in this order.

4. Preparation of Transformant of *Nannochloropsis* into which TAG Synthetic Pathway, FA Synthetic Pathway, and CBB Cycle Genes were Introduced, and Culturing the Transformant Using the plasmid for TAG synthetic pathway gene expression, the plasmid for FA synthetic pathway gene expression (paromomycin resistance), and the plasmid for CBB cycle gene expression (hygromycin resistance) as templates, and a pair of the primers set forth in SEQ ID NO: 24 shown in Table 1 and SEQ ID NO: 75 shown in Table 2, a pair of the primers set forth in SEQ ID NO: 24 and SEQ ID NO: 23 shown in Table 1, and a pair of the primers set forth in SEQ ID NO: 24 shown in Table 1 and SEQ ID NO: 62 shown in Table 2, PCRs were carried out to amplify a cassette for TAG synthetic pathway gene expression (the GS promoter sequence, the DGAT gene, the LDSP terminator sequence, the LDSP promoter sequence, the LACS gene, the VCP1 terminator sequence, the tubulin promoter sequence, the zeocin resistance gene, the heat shock protein terminator sequence), a cassette for FA synthetic pathway gene expression (the LDSP promoter sequence, the TE gene, the VCP1 terminator sequence, the tubulin promoter sequence, the paromomycin resistance gene, the heat shock protein terminator sequence), and a cassette for CBB cycle gene expression (the AMT promoter sequence, the RPI gene, the DES terminator sequence, the GS promoter sequence, the TK gene, the LDSP terminator sequence, the LDSP promoter sequence, the FBA gene, the VCP1 terminator sequence, the tubulin promoter sequence, the hygromycin resistance gene and the heat shock protein terminator sequence). Thus-obtained amplified fragments were purified by a method in a manner similar to that in 3. of Example 1.

Thus-purified the cassette for expression of TAG synthetic pathway gene was introduced into *Nannochloropsis oceanica* strain NIES-2145 by a method in a manner similar to that in 3. of Example 1, then a strain having anti-drug resistance was selected, thereby a transformant into which the cassette for expression of the TAG synthetic pathway gene was introduced (the TAG synthetic pathway gene transgenic strain) was prepared. Then, using thus-obtained TAG synthetic pathway gene transgenic strain as a host, and the cassette for expression of the FA synthetic pathway gene was introduced and a strain having anti-drug resistance was selected by a method in a manner similar to that described above, thereby a transformant into which the cassette for expression of the FA synthetic pathway gene was introduced (the TAG synthetic pathway gene/the FA synthetic pathway gene transgenic strain) was prepared. Further, using the TAG synthetic pathway gene/FA synthetic pathway gene transgenic strain as a host, and the cassette for expression of the CBB cycle gene was introduced and a strain having anti-drug resistance was selected by a method in a manner similar to that described above, thereby a transformant into which the cassette for expression of the CBB cycle gene was introduced (the TAG synthetic pathway gene/the FA synthetic pathway gene/the CBB cycle gene transgenic strain (hereinafter, also referred to as "TAG/FA/CBB transgenic strain")) was prepared. In addition, for the selection of the various transformants, zeocin at a final concentration of 2 μg/mL, paromomycin at a final concentration of 100 μg/mL, and hygromycin at a final concentration of 500 μg/mL were respectively used.

5. Construction of Plasmid for NoTRTRX Gene Expression (Bialaphos Resistance)

A bialaphos resistance gene (SEQ ID NO: 41) was artificially synthesized. Using thus-synthesized DNA fragment as a template, and a pair of the primers set forth in SEQ ID NO: 50 and SEQ ID NO: 51 shown in Table 2, PCR was carried out to amplify a bialaphos resistance gene fragment. Further, using the plasmid for NoTRTRX gene expression (zeocin resistance) prepared in 2. of Example 1, and a pair of the primers set forth in SEQ ID NO: 13 and SEQ ID NO: 14 shown in Table 1, PCR was carried out to amplify a plasmid fragment except for the zeocin resistance gene. These fragments were treated by restriction enzyme DpnI (manufactured by TOYOBO) respectively, and were purified using a High Pure PCR Product Purification Kit (manufactured by Roche Applied Science).

Thus-purified amplified fragments were fused by a method in a manner similar to that described above, a plasmid for NoTRTRX gene expression (bialaphos resistance) was constructed. Herein, the expression plasmid consisted of the pUC19 vector sequence and an insert sequence in which the LDSP promoter sequence, the NoTR-TRX gene, the VCP1 terminator sequence, the tubulin promoter sequence, the bialaphos resistance gene and the heat shock protein terminator sequence were linked in this order.

6. Introduction of Cassette for NoTRTRX Gene Expression (Bialaphos Resistance) into TAG/FA/CBB Transgenic Strain, Culturing the Transformant, Extraction of Lipid from Culture Fluid, and Analysis of Fatty Acids Contained Therein Using the plasmid for NoTRTRX gene expression (bialaphos resistance) as a template, and a pair of the primers set forth in SEQ ID NO: 23 and SEQ ID NO: 24 shown in Table 1, PCR was carried out to amplify a cassette for NoTRTRX gene expression (bialaphos resistance) (a DNA fragment consisting of the LDSP promoter sequence, the NoTRTRX gene, the VCP1 terminator sequence, the tubulin promoter sequence, the bialaphos resistance gene, and the heat shock protein terminator sequence).

Thus-obtained amplified fragments were purified by a method in a manner similar to that in 3. of Example 1, and it was introduced into the TAG/FA/CBB transgenic strain and a strain having anti-drug resistance was selected by a method in a manner similar to that in 4. of Example 3, thereby a TAG synthetic pathway gene/the FA synthetic pathway gene/the CBB cycle gene/the NoTRTRX gene transgenic strain (hereinafter, also referred to as "TAG/FA/CBB/TRTRX transgenic strain") was prepared. Note that, for the selection of the transformant, bialaphos at a final concentration of 750 μg/mL was used.

The TAG/FA/CBB/TRTRX transgenic strain thus obtained and the TAG/FA/CBB transgenic strain produced in 4. of Example 3 were cultured by a method in a manner similar to that in Example 2 (high light conditions), and extraction of lipids and analysis of constituent fatty acids were carried out by methods in a manner similar to that in Example 1. In addition, culturing of the TAG/FA/CBB transgenic strain was carried out with N=4, and culturing of the TAG/FA/CBB/TRTRX transgenic strain was carried out for independent two lines.

Table 6 shows the results. In the table below, the TAG/FA/CBB transgenic strain was described as "TAG/FA/CBB", and the TAG/FA/CBB/TRTRX transgenic strain was described as "TAG/FA/CBB/TRTRX". Furthermore, for the TAG/FA/CBB transgenic strain, the results were indicated in the form of average value±standard deviation, and for the TAG/FA/CBB/TRTRX transgenic strain, the respective results for the independent two lines (line 1 and line 2) were indicated.

TABLE 6

| | TFA yield (mg/L) | | |
|---|---|---|---|
| | 6 days | 9 days | 13 days |
| TAG/FA/CBB | 1042.6 ± 26.0 | 1559.5 ± 53.7 | 2243.4 ± 47.5 |
| TAG/FA/CBB/ TRTRX line1 | 1192.4 | 1896.5 | 2716.6 |
| TAG/FA/CBB/ TRTRX line2 | 1195.6 | 1915.5 | 2345.9 |

As is apparent from Table 6, in the transformant (TAG/FA/CBB/TRTRX transgenic strain) into which the NoTR-TRX gene was introduced in addition to the TAG synthetic pathway gene, the FA synthetic pathway gene, and the CBB cycle gene, fatty acid productivity was further improved as compared with that in the transformant into which only the TAG synthetic gene, the FA synthetic gene and the CBB cycle gene were introduced.

As described above, it can be obtained a transformant wherein lipid productivity is improved, by enhancing expression of a protein containing the TRX domain and the TR domain. Therefore, by using the transformant, a method of producing lipids which improves productivity of fatty acids or lipids containing the same as components can be provided.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2018-186684 filed in Japan on Oct. 1, 2018, which is entirely herein incorporated by reference.

What is claimed is:

1. A method of producing lipids in a *Nannochloropsis* host, comprising the steps of:
   (a) introducing a gene encoding a protein containing a thioredoxin domain and a thioredoxin reductase domain into a *Nannochloropsis* host,
   (b) culturing the host in a suitable culture medium and at a suitable temperature and,
   (c) expressing the gene encoding the thioredoxin domain and the thioredoxin reductase domain in the host during the culturing, thereby producing fatty acids or lipids containing the same as components,
   wherein the thioredoxin domain is a domain consisting of the following amino acid sequence (A) or (B), or the following amino acid sequence (C) or (D), and the thioredoxin reductase domain is a domain consisting of the following amino acid sequence (E) or (F), or the following amino acid sequence (G) or (H):
   (A) the amino acid sequence at positions 529 to 629 of the amino acid sequence set forth in SEQ ID NO: 1;
   (B) an amino acid sequence having 90% or more identity with the amino acid sequence (A), and constituting the thioredoxin domain having thioredoxin activity;
   (C) the amino acid sequence at positions 525 to 625 of the amino acid sequence set forth in SEQ ID NO: 3;
   (D) an amino acid sequence having 90% or more identity with the amino acid sequence (C), and constituting the thioredoxin domain having thioredoxin activity;
   (E) the amino acid sequence at positions 137 to 448 of the amino acid sequence set forth in SEQ ID NO: 1;
   (F) an amino acid sequence having 90% or more identity with the amino acid sequence (E), and constituting the thioredoxin reductase domain having thioredoxin reductase activity;
   (G) the amino acid sequence at positions 134 to 445 of the amino acid sequence set forth in SEQ ID NO: 3; and
   (H) an amino acid sequence having 90% or more identity with the amino acid sequence (G), and constituting the thioredoxin reductase domain having thioredoxin reductase activity.

2. A method of improving lipid productivity in a *Nannochloropsis* host, comprising
   (a) introducing a gene encoding a protein containing a thioredoxin domain and a thioredoxin reductase domain into a *Nannochloropsis* host,
   (b) culturing the *Nannochloropsis* host in a suitable culture medium and at a suitable temperature and,
   (c) expressing the gene encoding the thioredoxin domain and the thioredoxin reductase domain in the *Nannochloropsis* host during the culturing, thereby improving the lipid productivity of the *Nannochloropsis* host into which the gene has been introduced as compared to that of the *Nannochloropsis* host into which the gene has not been introduced,
   wherein the thioredoxin domain is a domain consisting of the following amino acid sequence (A) or (B), or the following amino acid sequence (C) or (D), and the thioredoxin reductase domain is a domain consisting of the following amino acid sequence (E) or (F), or the following amino acid sequence (G) or (H):
   (A) the amino acid sequence at positions 529 to 629 of the amino acid sequence set forth in SEQ ID NO: 1;
   (B) an amino acid sequence having 90% or more identity with the amino acid sequence (A), and constituting the thioredoxin domain having thioredoxin activity;
   (C) the amino acid sequence at positions 525 to 625 of the amino acid sequence set forth in SEQ ID NO: 3;
   (D) an amino acid sequence having 90% or more identity with the amino acid sequence (C), and constituting the thioredoxin domain having thioredoxin activity;
   (E) the amino acid sequence at positions 137 to 448 of the amino acid sequence set forth in SEQ ID NO: 1;
   (F) an amino acid sequence having 90% or more identity with the amino acid sequence (E), and constituting the thioredoxin reductase domain having thioredoxin reductase activity;
   (G) the amino acid sequence at positions 134 to 445 of the amino acid sequence set forth in SEQ ID NO: 3; and
   (H) an amino acid sequence having 90% or more identity with the amino acid sequence (G), and constituting the thioredoxin reductase domain having thioredoxin reductase activity.

3. The method according to claim 1, wherein the alga is an alga belonging to the genus *Nannochloropsis Nannochloropsis*.

4. The method according to claim 1, wherein the thioredoxin domain is a domain consisting of the following amino acid sequence (A) or (B), or the following amino acid sequence (C) or (D), and the thioredoxin reductase domain is a domain consisting of the following amino acid sequence (E) or (F), or the following amino acid sequence (G) or (H):
   (A) the amino acid sequence at positions 529 to 629 of the amino acid sequence set forth in SEQ ID NO: 1;
   (B) an amino acid sequence having 95% or more identity with the amino acid sequence (A), and constituting the thioredoxin domain having thioredoxin activity;
   (C) the amino acid sequence at positions 525 to 625 of the amino acid sequence set forth in SEQ ID NO: 3;

(D) an amino acid sequence having 95% or more identity with the amino acid sequence (C), and constituting the thioredoxin domain having thioredoxin activity;
(E) the amino acid sequence at positions 137 to 448 of the amino acid sequence set forth in SEQ ID NO: 1;
(F) an amino acid sequence having 95% or more identity with the amino acid sequence (E), and constituting the thioredoxin reductase domain having thioredoxin reductase activity;
(G) the amino acid sequence at positions 134 to 445 of the amino acid sequence set forth in SEQ ID NO: 3; and
(H) an amino acid sequence having 95% or more identity with the amino acid sequence (G), and constituting the thioredoxin reductase domain having thioredoxin reductase activity.

5. The method according to claim 1, wherein the protein having the thioredoxin domain and the thioredoxin reductase domain is any one of the proteins selected from the group consisting of the following proteins (I) to (L):
(I) a protein consisting of the amino acid sequence set forth in SEQ ID NO: 1;
(J) a protein consisting of an amino acid sequence having 95% or more identity with the amino acid sequence of the protein (I), and containing the thioredoxin domain and the thioredoxin reductase domain having thioredoxin activity and thioredoxin reductase activity;
(K) a protein consisting of the amino acid sequence set forth in SEQ ID NO: 3; and
(L) a protein consisting of an amino acid sequence having 95% or more identity with the amino acid sequence of the protein (K), and containing the thioredoxin domain and the thioredoxin reductase domain having thioredoxin activity and thioredoxin reductase activity.

6. The method according to claim 1, wherein expression of one kind or two or more kinds of proteins involved in triacylglycerol synthetic pathway, fatty acid synthetic pathway, or Calvin-Benson-Bassham cycle is enhanced.

7. The method according to claim 1, wherein expression of the following protein (O) or (P), any one selected from the group consisting of the following proteins (Q) to (T), the following protein (M) or (N), the following protein (U) or (V), the following protein (W) or (X), and the following protein (Y) or (Z) is enhanced:
(M) a protein consisting of the amino acid sequence set forth in SEQ ID NO: 37;
(N) a protein consisting of an amino acid sequence having 95% or more identity with the amino acid sequence of the protein (M), and having acyl-ACP thioesterase activity;
(O) a protein consisting of the amino acid sequence set forth in SEQ ID NO: 35;
(P) a protein consisting of an amino acid sequence having 95% or more identity with the amino acid sequence of the protein (O), and having acyl-CoA synthetase activity;
(Q) a protein consisting of the amino acid sequence set forth in SEQ ID NO: 33;
(R) a protein consisting of an amino acid sequence having 95% or more identity with the amino acid sequence of the protein (Q), and having acyltransferase activity;
(S) a protein consisting of the amino acid sequence set forth in SEQ ID NO: 76;
(T) a protein consisting of an amino acid sequence having 95% or more identity with the amino acid sequence of the protein (S), and having acyltransferase activity;
(U) a protein consisting of the amino acid sequence set forth in SEQ ID NO: 27;
(V) a protein consisting of an amino acid sequence having 95% or more identity with the amino acid sequence of the protein (U), and having transketolase activity;
(W) a protein consisting of the amino acid sequence set forth in SEQ ID NO: 29;
(X) a protein consisting of an amino acid sequence having 95% or more identity with the amino acid sequence of the protein (W), and having fructose-1,6-bisphosphate aldolase activity;
(Y) a protein consisting of the amino acid sequence set forth in SEQ ID NO: 31; and
(Z) a protein consisting of an amino acid sequence having 95% or more identity with the amino acid sequence of the protein (Y), and having ribose-5-phosphate isomerase activity.

8. A transformant of an alga, wherein the transformant comprises a gene encoding a protein containing a thioredoxin domain and a thioredoxin reductase domain that has been introduced into the transformant, thereby enhancing expression of the gene in the transformant.

9. The transformant according to claim 8, wherein the alga is an alga belonging to the genus *Nannochloropsis*.

10. The transformant according to claim 8, wherein the thioredoxin domain is a domain consisting of the following amino acid sequence (A) or (B), or the following amino acid sequence (C) or (D), and the thioredoxin reductase domain is a domain consisting of the following amino acid sequence (E) or (F), or the following amino acid sequence (G) or (H):
(A) the amino acid sequence at positions 529 to 629 of the amino acid sequence set forth in SEQ ID NO: 1;
(B) an amino acid sequence having 95% or more identity with the amino acid sequence (A), and constituting the thioredoxin domain having thioredoxin activity;
(C) the amino acid sequence at positions 525 to 625 of the amino acid sequence set forth in SEQ ID NO: 3;
(D) an amino acid sequence having 95% or more identity with the amino acid sequence (C), and constituting the thioredoxin domain having thioredoxin activity;
(E) the amino acid sequence at positions 137 to 448 of the amino acid sequence set forth in SEQ ID NO: 1;
(F) an amino acid sequence having 95% or more identity with the amino acid sequence (E), and constituting the thioredoxin reductase domain having thioredoxin reductase activity;
(G) the amino acid sequence at positions 134 to 445 of the amino acid sequence set forth in SEQ ID NO: 3; and
(H) an amino acid sequence having 95% or more identity with the amino acid sequence (G), and constituting the thioredoxin reductase domain having thioredoxin reductase activity.

11. The transformant according to claim 8, wherein the protein having the thioredoxin domain and the thioredoxin reductase domain is any one of the proteins selected from the group consisting of the following proteins (I) to (L):
(I) a protein consisting of the amino acid sequence set forth in SEQ ID NO: 1;
(J) a protein consisting of an amino acid sequence having 95% or more identity with the amino acid sequence of the protein (I), and containing the thioredoxin domain and the thioredoxin reductase domain having thioredoxin activity and thioredoxin reductase activity;
(K) a protein consisting of the amino acid sequence set forth in SEQ ID NO: 3; and
(L) a protein consisting of an amino acid sequence having 95% or more identity with the amino acid sequence of the protein (K), and containing the thioredoxin domain and the thioredoxin reductase domain having thioredoxin activity and thioredoxin reductase activity.

12. The transformant according to claim 8, wherein expression of one kind or two or more kinds of proteins involved in triacylglycerol synthetic pathway, fatty acid synthetic pathway, or Calvin-Benson-Bassham cycle is enhanced.

13. The transformant according to claim 8, wherein expression of the following protein (O) or (P), any one selected from the group consisting of the following proteins (Q) to (T), the following protein (M) or (N), the following protein (U) or (V), the following protein (W) or (X), and the following protein (Y) or (Z) is enhanced:
 (M) a protein consisting of the amino acid sequence set forth in SEQ ID NO: 37;
 (N) a protein consisting of an amino acid sequence having 95% or more identity with the amino acid sequence of the protein (M), and having acyl-ACP thioesterase activity;
 (O) a protein consisting of the amino acid sequence set forth in SEQ ID NO: 35;
 (P) a protein consisting of an amino acid sequence having 95% or more identity with the amino acid sequence of the protein (O), and having acyl-CoA synthetase activity;
 (Q) a protein consisting of the amino acid sequence set forth in SEQ ID NO: 33;
 (R) a protein consisting of an amino acid sequence having 95% or more identity with the amino acid sequence of the protein (Q), and having acyltransferase activity;
 (S) a protein consisting of the amino acid sequence set forth in SEQ ID NO: 76;
 (T) a protein consisting of an amino acid sequence having 95% or more identity with the amino acid sequence of the protein (S), and having acyltransferase activity;
 (U) a protein consisting of the amino acid sequence set forth in SEQ ID NO: 27;
 (V) a protein consisting of an amino acid sequence having 95% or more identity with the amino acid sequence of the protein (U), and having transketolase activity;
 (W) a protein consisting of the amino acid sequence set forth in SEQ ID NO: 29;
 (X) a protein consisting of an amino acid sequence having 95% or more identity with the amino acid sequence of the protein (W), and having fructose-1,6-bisphosphate aldolase activity;
 (Y) a protein consisting of the amino acid sequence set forth in SEQ ID NO: 31; and
 (Z) a protein consisting of an amino acid sequence having 95% or more identity with the amino acid sequence of the protein (Y), and having ribose-5-phosphate isomerase activity.

14. The method according to claim 2, wherein the alga is *Nannochloropsis* oceanica.

15. The method according to claim 2, wherein the thioredoxin domain is a domain consisting of the following amino acid sequence (A) or (B), or the following amino acid sequence (C) or (D), and the thioredoxin reductase domain is a domain consisting of the following amino acid sequence (E) or (F), or the following amino acid sequence (G) or (H):
 (A) the amino acid sequence at positions 529 to 629 of the amino acid sequence set forth in SEQ ID NO: 1;
 (B) an amino acid sequence having 95% or more identity with the amino acid sequence (A), and constituting the thioredoxin domain having thioredoxin activity;
 (C) the amino acid sequence at positions 525 to 625 of the amino acid sequence set forth in SEQ ID NO: 3;
 (D) an amino acid sequence having 95% or more identity with the amino acid sequence (C), and constituting the thioredoxin domain having thioredoxin activity;
 (E) the amino acid sequence at positions 137 to 448 of the amino acid sequence set forth in SEQ ID NO: 1;
 (F) an amino acid sequence having 95% or more identity with the amino acid sequence (E), and constituting the thioredoxin reductase domain having thioredoxin reductase activity;
 (G) the amino acid sequence at positions 134 to 445 of the amino acid sequence set forth in SEQ ID NO: 3; and
 (H) an amino acid sequence having 95% or more identity with the amino acid sequence (G), and constituting the thioredoxin reductase domain having thioredoxin reductase activity.

16. The method according to claim 2, wherein the protein having the thioredoxin domain and the thioredoxin reductase domain is any one of the proteins selected from the group consisting of the following proteins (I) to (L):
 (I) a protein consisting of the amino acid sequence set forth in SEQ ID NO: 1;
 (J) a protein consisting of an amino acid sequence having 90% or more identity with the amino acid sequence of the protein (I), and containing the thioredoxin domain and the thioredoxin reductase domain having thioredoxin activity and thioredoxin reductase activity;
 (K) a protein consisting of the amino acid sequence set forth in SEQ ID NO: 3; and
 (L) a protein consisting of an amino acid sequence having 90% or more identity with the amino acid sequence of the protein (K), and containing the thioredoxin domain and the thioredoxin reductase domain having thioredoxin activity and thioredoxin reductase activity.

17. The method according to claim 2, wherein expression of one kind or two or more kinds of proteins involved in triacylglycerol synthetic pathway, fatty acid synthetic pathway, or Calvin-Benson-Bassham cycle is enhanced.

18. The method according to claim 2, wherein expression of the following protein (O) or (P), any one selected from the group consisting of the following proteins (Q) to (T), the following protein (M) or (N), the following protein (U) or (V), the following protein (W) or (X), and the following protein (Y) or (Z) is enhanced:
 (M) a protein consisting of the amino acid sequence set forth in SEQ ID NO: 37;
 (N) a protein consisting of an amino acid sequence having 90% or more identity with the amino acid sequence of the protein (M), and having acyl-ACP thioesterase activity;
 (O) a protein consisting of the amino acid sequence set forth in SEQ ID NO: 35;
 (P) a protein consisting of an amino acid sequence having 90% or more identity with the amino acid sequence of the protein (O), and having acyl-CoA synthetase activity;
 (Q) a protein consisting of the amino acid sequence set forth in SEQ ID NO: 33;
 (R) a protein consisting of an amino acid sequence having 90% or more identity with the amino acid sequence of the protein (Q), and having acyltransferase activity;
 (S) a protein consisting of the amino acid sequence set forth in SEQ ID NO: 76;
 (T) a protein consisting of an amino acid sequence having 90% or more identity with the amino acid sequence of the protein (S), and having acyltransferase activity;
 (U) a protein consisting of the amino acid sequence set forth in SEQ ID NO: 27;

(V) a protein consisting of an amino acid sequence having 90% or more identity with the amino acid sequence of the protein (U), and having transketolase activity;
(W) a protein consisting of the amino acid sequence set forth in SEQ ID NO: 29;
(X) a protein consisting of an amino acid sequence having 90% or more identity with the amino acid sequence of the protein (W), and having fructose-1,6-bisphosphate aldolase activity;
(Y) a protein consisting of the amino acid sequence set forth in SEQ ID NO: 31; and
(Z) a protein consisting of an amino acid sequence having 90% or more identity with the amino acid sequence of the protein (Y), and having ribose-5-phosphate isomerase activity.

* * * * *

```
                             SEQUENCE LISTING

<160> NUMBER OF SEQ ID NOS: 77

<210> SEQ ID NO 1
<211> LENGTH: 635
<212> TYPE: PRT
<213> ORGANISM: Nannochloropsis oceanica

<400> SEQUENCE: 1

Met Ala Asn Thr Arg His Thr Asn Ser Ser Arg Cys Ser Lys Leu His
1               5                   10                  15

Leu His Ile Val His Phe Thr Leu Leu Ala Ile Leu Pro Leu Leu Leu
                20                  25                  30

Ser Ala Ala Ala Ser Ala Arg Val Ser Ser Arg Ser Phe Arg Gln Gln
            35                  40                  45

Thr Arg Glu Tyr Ser Ser Val Gly Phe Leu Val Pro Tyr Leu Gln Ser
        50                  55                  60

Ser Arg Ser Thr His His Ser Ser Ser Ser Pro Ala Ala Ala Ser Ser
65                  70                  75                  80

Ser Ser Ser Ser Ser Ser Pro Phe Ser Phe Ser Ser Ser Pro Phe Ser
                85                  90                  95

Ser Phe Ser Phe Gln Arg Gly Gln Gln Glu Gln Gln Gln Ala Thr Arg
                100                 105                 110

Arg Phe Phe Leu Pro Ser Leu Arg Ala Ser Gly Ser Asp Ala Pro Thr
            115                 120                 125

Thr Thr His Glu Glu Val Glu Asn Val Ile Ile Ile Gly Ser Gly Pro
130                 135                 140

Ala Gly Tyr Thr Ala Ala Ile Tyr Ser Ala Arg Ala Asn Leu Lys Pro
145                 150                 155                 160

Val Ile Phe Glu Gly Thr Ser Ser Thr Gly Gly Gln Leu Met Ala Thr
                165                 170                 175

Thr Asp Val Glu Asn Phe Pro Gly Phe Pro Glu Gly Ile Leu Gly Pro
                180                 185                 190

Asp Leu Met Met Asn Met Arg Lys Gln Ala Ala Arg Trp Gly Ala Glu
            195                 200                 205

Leu Glu Ser Asp Asp Val Ile Ala Val Asp Leu Gln Ser Arg Pro Phe
        210                 215                 220

His Val Lys Ser Ala Gly Gly Arg Asn Leu Lys Thr His Ser Ile Ile
225                 230                 235                 240

Ile Ala Thr Gly Ala Val Ala Lys Arg Leu Asn Leu Pro Asn Glu Val
                245                 250                 255

Lys Tyr Trp Ser Lys Gly Val Thr Ala Cys Ala Ile Cys Asp Gly Ala
                260                 265                 270

Ala Pro Met Phe Ser Gly Glu Pro Leu Ala Val Val Gly Gly Gly Asp
            275                 280                 285

Ser Ala Ala Glu Glu Ala Val Tyr Leu Thr Lys Tyr Ser Pro Gln Ile
        290                 295                 300
```

His Leu Leu Val Arg Gly Ser Ser Met Arg Ala Ser Lys Ala Leu Gln
305                 310                 315                 320

Asp Arg Val Leu Gly Asn Lys Lys Ile Thr Val His Tyr Asn Thr Gln
                325                 330                 335

Val Leu Asp Val Met Gly Asp Asp Pro Asp Leu Pro Phe Thr Lys Ser
            340                 345                 350

Pro Val Thr Gly Val Lys Ile Ala Pro Val Ser Glu Gly Ala Lys Gly
        355                 360                 365

Ala Arg Glu Leu Ala Val Arg Gly Leu Phe Tyr Ala Ile Gly His Asp
370                 375                 380

Pro Asn Thr Ser Leu Phe Glu Ala Phe Leu Asp Ile Asp Lys Lys Gly
385                 390                 395                 400

Tyr Val Thr Val Gln Pro Gly Thr Pro Ser Thr Ser Leu Glu Gly Val
                405                 410                 415

Phe Ala Ala Gly Asp Val Gln Asp Pro His Trp Arg Gln Ala Val Thr
            420                 425                 430

Ala Ala Gly Ser Gly Cys Met Ala Ala Leu Ala Ala Glu Arg Tyr Leu
        435                 440                 445

Ser Val Arg Gly Leu Val Arg Glu Val His Gln Pro Lys Glu Glu Glu
450                 455                 460

Glu Lys Val Val Ala Ala Pro Ala Thr Val Ser Ala Ala Gly Gly Asn
465                 470                 475                 480

Gly Ala Ser Ser Ser Gly Ser Ser Ser Ser Ser Ser Ser Ser Ser Ser
                485                 490                 495

Thr Ser Ser Gly Ser Thr Ser Ser Gly Gly Asn Ser Glu Gly Val Gln
            500                 505                 510

Ser Met Ala Leu Leu Ala Glu Ser Asp Gln Ser Asn Thr Tyr His Lys
        515                 520                 525

Gly Glu Ala Ala Leu Ser Glu Leu Leu Ala Ser Ser Ser Lys Pro Ile
530                 535                 540

Leu Val Met Phe Met Ser Lys Thr Cys Gly Pro Cys Arg Ile Leu Lys
545                 550                 555                 560

Pro Ile Leu Gly Arg Val Leu Lys Glu Phe Glu Gly Gln Val His Phe
                565                 570                 575

Val Glu Ile Asp Ile Glu Glu Tyr Pro Asp Leu Thr Met Gln Ser Ser
            580                 585                 590

Val Ala Gly Thr Pro Thr Val Gln Val Met Asn Leu Lys Asn Arg Ala
        595                 600                 605

Glu Gly Glu Glu Val Ile Thr Leu Arg Gly Val Lys Lys Gly Ser Glu
610                 615                 620

Tyr Lys Ser Gln Ile Ile Glu Ala Leu Asp Met
625                 630                 635

<210> SEQ ID NO 2
<211> LENGTH: 1908
<212> TYPE: DNA
<213> ORGANISM: Nannochloropsis oceanica

<400> SEQUENCE: 2
atggctaata cccgccacac caacagcagc agatgcagca agctccatct ccatatagtc      60
cactttactc ttctcgccat cctgcccctc ctcctttccg ctgcagctag cgcccgtgtc     120
agttctcggt cattccgaca gcaaacaagg gaatattcct ccgtaggttt ccttgtcccg     180
tacttgcaat cctcccgcag tacccaccac tcctcatcat cacccgcagc cgcttcctcc     240

-continued

```
tcctcctcct cctcctcccc cttttccttc tcctcctccc ccttctcctc cttctctttc      300
cagcgaggac agcaggagca acagcaggca acaaggcgtt tcttcttacc atcacttcgg      360
gccagcggca gcgatgcacc aacgaccaca catgaggaag tggagaacgt tataattatc      420
ggttcaggtc cggccgggta caccgctgcc atctactctg cgcgtgctaa cctcaagcct      480
gttatttttg aaggcacatc ttcgacagga gggcagctta tggcgacgac ggacgtcgag      540
aatttccctg gctttcctga ggggatcttg gaccagatt tgatgatgaa catgaggaaa       600
caagctgccc ggtgggggc cgagctcgag agcgacgacg tcatcgctgt ggatctacag       660
tcccgtcctt ttcatgtcaa gagtgccggg ggtcgaaatc tgaaaacgca ttccatcatc      720
attgcaacgg gggccgtggc gaaacggttg aacctcccca acgaggttaa gtattggtcg      780
aaaggtgtaa cggcctgcgc catctgtgat ggcgccgcgc ccatgttcag tggagaaccg      840
ctcgcagttg ttggggggg ggatagtgct gcggaagagg ctgtgtattt gactaaatac       900
tcgccgcaga ttcatttgtt ggtccgaggg tcaagtatgc gcgcgtccaa agcgctccag      960
gaccgggtat tggggaacaa gaagattact gtccattaca acacgcaggt actcgacgtt     1020
atgggcgatg atccagacct tccatttacg aagagtcccg tcacgggcgt gaagatcgcg     1080
ccggtttccg agggggccaa ggggggccagg gagttggcgg ttcgaggcct tttttacgca    1140
atcgggcatg atcccaacac gagcttgttc gaagccttcc tggacataga taagaaaggg     1200
tatgttaccg tgcagcctgg cacaccgtcg acgtctctgg agggcgtgtt tgccgcggga     1260
gacgtccagg acccgcattg gcgccaggcg gtgaccgcag caggctcggg atgtatggcg     1320
gcattggccg cagagaggta cttgtctgtg agaggcttag tgcgtgaagt gcaccagccg     1380
aaagaggagg aggagaaggt ggtggcggcg cctgcgactg tttctgcagc gggtggaaat     1440
ggggcatcaa gcagtggtag cagtagcagt agcagtagca gcagtagcac tagcagcggt     1500
agcactagca gcggtggtaa tagtgaggga gtccagagca tggccttgct ggctgagagc     1560
gaccagagca ataccctacca taagggagag gcggcgctgt cggagctgct ggcatcgagc     1620
agcaagccca ttttggtgat gtttatgagt aagacctgtg accctgccg gatcttgaaa      1680
ccgatccttg ggagggttct gaaggaattt gaagggcaag tgcacttcgt cgagattgac     1740
attgaggagt accctgacct gactatgcag tcgtctgtgg ctggaactcc cactgtgcag     1800
gtcatgaatt tgaagaacag gcggagggc gaggaggtga taaccttgcg ggggggtgaag    1860
aaggggagtg agtacaaatc gcaaattata gaagccttgg atatgtga                  1908
```

<210> SEQ ID NO 3
<211> LENGTH: 633
<212> TYPE: PRT
<213> ORGANISM: Nannochloropsis gaditana

<400> SEQUENCE: 3

```
Met Val Lys Phe Ile Phe Leu Ser Ile Ser Leu Ala Leu Phe Leu His
1               5                   10                  15

His His Ala Tyr Val Asp Ala Arg His Asn Phe His Arg Phe Val Glu
                20                  25                  30

Gln Arg Asp Arg Ser Ala Gly Phe Leu Gly Ile His Arg Gln Ile Leu
            35                  40                  45

Arg Gly Ala Gly Arg Pro Ser Ser Phe Pro Val Ser Leu Pro Thr Met
        50                  55                  60

Ser Pro Thr Ser Thr Pro Pro Thr Pro Leu Ser Thr Tyr Tyr Leu Ser
65                  70                  75                  80
```

```
Pro Ser Pro Thr Ser Ser Lys Phe Cys Pro Ser Ser Cys Gly Val Gly
                85                  90                  95

Leu Phe His Ala Leu Arg His Leu Pro Gln Pro Thr Arg Ile Ser Phe
            100                 105                 110

Pro Leu Trp Ala Thr Ala Ala Glu Leu Ala Gly Asp Leu Thr Ala Asp
        115                 120                 125

Lys Ala Ala Glu Asn Val Val Ile Val Gly Ser Gly Pro Ala Gly Tyr
    130                 135                 140

Thr Ala Ala Ile Tyr Cys Ala Arg Ala Asn Leu Lys Pro Val Ile Phe
145                 150                 155                 160

Glu Gly Ala Ser Ser Thr Gly Gly Gln Leu Met Ala Thr Thr Asp Val
                165                 170                 175

Glu Asn Phe Pro Gly Phe Pro Asp Gly Ile Leu Gly Pro Asp Leu Met
            180                 185                 190

Met Asn Met Arg Lys Gln Ala Ala Arg Trp Gly Ala Glu Leu Glu Ser
        195                 200                 205

Asp Asp Val Val Ser Val Asp Leu Ser Ser Arg Pro Phe Ser Val Thr
    210                 215                 220

Gly Ala Asn Gly Arg Cys Val Thr Ala His Ser Val Ile Ile Ala Thr
225                 230                 235                 240

Gly Ala Val Ala Lys Arg Leu Arg Leu Pro Asn Glu Glu Arg Tyr Trp
                245                 250                 255

Ser Lys Gly Ile Thr Ala Cys Ala Ile Cys Asp Gly Ala Ala Pro Met
            260                 265                 270

Phe Ser Gly Glu Pro Leu Ala Val Gly Gly Gly Asp Ser Ala Ala
        275                 280                 285

Glu Glu Ala Val Tyr Leu Thr Lys Tyr Ser Pro Glu Ile His Leu Leu
    290                 295                 300

Val Arg Gly Glu Ser Met Arg Ala Ser Arg Ala Leu Gln Asp Arg Val
305                 310                 315                 320

Leu Ala Asn Arg Lys Ile Leu Val His Tyr Asn Thr Arg Val Val Asp
                325                 330                 335

Val Leu Gly Asp Asp Pro Glu Val Pro Phe Leu Lys Ser Pro Val Thr
            340                 345                 350

Ala Val Gln Val Ala Thr Thr Glu Gly Lys Thr Glu Val Met Lys Ser
        355                 360                 365

Leu Ala Val Arg Gly Leu Phe Tyr Ala Ile Gly His Asp Pro Asn Thr
    370                 375                 380

Ala Leu Phe Ala Gln Phe Leu Asp Val Asp Glu Lys Gly Tyr Val Arg
385                 390                 395                 400

Val Ala Pro Gly Thr Pro Thr Thr Ser Leu Ser Gly Val Phe Ala Ala
                405                 410                 415

Gly Asp Val Gln Asp Pro His Trp Arg Gln Ala Val Thr Ala Ala Gly
            420                 425                 430

Ser Gly Cys Met Ala Ala Leu Ala Glu Arg Tyr Leu Ser Gly Glu
        435                 440                 445

Gly Leu Leu Arg Glu Val His Gln Pro Lys Asp Val Glu Arg Lys
    450                 455                 460

Lys Gly Ala Gly Asp Arg Gly Gly Glu Lys Ala Val Gln Glu Pro Gly
465                 470                 475                 480

Glu Lys Gln Thr Glu Ala Thr Ala Ile Pro Ser Asp Arg Asn Ser Gly
                485                 490                 495
```

```
Ser Gly Ser Arg Gly Gly Ser Gly Thr Gly Met Arg Ser Leu Ala Ala
            500                 505                 510
Ala Ala Glu Asp Asp Ala Thr Asp Thr Tyr His Lys Gly Glu Ala Ala
            515                 520                 525
Leu Gln Ser Leu Leu Ala Ser Ser Gly Lys Pro Ile Leu Ile Met Phe
            530                 535                 540
Met Ser Lys Thr Cys Gly Pro Cys Arg Ile Leu Lys Pro Ile Leu Gly
545                 550                 555                 560
Arg Val Leu Lys Glu Tyr Glu Gly Arg Val His Phe Val Glu Ile Asp
                565                 570                 575
Ile Glu Glu His Pro Asp Leu Thr Leu Gln Ser Ser Val Ala Gly Thr
                580                 585                 590
Pro Thr Val Gln Leu Val Asn Leu Lys Asn Arg Ala Glu Gly Glu Glu
            595                 600                 605
Val Val Thr Leu Arg Gly Val Lys Lys Gly Ser Glu Tyr Lys Ala Gln
            610                 615                 620
Ile Glu Glu Ala Leu Gly Gly His Glu
625                 630

<210> SEQ ID NO 4
<211> LENGTH: 1902
<212> TYPE: DNA
<213> ORGANISM: Nannochloropsis gaditana

<400> SEQUENCE: 4
atggtcaagt tcattttctt gtccattttcc ctggcccttt tcctccacca tcacgcatat      60
gtcgatgctc gacataattt tcatcggttc gttgaacaac gtgaccgttc cgccggtttc     120
ctcggtatac accggcaaat tttaaggggt gcaggtcgcc cgtcttcatt tccagtctct     180
cttcccacca tgtcgccaac atcgactccg cccacgcccc tctctaccta ttacctctcc     240
ccctcgccaa cttcctccaa attctgccct tcctcttgtg cgtcggcctt gtttcatgct     300
ctgagacacc tccccagcc cacgcgcatt tccttccccc tctgggcaac cgccgcggag     360
ctggcgggag acctgacggc agataaggcg gctgagaatg tggtcatagt aggatcaggc     420
cctgcagggt acaccgccgc aatttattgc gctcgagcaa atttaaaacc cgtgatcttc     480
gagggcgcgt cctccaccgg gggacaattg atggccacca cggacgtgga aatttcccg     540 ggctttccgg acgggatatt ggaccagac ttgatgatga atatgaggaa caagcggcc     600 agatgggggg cggagctgga gagtgacgac gtggtaagcg tggacctgtc ttctcgccct     660
ttttccgtga cggggcgaa cggacggtgc gtgacgcgc attccgtcat tatcgccacg     720
ggggccgtgg ccaaacgcct ccggctcccg aacgaggaga ggtattggtc aaagggggatc     780 acggcgtgcg ccatctgcga cggcgccgcc cccatgttca gcgagaaacc cctggctgtg     840
gtgggggggg gagacagcgc ggccgaagag gcggtatacc tgaccaagta ctcgccggag     900
atccatcttt tggtccgagg ggagagcatg cgggcgtccc gggccctcca ggaccgggtg     960
ttggcgaaca ggaagatctt ggtgcattac aacacgcgcg tcgtggacgt gttgggcgac    1020
gacccggagg tgccccttcct gaagagcccc gtgaccgcgg tgcaagtggc cacgacggag    1080
gggaagacag aggtaatgaa gagcctggcg gtccgtggtt tgttctacgc catcggacac    1140 gaccccgaaca cggccttgtt cgcgcaattt ttggatgtgg acgagaaagg ctacgttcgt    1200
gtggcccccg gaacacccac cacctctttg tccggcgtct ttgcggcagg cgacgttcag    1260
gacccgcact ggcgccaggc cgtgaccgca gcgggctcag gctgcatggc tgccctggca    1320
```

```
gccgagaggt atctgtcggg ggaagggctg ctaagggaag tgcaccagcc taaggacgac    1380
gtggagagga aaaagggggc aggagacagg ggcggggaga aggcggtcca agagccggga    1440
gaaaagcaga cagaggccac tgccatacca agcgacagga acagtgggag tgggagtaga    1500
ggtgggagtg gcaccggcat gcgcagcctc gcggctgccg ccgaagacga cgccaccgac    1560
acataccaca agggagaggc ggccttgcag tccctcctgg cctcgagcgg caagcctatc    1620
ttgatcatgt tcatgagcaa gacttgcggg ccctgccgga tcctgaagcc gattcttggc    1680
cgggtgttga aggaatatga agggcgggtt cattttgtag aaatcgacat cgaggaacat    1740
ccagacctga cgttgcagtc ctccgtggcc gggaccccga ccgtgcagct ggtcaatctg    1800
aagaatcggg ccgaggggga ggaagtggtg actctgaggg gggtgaagaa ggggagcgag    1860
tacaaggcgc agatcgaaga ggcgctgggg gggcatgagt ga                      1902
```

<210> SEQ ID NO 5
<211> LENGTH: 375
<212> TYPE: DNA
<213> ORGANISM: Artificial Sequence
<220> FEATURE:
<223> OTHER INFORMATION: zeocin resistance gene

<400> SEQUENCE: 5

```
atggccaagc tgaccagcgc cgttccggtg ctcaccgcgc gcgacgtcgc cggagcggtc     60
gagttctgga ccgaccggct cgggttctcc cgggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300
ccgtgggggc gggagttcgc cctgcgcgac cggccggcca actgcgtgca cttcgtggcc    360
gaggagcagg actaa                                                    375
```

<210> SEQ ID NO 6
<211> LENGTH: 500
<212> TYPE: DNA
<213> ORGANISM: Nannochloropsis gaditana

<400> SEQUENCE: 6

```
actgcgcatg gattgaccga cggccggttg ccaacttttg gggtcggccc cccttttcta     60
gcccttgccc gtccagcaat taaaaattat caacggcata ccggcactgg aagcttcggg    120
tttacaattt tggcttgcct tcctaatact gtaccgcgga gaacgtatga tattacagaa    180
aaatgccttg cacagttagc gcaaagggaa aacgtttctc cgccattgta cttttttggaa    240 gagggaaagc gattgtaaaa tatggctctc cgctacgaga gtttgggctg ttgatacatg    300
tgaaaataag tgtggacgac tttgaatgac ttgatcaggc tgtttgcaca tataaccagc    360
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt ttgtgaagca                                                500
```

<210> SEQ ID NO 7
<211> LENGTH: 1000
<212> TYPE: DNA
<213> ORGANISM: Nannochloropsis oceanica

<400> SEQUENCE: 7

```
tcgggatggg ggaaaaaaac ctctgtgtgg gctgtcagtt gatactatta gaggtctttt     60
```

-continued

```
gttttgtttg tggctgcgtg tgtgtgtttg catgagaaat agacttgaga atatcggaag      120
gaactttgac atggtaaacg aggaaaagaa aatcttcaaa aaggaataat gggtaaaaac      180
aaggagcacc gggtctcttt agaaatgctt ctcggcggaa aaccagaaaa aaaggtagaa      240
tatgtcgact ttttcgctta tcattataga atgaaagatc gaatggccaa gggatttata      300
aattctttct ttatgttgtc gtagaactta cttccatcc cgagggaggt gtatgcaggc       360
caaaccctct gacatgggcg caatatctct atgaaaggtt gttggaatac attgtccgac      420
ctccttcgag gcggagccgc atagttgaag tataggtgct tgcttcatcc atctcatgac      480
gctttgccag tgactcactc atgcatgtga cacatttagt tctgctcgct caagcctggc      540
ccctcctgac atgcacacat tgcacttgta ggtgggccac gtttagtata cgccacc       600 ctgtcgcacc atcggtccca gagcaggagc acgcttccct actcctgtac gctcccctg       660 cttccccccc tgctcgtcaa cgatggcgac gccagcggct gcgaattaca gtgacggcgc      720
ggccgctcag gatgacagct cctctccttc aacatctccc aatcttccac cccgcccat       780 gtcgtcgttc gtacggccta tgctgaccga tatgtaccaa attacaatgg tcttcgcgta      840
ctggaagcaa aagcggcacc aggacagggc catctttgag ctcttttcc ggaagacacc       900 ctttaaggga gagtttgcca ttatggccgg cattgacgaa gtactcaagt acttggccca      960
ctttcgcttc tccgaggagg agctgattta tttacgaaag                             1000
```

<210> SEQ ID NO 8
<211> LENGTH: 800
<212> TYPE: DNA
<213> ORGANISM: Nannochloropsis oceanica

<400> SEQUENCE: 8

```
ttcttccgct tgttgctgcc gatggcggcc atggtctcta agatggagtg gatggaggag       60
gaggcgagcg tagcagcaag cgtgagttat acagccaggc acatgtcgca atccttcggt      120
ctcgggctta aaatccacgc actaatcacg ctgggccatg caaagagcaa tgccgaggcc      180
caccacacaa aacgctgtgt cgcgcgttgc ggcctgaagc ttcatacttc ttagtcgccg      240
ccaaaagggc tcgagagacg agaccgttg gcatgaccga tgttgttcga cgcggtttgc       300
ttcgtcacag tcgacgtgat tcaggaatct ggagcctgca gatcatttt ttcagcctga       360 tatcgttctt ttccactgag aaccatcaga ccaccttttc ttccattgtg tgaaggagta      420
ggagttgccg tgctgctttg tgggagacat ctgcgatggt gaccagcctc ccgtcgtctg      480
gtcgacgtga cgagcctctt cactgttctt cgacggagag acgcaagcga acggctcta       540 gacctttgg acacgcattc tgtgtgtgaa ctagtggaca gtgataccac gtctgaaagc       600
tcaccactgc ccatggtgca gctacttgtc acaaagtttt gactccgtcg gtatcaccat      660
tcgcgctcgt gtgcctggtt gttccgccac gccggcctgc ccggggcgg ggcaatattc       720 taaaatctca cgcaaaacac cgcacttacc cctcacacat attcgtgata gaccaccacc      780
aatctcagcc cgcatcaaca                                                   800
```

<210> SEQ ID NO 9
<211> LENGTH: 613
<212> TYPE: DNA
<213> ORGANISM: Nannochloropsis oceanica

<400> SEQUENCE: 9

```
gcttctgtgg aagagccagt ggtagtagca gtagcagcag cagtagcagc cgcagcactc       60
```

| | | |
|---|---|---|
| agtgttggcg cgagagattg tccatccctt cttaacctac cggaagagaa ataaggcctt | 120 | |
| tctcccgtag ctgtcttcgt ttgtttgtgc tgattgcttg atatgagagt gttgaattcc | 180 | |
| tgcatcatgt ttttctctgt agtcctttcc taccccgtc attttctttt ctccctggtt | 240 | |
| cttcttttgt caccttatt ttacataaaa ttttctttgt ttatagtgag aggaaggtag | 300 | |
| agagggaaa acaagaacaa cgaacgcaag cgtgtgaaag gagggcgagt agaagagaaa | 360 | |
| cagatctgtt gagcattgag agtggagccg ggggaaaggc ttgtgtgttg tctttgaaaa | 420 | |
| agttgtttaa atcacgaatc cgttagttct catgtgtacc tctttcacta catgtgatgg | 480 | |
| agaaaacaaa agtgtgagga ttaattgaag aaaaagaaga gttcgacacg tcaaaccgcc | 540 | |
| caaaagacgt cacaaagaga acttgattct ctttgccgtg ttgatcctgt cttttccccc | 600 | |
| agcttttctt gcc | 613 | |

```
<210> SEQ ID NO 10
<211> LENGTH: 35
<212> TYPE: DNA
<213> ORGANISM: Artificial Sequence
<220> FEATURE:
<223> OTHER INFORMATION: Primer 10

<400> SEQUENCE: 10
```

| | |
|---|---|
| cttttttgtg aagcaatggc caagctgacc agcgc | 35 |

```
<210> SEQ ID NO 11
<211> LENGTH: 36
<212> TYPE: DNA
<213> ORGANISM: Artificial Sequence
<220> FEATURE:
<223> OTHER INFORMATION: Primer 11

<400> SEQUENCE: 11
```

| | |
|---|---|
| tttcccccat cccgattagt cctgctcctc ggccac | 36 |

```
<210> SEQ ID NO 12
<211> LENGTH: 35
<212> TYPE: DNA
<213> ORGANISM: Artificial Sequence
<220> FEATURE:
<223> OTHER INFORMATION: Primer 12

<400> SEQUENCE: 12
```

| | |
|---|---|
| cgagctcggt acccgactgc gcatggattg accga | 35 |

```
<210> SEQ ID NO 13
<211> LENGTH: 28
<212> TYPE: DNA
<213> ORGANISM: Artificial sequence
<220> FEATURE:
<223> OTHER INFORMATION: Primer 13

<400> SEQUENCE: 13
```

| | |
|---|---|
| tgcttcacaa aaagacagc ttcttgat | 28 |

```
<210> SEQ ID NO 14
<211> LENGTH: 25
<212> TYPE: DNA
<213> ORGANISM: Artificial sequence
<220> FEATURE:
<223> OTHER INFORMATION: Primer 14

<400> SEQUENCE: 14
```

| | |
|---|---|
| tcgggatggg ggaaaaaaac ctctg | 25 |

```
<210> SEQ ID NO 15
<211> LENGTH: 36
<212> TYPE: DNA
<213> ORGANISM: Artificial sequence
<220> FEATURE:
<223> OTHER INFORMATION: Primer 15

<400> SEQUENCE: 15
actctagagg atccccttc gtaaataaat cagctc                          36

<210> SEQ ID NO 16
<211> LENGTH: 20
<212> TYPE: DNA
<213> ORGANISM: Artificial sequence
<220> FEATURE:
<223> OTHER INFORMATION: Primer 16

<400> SEQUENCE: 16
gggatcctct agagtcgacc                                           20

<210> SEQ ID NO 17
<211> LENGTH: 20
<212> TYPE: DNA
<213> ORGANISM: Artificial sequence
<220> FEATURE:
<223> OTHER INFORMATION: Primer 17

<400> SEQUENCE: 17
cgggtaccga gctcgaattc                                           20

<210> SEQ ID NO 18
<211> LENGTH: 35
<212> TYPE: DNA
<213> ORGANISM: Artificial sequence
<220> FEATURE:
<223> OTHER INFORMATION: Primer 18

<400> SEQUENCE: 18
cgagctcggt acccgttctt ccgcttgttg ctgcc                          35

<210> SEQ ID NO 19
<211> LENGTH: 25
<212> TYPE: DNA
<213> ORGANISM: Artificial sequence
<220> FEATURE:
<223> OTHER INFORMATION: Primer 19

<400> SEQUENCE: 19
tgttgatgcg ggctgagatt ggtgg                                     25

<210> SEQ ID NO 20
<211> LENGTH: 21
<212> TYPE: DNA
<213> ORGANISM: Artificial sequence
<220> FEATURE:
<223> OTHER INFORMATION: Primer 20

<400> SEQUENCE: 20
gcttctgtgg aagagccagt g                                         21

<210> SEQ ID NO 21
<211> LENGTH: 28
<212> TYPE: DNA
<213> ORGANISM: Artificial sequence
<220> FEATURE:
```

<210> SEQ ID NO 21
<211> LENGTH: 28
<212> TYPE: DNA
<213> ORGANISM: Artificial sequence
<220> FEATURE:
<223> OTHER INFORMATION: Primer 21

<400> SEQUENCE: 21
ggcaagaaaa gctgggggaa aagacagg                                        28

<210> SEQ ID NO 22
<211> LENGTH: 35
<212> TYPE: DNA
<213> ORGANISM: Artificial sequence
<220> FEATURE:
<223> OTHER INFORMATION: Primer 22

<400> SEQUENCE: 22
ccagcttttc ttgccactgc gcatggattg accga                                35

<210> SEQ ID NO 23
<211> LENGTH: 38
<212> TYPE: DNA
<213> ORGANISM: Artificial sequence
<220> FEATURE:
<223> OTHER INFORMATION: Primer 23

<400> SEQUENCE: 23
ttcttccgct tgttgctgcc gatggcggcc atggtctc                             38

<210> SEQ ID NO 24
<211> LENGTH: 40
<212> TYPE: DNA
<213> ORGANISM: Artificial sequence
<220> FEATURE:
<223> OTHER INFORMATION: Primer 24

<400> SEQUENCE: 24
ctttcgtaaa taaatcagct cctcctcgga gaagcgaaag                           40

<210> SEQ ID NO 25
<211> LENGTH: 39
<212> TYPE: DNA
<213> ORGANISM: Artificial sequence
<220> FEATURE:
<223> OTHER INFORMATION: Primer 25

<400> SEQUENCE: 25
cagcccgcat caacaatggc taatacccgc cacaccaac                            39

<210> SEQ ID NO 26
<211> LENGTH: 39
<212> TYPE: DNA
<213> ORGANISM: Artificial sequence
<220> FEATURE:
<223> OTHER INFORMATION: Primer 26

<400> SEQUENCE: 26
ctcttccaca gaagctcaca tatccaaggc ttctataat                            39

<210> SEQ ID NO 27
<211> LENGTH: 723
<212> TYPE: PRT
<213> ORGANISM: Nannochloropsis oceanica

<400> SEQUENCE: 27

Met Val Ala Lys Ala Ala Phe Ala Gly Val Ala Ala Met Gly Val Leu
1               5                   10                  15

Gly Ala Gln Ala Phe Ile Pro Thr Pro Val Ser Leu Ser Ser Val Phe
            20                  25                  30

Gly Gln Arg Thr Ser Ala Ala Arg Ser Gly Pro Val Met Met Ala Thr
         35                  40                  45

Val Ala Pro Ala Lys Ala Val Ala Thr Pro Ala Asp Leu Thr Arg Ala
 50                  55                  60

Ala Asn Glu Ala Arg Gly Leu Ala Leu Asp Ser Ile Thr Ala Ala His
 65                  70                  75                  80

Ser Gly His Leu Gly Leu Pro Leu Gly Ala Ala Asp Ile Gly Ala Val
                 85                  90                  95

Leu Trp Gly Lys Leu Leu Gln His Asn Pro Glu Asp Pro Gln Trp Ile
                100                 105                 110

Asn Arg Asp Arg Phe Ile Leu Ser Ala Gly His Gly Ser Met Phe Ile
            115                 120                 125

Tyr Ser Trp Leu His Leu Ser Gly Tyr Ala Leu Pro Leu Glu Glu Val
        130                 135                 140

Lys Lys Phe Arg Gln His His Ser Met Thr Pro Gly His Pro Glu Phe
145                 150                 155                 160

Pro Ser Ser Glu His Asn Thr Pro Gly Ile Glu Cys Thr Thr Gly Pro
                165                 170                 175

Leu Gly Gln Gly Val Ser Asn Ala Val Gly Met Ala Ala Ala Gln Lys
            180                 185                 190

His Ala Ala Ser Tyr Asn Thr Pro Lys His Thr Ile Phe Asn Gly
        195                 200                 205

His Ile Ile Ala Leu Gly Gly Asp Gly Cys Ile Gln Glu Gly Val Ala
    210                 215                 220

Ala Glu Ser Ala Ala Phe Ala Ala His Glu Lys Leu Asp Asn Leu Ile
225                 230                 235                 240

Ile Leu Tyr Asp Ala Asn Asp Val Thr Leu Asp Ala Met Ala Asp Arg
                245                 250                 255

Thr Gln Ser Glu Asp Val Ala Met Arg Tyr Lys Ala Tyr Gly Trp Asp
            260                 265                 270

Val Val Thr Ile Asp Gly His Asp Leu Thr Ala Ile Glu Lys Ser Ile
        275                 280                 285

Ser Asp Ala Lys Ala Asn Asp Asn Gly Lys Pro Lys Met Ile Ile Cys
290                 295                 300

Lys Thr Ile Ile Gly Lys Gly Ile Asp Glu Ile Ala Gly Thr Asn Ala
305                 310                 315                 320

Ala His Gly Glu Ala Gly Val Lys Phe Cys Asp Glu Ser Arg Lys Arg
                325                 330                 335

Leu Gly Leu Pro Ala Glu Lys Trp Phe Val Ser Pro Glu Thr Arg Ala
            340                 345                 350

Phe Met Ala Ser Arg Gln Ala Thr Leu Lys Ala Glu Tyr Asp Ala Trp
        355                 360                 365

Gln Lys Thr Phe Ala Glu Trp Lys Ser Ala Asn Pro Asp Lys Ala Lys
    370                 375                 380

Leu Leu Gln Asp Ala Ile Asp Lys Lys Val Pro Ser Ser Glu Asp Leu
385                 390                 395                 400

Met Lys Ala Ile Pro Glu Phe Asp Ala Ser Lys Asp Ile Ala Thr Arg
                405                 410                 415

Glu Ala Gly Ala Val Val Leu Gln Pro Val Ala Ala Val Pro Asn
            420                 425                 430

Tyr Leu Thr Gly Ser Ala Asp Leu Phe Gly Ser Thr Lys Asn Tyr Ile
        435                 440                 445

Lys Asn Gly Gly Asp Phe Gly Ser Gly Glu Gly Lys Thr Tyr Thr Gly
        450                 455                 460

Arg Asn Val Leu Tyr Gly Ile Arg Glu His Ala Met Gly Ser Ile Leu
465                 470                 475                 480

Asn Gly Phe Ala Tyr Phe Gly Leu His Arg Val Ser Gly Ala Thr Phe
                485                 490                 495

Leu Val Phe Ala Asp Tyr Met Arg Ala Pro Val Arg Val Ala Ala Leu
            500                 505                 510

Ser Glu Leu Pro Ile Gly Tyr Ile Trp Thr His Asp Ser Ile Gly Val
            515                 520                 525

Gly Glu Asp Gly Pro Thr His Gln Pro Val Gly Thr Val Ser Gly Leu
530                 535                 540

Arg Val Phe Pro Asn Leu Asp Val Ile Arg Pro Ala Asp Ser Glu Glu
545                 550                 555                 560

Thr Ala Gly Ala Phe Ser Ser Ile Val Arg Lys Asp Gly Pro Thr
                565                 570                 575

Ala Leu Ile Leu Thr Arg Gln Asn Val Lys Gln Leu Pro Gly Thr Pro
            580                 585                 590

Ala Glu Lys Arg Ala Gly Val Leu Lys Gly Ala Tyr Ile Val Lys Lys
            595                 600                 605

Glu Ser Gly Pro Leu Lys Ala Ile Ile Met Ala Ser Gly Ser Glu Val
        610                 615                 620

Gln His Ala Val Glu Ala Ala Ala Leu Gly Glu Gly Ile Arg Val
625                 630                 635                 640

Val Ser Met Pro Cys Met Glu Ile Phe Glu Arg Gln Ser Ala Glu Tyr
                645                 650                 655

Lys Glu Ser Ile Leu Pro Ala Asp Cys Arg Lys Arg Ile Ala Met Glu
            660                 665                 670

Ala Gly Val Thr Gly Leu Trp Tyr Lys Tyr Val Gly Leu Asp Gly Lys
            675                 680                 685

Val Ile Gly Val Asp Arg Phe Gly Phe Ser Ala Pro Gly Pro Thr Val
        690                 695                 700

Met Lys Glu Leu Gly Met Thr Ala Asp Asn Leu Val Lys Glu Ala Lys
705                 710                 715                 720

Ala Tyr Leu

<210> SEQ ID NO 28
<211> LENGTH: 2172
<212> TYPE: DNA
<213> ORGANISM: Nannochloropsis oceanica

<400> SEQUENCE: 28
atggttgcta aagctgctttt tgccggcgtt gccgccatgg gtgtgctggg cgcccaagcg      60
ttcatcccca cgcccgtgag cttgagcagc gtgttcggcc agcgtacgtc cgcggcccgc     120
agcggccctg taatgatggc caccgtggca cctgccaagg ccgtcgccac tccggcagac     180
ctcacccgtg cggccaacga agctcgtggt cttgccctgg actccatcac cgctgctcat     240
tctggtcact gggtcttcc ccttgggggcc gccgacatcg cgctgtgct ttggggcaaa      300 ctccttcagc acaaccccga ggaccccag tggatcaacc gtgaccgatt catcctctca     360
gccggtcacg gttctatgtt catttactcc tggctgcact tgtccgggta cgcgctgccc     420
ctggaggagg tgaagaagtt ccgccagcac cactccatga ccccggcca cccagagttc     480 ccctcctccg agcacaacac gcccggcatt gagtgtacta cgggtcccct gggccagggt     540

-continued

| | | | |
|---|---|---|---|
| gtttccaacg ccgtcgggat ggccgcagcc cagaagcacg ccgcagccag ctacaacacg | | | 600 |
| cccaagcaca cgatattcaa tggccacatc atcgccctcg gcggtgacgg ctgcattcag | | | 660 |
| gagggtgtcg ccgcagagtc ggccgccttt gcagcccacg agaaactgga caacctgatc | | | 720 |
| attctgtacg acgcgaatga cgtgaccctg gacgctatgg ctgaccgcac ccagtccgag | | | 780 |
| gacgtggcta tgcgctacaa ggcctacggg tgggacgttg tgaccatcga cgggcacgac | | | 840 |
| ctgaccgcca tcgagaagtc tatctccgat gccaaggcta acgataacgg caagcccaag | | | 900 |
| atgattattt gcaaaaccat catcggtaag ggcattgacg agatcgccgg caccaacgcc | | | 960 |
| gcccacggtg aagccggggt caaattctgt gacgagtccc gcaagcgcct cggcctcccc | | | 1020 |
| gctgagaagt ggtttgtatc tcccgagacc cgtgctttta tggcttcccg ccaggccacc | | | 1080 |
| ctcaaggccg agtacgatgc ctggcagaaa accttcgccg agtggaagtc cgccaacccc | | | 1140 |
| gacaaggcca agctgctcca ggacgcgatc gacaagaagg tgccctcctc ggaggatctg | | | 1200 |
| atgaaggcca tccccgaatt cgacgcctct aaggacatcg ctacccgtga ggccggcgcc | | | 1260 |
| gtcgtcctcc agcccgtggc cgccgctgtg ccgaattacc tgaccggctc ggctgatctc | | | 1320 |
| ttcggctcca ccaagaacta catcaagaac ggtggcgact cggcagcgg cgagggtaag | | | 1380 |
| acctacacgg gccgcaacgt cctctatggc atccgcgagc acgcaatggg ctccatcctc | | | 1440 |
| aacggttttg cctatttcgg cttgcaccgg gtctccgggg ccactttctt ggtcttcgcc | | | 1500 |
| gactacatgc gcgcgcccgt ccgtgtcgcc gccctctccg agctccccat cgggtacatc | | | 1560 |
| tggacgcacg actcaatcgg tgtcggtgag gatggaccta cccaccagcc ggtggagacg | | | 1620 |
| gtatctggtc ttcgtgtctt tcccaacctt gacgtcatcc gccccgccga ctccgaggaa | | | 1680 |
| accgccggtg ccttcgtctc ctccatcgtg cgcaaggacg gtcccaccgc gcttatcctt | | | 1740 |
| acccgccaga acgtgaaaca gctccccggc actcccgccg agaagcgtgc cggcgttctc | | | 1800 |
| aagggcgctt acatcgtgaa gaaagagtct gggcccctca aggccatcat catggcttcc | | | 1860 |
| ggctctgagg tgcagcacgc cgtcgaggcc gctgctgccc tgggcgaggg aatccgtgtc | | | 1920 |
| gtctctatgc catgcatgga gatcttcgag cgccagtcgg ctgaatacaa ggagtccatc | | | 1980 |
| ctccctgcgg actgtcgtaa gcgtatcgcc atggaggcgg gcgtgacggg cttgtggtac | | | 2040 |
| aagtacgttg gcttggacgg gaaggtcatc ggtgtggacc gctttgggtt ctcggccccg | | | 2100 |
| ggccccaccg tcatgaagga gttgggcatg acggccgaca atctcgtcaa ggaggccaag | | | 2160 |
| gcctatctgt aa | | | 2172 |

<210> SEQ ID NO 29
<211> LENGTH: 382
<212> TYPE: PRT
<213> ORGANISM: Nannochloropsis oceanica

<400> SEQUENCE: 29

Met Ala Arg Leu Phe Val Thr Val Ala Ser Phe Val Ala Ala Cys Ala
1               5                   10                  15

Thr Val Asn Ala Phe Gln Val Pro Arg Met Ser Leu Asp Lys Tyr Arg
            20                  25                  30

Ser Glu Leu Ala Glu Thr Ala Lys Lys Ile Ala Ala Pro Gly Lys Gly
        35                  40                  45

Ile Leu Ala Val Asp Glu Ser Thr Lys Thr Ile Gly Lys Arg Leu Glu
    50                  55                  60

Gly Ile Ser Val Glu Asn Thr Glu Ala Asn Arg Gln Ala Tyr Arg Gly
65                  70                  75                  80

Leu Leu Phe Thr Thr Pro Asn Ile Gly Asn Tyr Ile Ser Gly Ala Ile
            85                  90                  95

Leu Tyr Glu Glu Thr Leu Phe Gln Asn Asn Val Asp Gly Thr Pro Phe
            100                 105                 110

Val Lys Asn Leu Asn Thr Ala Gly Val Ile Pro Gly Ile Lys Val Asp
            115                 120                 125

Met Gly Leu Ser Pro Leu Pro Gly Gly His Pro Val Glu Thr Trp Cys
130                 135                 140

Thr Gly Leu Asp Gly Leu Val Glu Arg Ala Gln Lys Tyr Tyr Ala Gln
145                 150                 155                 160

Gly Ala Arg Phe Ala Lys Trp Arg Ala Val Leu Gln Ile Thr Ser Asp
            165                 170                 175

Gly Ala Pro Ser Glu Leu Ser Ile Gln Glu Asn Ala Trp Gly Leu Ala
            180                 185                 190

Arg Tyr Ala Arg Ala Val Gln Glu Gly Gly Leu Val Pro Ile Val Glu
            195                 200                 205

Pro Glu Ile Leu Met Asp Gly Asp His Asn Ile Glu Thr Thr Ala Arg
            210                 215                 220

Val Gln Glu Arg Val Leu Ala Ala Val Tyr Lys Ala Leu Ser Asp Asn
225                 230                 235                 240

Gly Val Tyr Leu Glu Gly Ser Leu Leu Lys Pro Ser Met Thr Leu Pro
            245                 250                 255

Gly Ala Asp Cys Gly Glu Thr Val Thr Ser Glu Lys Ile Ala Glu Tyr
            260                 265                 270

Thr Val Arg Thr Leu Glu Arg His Val Pro Ser Ser Val Pro Gly Val
            275                 280                 285

Met Phe Leu Ser Gly Gly Met Ser Glu Glu Glu Ala Ser Ile Asn Leu
            290                 295                 300

Asn Ala Leu Asn Lys Arg Ala Arg Lys Gly Pro Trp Ser Leu Ser Phe
305                 310                 315                 320

Ser Tyr Gly Arg Ala Leu Gln Gln Ser Cys Leu Lys Ala Trp Gln Gly
            325                 330                 335

Lys Gln Glu Asn Val Pro Ala Ala Arg Ala Ala Leu Leu Ala Arg Ala
            340                 345                 350

Gln Ala Asn Ser Glu Ala Asn Leu Gly Lys Tyr Val Ala Gly Ser Gln
            355                 360                 365

Pro Ser Ala Asp Glu Thr Leu Phe Val Lys Gly Tyr Lys Tyr
            370                 375                 380

<210> SEQ ID NO 30
<211> LENGTH: 1149
<212> TYPE: DNA
<213> ORGANISM: Nannochloropsis oceanica

<400> SEQUENCE: 30
atggctcgcc tcttcgtcac cgttgcctcc ttcgtggccg cctgtgccac cgtcaacgcc      60
ttccaggtgc cccgtatgtc tttggacaag tacaggagcg agctggccga gaccgctaag     120
aagattgccg cccccggcaa gggtattttg gccgtagatg agtcgaccaa gaccatcggc     180
aagcgtttgg aagggatcag cgtggagaac acggaggcca accgtcaggc gtaccgtggt     240
ctcctcttca ccaccccaa catcggcaac tacatctccg gcgccatcct ctacgaggag     300
actctcttcc agaacaacgt ggacggtacc cccttcgtca agaacctgaa cactgctggc     360
gtcattccgg gtatcaaggt cgacatgggt ctgtcgcccc ttcccggggg acaccccgtc     420

```
gagacctggt gcacgggctt ggacggactc gtcgagcgcg ctcagaagta ctacgctcaa    480
ggcgcgcgtt tcgcgaagtg gcgtgccgtg ctccagatca cctccgacgg tgccccctct    540
gagctctcca tccaagagaa cgcgtggggc ctggcccgtt acgcgcgtgc cgtgcaagag    600
ggtggcctgg ttcccattgt cgagcccgag atcctgatgg acggcgacca caatatcgag    660
acgactgcgc gtgtgcagga gcgtgtcttg gccgcggtct acaaggctct gtctgacaac    720
ggcgtgtatc tcgagggctc cctgctcaag ccctctatga ctctccccgg agccgactgc    780
ggggaaaccg tcacgtccga agatcgctga gtatacgg ttcgcaccct cgagcgccac    840
gtcccttcgt ccgtacctgg tgtgatgttc ctctccggcg catgtccga ggaggaggcc    900 tccatcaacc tgaacgccct gaacaagcgc gctcgtaagg gcccgtggtc cttgtccttt    960
tcctacggcc gtgctctgca gcagtcttgc ctcaaggcgt ggcaggggaa gcaggagaac   1020
gtccccgccg cccgcgcggc tttgttggcc cgtgcccagg ctaacagcga ggccaacctg   1080
ggaaagtacg tcgcgggctc ccagccgtcg gcggacgaga ccctgttcgt gaagggtat    1140 aagtactaa                                                           1149
```

<210> SEQ ID NO 31
<211> LENGTH: 282
<212> TYPE: PRT
<213> ORGANISM: Nannochloropsis oceanica

<400> SEQUENCE: 31

```
Met Ser Arg Gln Lys Thr Leu Phe Ser Val Met Ala Met Val Thr Val
1               5                   10                  15

Gly Ala Ser Ala Phe Ile Leu Pro Val Arg Gln Pro Leu His Gly Pro
            20                  25                  30

Ala Leu Cys Thr Arg Arg Ala Ser Thr Thr Ala Arg Phe Ala Val
        35                  40                  45

Ser Gln Asp Glu Leu Lys Lys Gln Val Gly Tyr Lys Ser Val Asp Asp
    50                  55                  60

Tyr Val Thr Ser Gly Met Val Val Gly Leu Gly Thr Gly Ser Thr Ala
65                  70                  75                  80

Ala Phe Ala Val Glu Arg Leu Gly Gln Lys Leu Lys Ala Gly Glu Leu
                85                  90                  95

Lys Asp Ile Val Ala Ile Pro Thr Ser Ile Arg Thr Lys Glu Gln Ala
            100                 105                 110

Glu Gly Leu Gly Ile Pro Leu Val Thr Leu Asp Thr His Ser Val Leu
        115                 120                 125

Asp Val Ala Ile Asp Gly Ala Asp Glu Val Asp Pro Ala Leu Asn Leu
    130                 135                 140

Val Lys Gly Arg Gly Gly Ala Leu Leu Arg Glu Lys Met Val Glu Val
145                 150                 155                 160

Cys Ala Lys Lys Phe Ile Val Ile Val Asp Asp Ser Lys Met Val Pro
                165                 170                 175

Gly Leu Gly Val Thr Gly Ala Met Pro Val Glu Ile Thr Pro Phe Cys
            180                 185                 190

His Glu His Thr Gln Arg Thr Ile Leu Gly Leu Pro Gly Val Lys Gly
        195                 200                 205

Ala Ala Thr Gly Lys Leu Arg Met Asp Gly Asp Lys Pro Tyr Val Thr
    210                 215                 220

Asp Asn Asp Asn Tyr Ile Val Asp Leu Tyr Tyr Thr Ala Pro Ile Ala
225                 230                 235                 240
```

```
Asp Val Met Ala Val Ala Gly Ala Leu Glu Lys Val Gly Val Val
                245                 250                 255

Glu His Gly Phe Phe Leu Asp Met Thr Thr Ala Val Ile Val Ala Gly
            260                 265                 270

Lys Thr Gly Ile Asp Val Ile Asn Lys Lys
        275                 280
```

```
<210> SEQ ID NO 32
<211> LENGTH: 849
<212> TYPE: DNA
<213> ORGANISM: Nannochloropsis oceanica

<400> SEQUENCE: 32
atgagccgcc aaaagactct cttttctgtc atggccatgg tcaccgtggg tgcctctgcg    60
tttatccttc ctgtccgcca gcccctgcac ggcccggctc tgtgcactcg ccgtgcctcg   120
accaccaccg cgcgcttcgc cgtgagccaa gacgagctca gaagcaagt gggctacaag    180
tccgtggatg actacgtgac cagcggcatg gtcgtgggcc tggcaccgg ttccactgcc    240
gcctttgctg tggagcgcct cgggcagaag ctcaaggctg cgagcttaa ggacatcgtt    300
gccatcccta cttccatccg caccaaggag caagcggaag gcctgggaat ccccctggtg   360
acgcttgaca ctcactctgt gttggatgtg gccattgacg gtgccgatga ggtggacccg   420
gctctgaact tggtgaaggg acgagggggt gctttgctgc gtgagaagat ggtggaggtg   480
tgcgctaaga agttcatcgt cattgtggac gacagcaaga tggtgcctgg cctgggagtc   540
actggtgcga tgcccgtgga gatcaccccc ttctgccatg agcacactca acggacgatc   600
ctaggcttgc caggggtgaa gggcgcggcg acggggaagc ttcgcatgga tggagacaag   660
ccctacgtga ctgacaatga caactacatc gtggatttgt actacaccgc gccaattgcg   720
gacgtgatgg ccgttgcggg ggcgctggag aaggtggtag gtgtggtgga gcacggtttt   780
ttcttagaca tgaccacggc ggtgatcgtg gctgggaaga cgggcatcga cgtcatcaat   840
aagaagtag                                                           849
```

```
<210> SEQ ID NO 33
<211> LENGTH: 363
<212> TYPE: PRT
<213> ORGANISM: Nannochloropsis oceanica

<400> SEQUENCE: 33

Met Thr Pro Gln Ala Asp Ile Thr Ser Lys Thr Thr Pro Asn Leu Lys
1               5                   10                  15

Thr Ala Ala Ser Ser Pro Ser Lys Thr Ser Pro Ala Pro Ser Val Gln
            20                  25                  30

Tyr Lys Ala Ala Asn Gly Lys Val Ile Thr Val Ala Met Ala Glu Gln
        35                  40                  45

Asp Asp Gly Asn Met Gly Ile Phe Arg Glu Cys Phe Ala Met Val Thr
    50                  55                  60

Met Gly Ile Ile Met Ser Trp Tyr Tyr Ile Val Ile Leu Ser Leu
65                  70                  75                  80

Leu Cys Leu Val Gly Ile Cys Ile Phe Pro Ala Trp Arg Ala Val Ala
                85                  90                  95

Ala Thr Val Phe Val Leu Met Trp Ser Ala Ala Leu Leu Pro Leu Asp
            100                 105                 110

Tyr Gln Gly Trp Asp Ala Phe Cys Asn Ser Phe Ile Phe Arg Leu Trp
        115                 120                 125
```

```
Arg Asp Tyr Phe His Tyr Glu Tyr Val Leu Glu Glu Met Ile Asp Pro
    130                 135                 140

Asn Lys Arg Tyr Leu Phe Ala Glu Met Pro His Gly Ile Phe Pro Trp
145                 150                 155                 160

Gly Glu Val Ile Ser Ile Ser Ile Thr Lys Gln Leu Phe Pro Gly Ser
                165                 170                 175

Arg Val Gly Ser Ile Gly Ala Ser Val Ile Phe Leu Leu Pro Gly Leu
                180                 185                 190

Arg His Phe Phe Ala Trp Ile Gly Cys Arg Pro Ala Ser Pro Glu Asn
            195                 200                 205

Ile Lys Lys Ile Phe Glu Asp Gly Gln Asp Cys Ala Val Thr Val Gly
210                 215                 220

Gly Val Ala Glu Met Phe Leu Val Gly Gly Asp Lys Glu Arg Leu Tyr
225                 230                 235                 240

Leu Lys Lys His Lys Gly Phe Val Arg Glu Ala Met Lys Asn Gly Ala
                245                 250                 255

Asp Leu Val Pro Val Phe Cys Phe Gly Asn Ser Lys Leu Phe Asn Val
                260                 265                 270

Val Gly Glu Ser Ser Arg Val Ser Met Gly Leu Met Lys Arg Leu Ser
                275                 280                 285

Arg Arg Ile Lys Ala Ser Val Leu Ile Phe Tyr Gly Arg Leu Phe Leu
            290                 295                 300

Pro Ile Pro Ile Arg His Pro Leu Leu Phe Val Val Gly Lys Pro Leu
305                 310                 315                 320

Pro Val Val His Lys Ala Glu Pro Thr Lys Glu Glu Ile Ala Ala Thr
                325                 330                 335

His Ala Leu Phe Cys Glu Lys Val Glu Glu Leu Tyr Tyr Lys Tyr Arg
                340                 345                 350

Pro Glu Trp Glu Thr Arg Pro Leu Ser Ile Glu
                355                 360
```

<210> SEQ ID NO 34
<211> LENGTH: 1092
<212> TYPE: DNA
<213> ORGANISM: Nannochloropsis oceanica

<400> SEQUENCE: 34

```
atgacgccgc aagccgacat caccagcaag acgacaccca acctcaagac ggctgcgtca   60 tcccccctcca agacctcgcc cgccccctcc gttcaataca aggcggcgaa tggcaaggtg  120
atcacggtgg ccatggccga gcaagacgac gggaacatgg gcattttccg cgagtgtttt  180
gcaatggtga caatgggcat aattatgtcg tggtattaca tcgtcgtcat tctctcccctc  240 ctctgcttgg tggggatctg catcttccct gcctggcggg cggtagcggc cacggttttt  300
gtgcttatgt ggagtgcggc gctattgccg cttgactacc agggatggga tgctttctgc  360 aactcctttta tcttcaggct gtggcgggac tacttccact atgaatacgt cctggaggag  420
atgatcgacc caaacaagcg ctacctcttt gctgagatgc ctcacggtat cttcccctgg  480
ggagaggtga tttccatttc gatcaccaaa cagcttttc ccgggagccg cgtaggctcc  540
atcggtgcga gtgtcatctt cctccttccc ggtctcaggc acttcttcgc ttggatcggg  600
tgtcggcccg cgagcccaga gaacatcaaa aagatttttg aggatgggca ggactgtgcc  660
gtgacggtgg ggggggtcgc cgagatgttt ctagtcggag agacaaggga acgactgtac  720
ctgaagaagc acaagggttt cgttcgagaa gccatgaaga tgggggcgga cctggttcct  780
```

```
gtcttctgct tcggcaacag caagctgttc aatgtggtgg gggagagcag tcgggtttct    840
atgggcctga tgaagcgcct ctcaaggagg attaaggcca gcgtcctcat cttttacggc    900
cgtctcttcc tgcccattcc gattcgacac ccgctcttgt tcgtggtggg gaagcccctg    960
ccggtcgtgc acaaggcaga gccgaccaag gaggagatcg cggcaacgca cgcactcttt   1020
tgcgagaagg tcgaggagct ttactacaaa tacaggccgg agtgggagac gcgcccgttg   1080
tccattgagt aa                                                       1092

<210> SEQ ID NO 35
<211> LENGTH: 648
<212> TYPE: PRT
<213> ORGANISM: Nannochloropsis oceanica

<400> SEQUENCE: 35
```

Met Pro Ala Tyr Thr Thr Thr Ser Ala Ser Gly Glu Val Asp Leu Arg
1               5                   10                  15

Met Glu Lys Glu Gly Pro Gly Ala Trp Glu Pro Arg Thr Val Tyr Gln
            20                  25                  30

Val Phe Glu Glu Thr Val Gln Arg Tyr Gly Asp Arg Pro Ala Leu His
        35                  40                  45

Phe Lys Lys Val Pro His Gly Ser Pro Glu Thr Thr Glu Trp Ser
    50                  55                  60

Val Tyr Thr Trp Arg Glu Tyr Tyr Asp Leu Thr Leu Thr Phe Ala Lys
65                  70                  75                  80

Ser Leu Leu Ala Leu Asp Phe Pro Ala His Gly Ala Ile Asn Ile Ile
                85                  90                  95

Gly Phe Asn Ser Pro Glu Trp Leu Ile Ala Asn Cys Gly Ala Ile Ala
            100                 105                 110

Ala Gly Gly Val Gly Val Gly Ile Tyr Thr Ser Asn Asn Ala Glu Ala
        115                 120                 125

Cys Asn Tyr Ile Ser Glu His Ser Glu Ala Glu Val Val Val Val Glu
    130                 135                 140

Asn Ala Lys Gln Leu Glu Lys Tyr Val Lys Ile Ala Lys Asn Leu Pro
145                 150                 155                 160

Arg Leu Lys Ala Leu Val Val Tyr Asp Gly Thr Gly Glu Gly Phe Thr
                165                 170                 175

Cys Asp Thr Pro Ile Tyr Ser Trp Lys Ala Phe Met Ala Leu Gly Lys
            180                 185                 190

Asp Lys Ser Glu Ala Ala Val Arg Ala Arg Ile Glu Ala Gln Arg Pro
        195                 200                 205

Gly His Cys Cys Thr Leu Ile Tyr Thr Ser Gly Thr Thr Gly Pro Pro
    210                 215                 220

Lys Ala Val Met Ile Ser His Asp Asn Leu Thr Trp Thr Val Lys Asn
225                 230                 235                 240

Phe Val Ala Ala Leu Pro Phe Thr Leu Thr Cys Glu Asp Arg Ser Val
                245                 250                 255

Ser Ser Leu Pro Leu Ser His Val Ala Ala Gln Met Leu Asp Val His
            260                 265                 270

Cys Pro Ile Ala Ser Gly Ala Lys Ile Tyr Phe Ala Gln Ala Asp Ala
        275                 280                 285

Leu Arg Gly Ser Leu Pro Asn Thr Leu Lys Asp Val Cys Pro Thr Tyr
    290                 295                 300

Phe Phe Gly Val Pro Arg Val Trp Glu Lys Ile Tyr Glu Lys Met Gln
305                 310                 315                 320

| | | | | | | | | | | | |
|---|---|---|---|---|---|---|---|---|---|---|---|
|Glu|Val|Ala|Arg|Ser|Thr|Thr|Gly|Val|Lys|Arg|Ala|Leu|Ala|Gln|Trp|
| | | | |325| | | |330| | | |335| | | |

Ala Lys Ala Lys Gly Leu Glu Lys Asn Arg Arg Gln Gln Tyr Gly Gly
            340                345                350

Gly Gly Gly Ala Pro Val Gly Phe Gly Cys Ala Tyr Ala Leu Val Leu
        355                360                365

Ser Lys Val Lys Ala Ala Leu Gly Leu His Gln Thr Lys Ile Cys Ile
370                  375                380

Thr Ser Ala Ala Pro Ile Ser Val Glu Val Leu Glu Tyr Phe Ala Ser
385                  390                395              400

Leu Asp Ile Pro Val Leu Glu Leu Phe Gly Gln Ser Glu Cys Thr Gly
        405                410                415

Pro His Thr Ser Asn Phe Ser Tyr Ala Trp Lys Ile Gly Ser Ile Gly
        420                425                430

Arg Asp Ile Pro Gly Val Lys Thr Lys Gln Glu Ala Ala Ala Lys Glu
        435                440                445

Phe Cys Met Phe Gly Arg His Ile Met Met Gly Tyr Met Lys Met Glu
        450                455                460

Glu Lys Thr Lys Glu Ala Val Asp Glu Glu Gly Trp Leu His Ser Gly
465                  470                475              480

Asp Val Ala Asp Val Asp Ala Asp Gly Phe Trp Thr Ile Thr Gly Arg
                485                490              495

Ile Lys Glu Leu Ile Ile Thr Ala Gly Gly Glu Asn Ile Pro Pro Val
        500                505                510

Leu Ile Glu Thr Glu Val Lys Ala Ala Leu His Ala Val Ala Asn Cys
        515                520                525

Met Val Val Gly Asp Lys Lys Lys Phe Leu Thr Val Leu Leu Thr Met
        530                535                540

Lys Thr Lys Leu Asp Glu Gln Gly Asn Pro Thr Asn Ala Leu Asn Arg
545                  550                555              560

Glu Ala Leu Asp Ile Gly Lys Glu Leu Gly Ser Ala Thr Thr Thr
              565                570                575

Glu Gln Val Gly Lys Asp Pro Ala Trp Lys Lys Tyr Phe Asp Glu Gly
        580                585                590

Leu Lys Lys Ala Asn Ala Ala Ala Thr Ser Asn Ala Gln Phe Val Gln
        595                600                605

Lys Trp Ala Val Leu Pro Leu Asp Phe Ser Glu Lys Gly Gly Glu Leu
        610                615                620

Thr Pro Thr Leu Lys Leu Lys Arg Ser Val Val Ala Glu Lys Tyr Ala
625                  630                635              640

Asp Val Ile Ala Asn Leu Tyr Lys
        645

<210> SEQ ID NO 36
<211> LENGTH: 1947
<212> TYPE: DNA
<213> ORGANISM: Nannochloropsis oceanica

<400> SEQUENCE: 36

```
atgcccgcct acacgacgac atcggcgtcc ggggaggtgg acttgcgcat ggagaaggag    60
ggccctggag cttgggagcc ccgaactgtt taccaggtct tcgaggagac tgtccaacgt   120
tacggggacc ggcccgcgct ccacttcaag aaagttccgc acggcggtag ccccgagacg   180
actgagtgga gcgtttacac atggcgcgaa tactatgacc tgaccctcac cttcgccaag   240
```

```
agcctcctgg ccctcgactt cccggcccac ggggccatca acatcatcgg tttcaactcg    300
cctgagtggc tcatcgccaa ctgcggtgcc attgccgcgg gtggcgtggg tgtgggtatc    360
tatacgagca acaacgcgga ggcctgcaat tacatctcgg agcactcgga ggctgaagtg    420
gttgtggtgg agaacgctaa gcagctggag aagtacgtaa aaatcgccaa gaacctgccc    480
cgccttaagg cgctggtggt gtacgatggc acgggcgagg gattcacgtg tgacacgcct    540
atatactcct ggaaggcctt catggcactg ggaaaggaca aaagcgaggc agcggtccgt    600
gcgcgcattg aggcccagcg gcccggacat tgttgcacgc tcatctacac gtccggcacc    660
acgggccccgc ccaaggccgt catgatatcg cacgataacc tgacctggac cgtcaaaaac    720
tttgtggctg ccctgccttt cacgcttact tgcgaggacc ggtcggtgtc ctccctgccg    780
ctgtcccacg tggcggcaca gatgctggac gtgcactgcc ccatcgcctc gggcgctaag    840
atttatttcg cgcaggccga cgcactccgg ggctcgctac ccaacacgct gaaggatgtc    900
tgtcccacct acttttttgg cgtaccgcgt gtctgggaga gatctacga gaaaatgcag    960
gaggtggcgc gctccaccac aggggtcaag cgggcgctgg cccagtgggc caaagccaag   1020
ggattggaga gaaccggcg ccagcaatat ggggcggtg gtgggcgcc cgtgggattc   1080
ggttgcgctt acgccctcgt cctgtccaaa gtgaaggcgg cgctagggct gcaccagacc   1140
aagatctgca tcacctcggc agcgcccata tccgtcgagg tgctcgaata cttcgcctcc   1200
ctggacatcc ctgtgctaga gctgttcggg cagtccgagt gcacaggccc acacacctcc   1260
aacttctcct acgcctggaa gatcggctcc attggccgcg acataccggg ggttaagacc   1320
aaacaggaag cggccgccaa ggaattctgc atgttcgggc ggcacattat gatgggctac   1380
atgaagatgg aggagaagac caaggaggca gtggacgagg agggttggct gcattcagga   1440
gacgtggccg acgtggatgc ggacgggttc tggaccatca cgggccgtat caaggagctc   1500
atcatcacgg ccggcgggga gaacatcccg cccgtgctaa ttgagaccga ggtcaaggcc   1560
gcccttcacg ccgtggctaa ttgcatggtg gtgggcgata agaagaaatt tttgactgtg   1620
ctgctgacga tgaagaccaa gctggacgag cagggcaacc ccacgaacgc cttgaaccgc   1680
gaggccctgg atatcgggaa agagctgggc tcggaagcca caaccacgga gcaggtcggc   1740
aaggaccctg cctggaagaa gtatttcgac gaggggctca agaaggccaa tgccgccgcc   1800
acctctaatg cgcagttcgt acagaagtgg gccgtgctgc ccttggactt ctccgagaag   1860
ggcggcgagc tcacgcccac gctcaagctc aaacgctctg tggtggccga aaatacgcc   1920
gacgtcatcg ccaatctcta caagtag                                      1947
```

<210> SEQ ID NO 37
<211> LENGTH: 348
<212> TYPE: PRT
<213> ORGANISM: Nannochloropsis oceanica

<400> SEQUENCE: 37

Met Arg Ile Pro Ser Leu Ile Leu Cys Phe Ala Phe Leu Ala Ser Ala
1               5                  10                  15

Pro Ala Val Ala Phe Leu Leu Pro Pro Leu Pro Cys Phe Ser Ser Ser
            20                  25                  30

Leu Gln Thr Val Thr Asn Thr Ile Thr Thr Ser Ser Arg Phe Ser Ser
        35                  40                  45

Ser Ser Ser Ser Ser Ser Ser Ser Ser Ser Ser Ser Ser Arg Pro Arg
    50                  55                  60

```
Cys Ser Pro Leu Leu Ser Val Thr Thr Ala Ala Thr Ala Ser Ser Ala
 65                  70                  75                  80

Thr Glu Glu Ala Glu Asn Pro Ser Leu Thr Gln Gly Val Phe Ile Glu
                 85                  90                  95

His Thr Asp Arg Tyr Gly Met Val Tyr His Ser Asn Tyr Leu Leu Phe
            100                 105                 110

Leu Cys Arg Ala Leu His Leu Thr Leu Gly Arg His Val Val Thr Arg
        115                 120                 125

Leu Asp Asn Phe Arg Phe Lys Ala Ser Ala Arg Leu Gly His Asp Ile
130                 135                 140

Ala Ile Asp Val Arg Pro Lys Ala Gly Lys Asp Asn Thr Phe Val Thr
145                 150                 155                 160

Ser Ile Lys Glu Ser Glu Thr Pro His Thr Thr Phe Ile Thr Ala Asp
                165                 170                 175

Val Ser Ala Phe Pro Leu Pro Glu Arg Gly Arg Glu Gly Gly Arg Glu
            180                 185                 190

Asp Trp Ala Ala Tyr Thr Ile Ser Glu Glu Ala Leu Arg Lys Val
        195                 200                 205

Val Ala Ser Pro Asp Lys Val Met Glu Ala Val Leu Trp Thr Asp Glu
    210                 215                 220

Leu Gly Val His Gly Leu Leu Thr Pro His Ala Val Leu Ser Leu Phe
225                 230                 235                 240

Glu Arg Gly Arg Ser Asp Ser Leu Gly Gly Pro Asp Arg Leu Glu Glu
                245                 250                 255

Leu Met Asp Asp Gly Tyr Met Phe Val Val Ala Arg Ile Asp Gly Tyr
            260                 265                 270

Arg Phe Asp Pro Ser Leu Arg Leu Glu Glu Gly Glu Ala Leu Gln Val
        275                 280                 285

Leu Gly Arg Phe Lys Pro Lys Ser Asp Ala Ile Val Val Cys Glu Gln
    290                 295                 300

Val Leu Ile Val Lys Ala Thr Gln Gln Ile Val Ala Gln Ala Leu Val
305                 310                 315                 320

Thr Leu Ala Cys Ile Gly Ala Val Asp Gly Lys Leu Arg Gly Val Pro
                325                 330                 335

Ser Lys Ala Leu Glu Ser Met Asn Met Gly Thr Thr
            340                 345

<210> SEQ ID NO 38
<211> LENGTH: 1047
<212> TYPE: DNA
<213> ORGANISM: Nannochloropsis oceanica

<400> SEQUENCE: 38
atgagaatac cttcccttat cctttgcttc gcatttctag cgagcgctcc cgctgttgcc      60
ttcctgctgc cgccgctgcc ttgcttctct tcttcgcttc agacagtcac caacacaatc     120
acgacaagca gtcgcttcag cagcagcagc agcagcagca gcagcagcag cagcagcagc     180
agcagaccaa gatgcagccc cttgttatcc gtcacgactg ccgctactgc ttcatctgcg     240
acagaggaag cggaaaaccc gagcttgact caaggagtat tcatcgagca taccgacagg     300
tacgggatgg tctaccactc caactacctg ctcttcctct gtcgcgctct ccacctcacc     360
ctgggccggc acgtggtgac acgcctagat aactttcggt tcaaagcatc ggctcgcctg     420
ggccacgata tcgccatcga cgtgaggccc aaggcgggga agacaacac tttcgtcacc     480 agcatcaagg aaagcgaaac tcctcacact acctttatca ccgcggacgt atcggccttc     540
```

```
ccccttcctg agcgaggaag ggagggagga agggaggatt gggctgcata tacgatctcg      600
gaggaagagg cattgaggaa ggtggtggcc tcccccgaca aggtcatgga ggccgttttg      660
tggaccgacg agctgggagt gcacggcctg ctcacaccgc atgccgtcct ttccctgttt      720
gagcggggaa ggagtgattc cctgggtggt ccggaccgcc tggaggagct catggatgac      780
ggctacatgt tcgtcgtcgc ccgcatcgac ggctaccgct tcgacccctc cctccgtctc      840
gaggagggag aggcccttca agtgctcggc cgatttaagc ccaagtccga cgccatcgtt      900
gtatgcgagc aggtcctcat cgtcaaggcc acccaacaga tcgtggctca ggccctcgtg      960
acgcttgcct gcatcggcgc cgtggatggc aaattgcgag cgtgccttc caaggccctt      1020 gagagtatga acatgggcac gacgtag                                          1047
```

<210> SEQ ID NO 39
<211> LENGTH: 822
<212> TYPE: DNA
<213> ORGANISM: Artificial sequence
<220> FEATURE:
<223> OTHER INFORMATION: Paromomycin resistance gene

<400> SEQUENCE: 39

```
atggtcgaga ttcgaagcat ggacgatgcg ttgcgtgcac tgcggggtcg gtatcccggt       60
tgtgagtggg ttgttgtgga ggatggggcc tcggggctg gtgtttatcg gcttcggggt      120
ggtgggcggg agttgtttgt caaggtggca gctctggggg ccggggtggg cttgttgggt      180
gaggctgaac ggctggtgtg gttggcgag gtggggattc ccgtacctcg tgttgtggag      240
ggtggtgggg acgagagggt cgcctggttg gtcaccgaag cggttccggg gcgtccggcc      300
agtgcgcggt ggccgcggga gcagcggctg acgtggcgg tggcgctcgc ggggctcgct      360
cgttcgctgc acgcgctgga ctgggagcgg tgtccgttcg atcgcagtct cgcggtgacg      420
gtgccgcagg cggcccgtgc tgtcgctgaa gggagcgtcg acttggagga tctggacgag      480
gagcggaagg ggtggtcggg ggagcggctt ctcgccgagc tggagcggac tcggcctgcg      540
gacgaggatc tggcggtttg ccacggtgac ctgtgcccgg acaacgtgct gctcgaccct      600
cgtacctgcg aggtgaccgg gctgatcgac gtggggcggg tcggccgtgc ggaccggcac      660
tccgatctcg cgctggtgct gcgcgagctg gcccacgagg aggacccgtg gttcgggccg      720
gagtgttccg cggcgttcct gcgggagtac gggcgcgggt gggatggggc ggtatcggag      780
gaaaagctgg cgttttaccg gctgttggac gagttcttct ga                        822
```

<210> SEQ ID NO 40
<211> LENGTH: 999
<212> TYPE: DNA
<213> ORGANISM: Artificial sequence
<220> FEATURE:
<223> OTHER INFORMATION: Hygromycin resistance gene

<400> SEQUENCE: 40

```
atgacacaag aatccctgtt acttctcgac cgtattgatt cggatgattc ctacgcgagc       60
ctgcggaacg accaggaatt ctgggagccg ctggcccgcc gagccctgga ggagctcggg      120
ctgccggtgc cgccggtgct gcgggtgccc ggcgagagca ccaacccgt actggtcggc      180 gagcccggcc cggtgatcaa gctgttcggc gagcactggt gcggtccgga gagcctcgcg      240
tcggagtcgg aggcgtacgc ggtcctgcg gacgccccgg tgccggtgcc ccgcctcctc      300
ggccgcggcg agctgcggcc cggcaccgga gcctggccgt ggccctacct ggtgatgagc      360
```

```
cggatgaccg gcaccacctg gcggtccgcg atggacggca cgaccgaccg gaacgcgctg        420
ctcgccctgg cccgcgaact cggccgggtg ctcggccggc tgcacagggt gccgctgacc        480
gggaacaccg tgctcacccc ccattccgag gtcttcccgg aactgctgcg ggaacgccgc        540
gcggcgaccg tcgaggacca ccgcgggtgg ggctacctct cgccccggct gctggaccgc        600
ctggaggact ggctgccgga cgtggacacg ctgctggccg gccgcgaacc ccggttcgtc        660
cacggcgacc tgcacgggac caacatcttc gtggacctgg ccgcgaccga ggtcaccggg        720
atcgtcgact tcaccgacgt ctatgcggga gactcccgct acagcctggt gcaactgcat        780
ctcaacgcct ccggggcga ccgcgagatc ctggccgcgc tgctcgacgg ggcgcagtgg        840
aagcggaccg aggacttcgc ccgcgaactg ctcgccttca ccttcctgca cgacttcgag        900
gtgttcgagg agaccccgct ggatctctcc ggcttcaccg atccggagga actggcgcag        960
ttcctctggg ggccgccgga caccgccccc ggcgcctga                               999

<210> SEQ ID NO 41
<211> LENGTH: 836
<212> TYPE: DNA
<213> ORGANISM: Streptomyces hygroscopicus

<400> SEQUENCE: 41
atgagcccag aacgacgccc ggccgacatc cgccgtgcca ccgaggcgga catgccggcg         60
gtctgcacca tcgtcaacca ctacatcgag acaagcacgg tcaacttccg taccgagccg        120
caggaaccgc aggagtggac ggacgacctc gtccgtctgc gggagcgcta tccctggctc        180
gtcgccgagg tggacggcga ggtcgccggc atcgcctacg cgggcccctg gaaggcacgc        240
aacgcctacg actggacggc cgagtcgacc gtgtacgtct cccccgcca ccagcggacg        300 ggactgggct ccacgctcta cacccacctg ctgaagtccc tggaggcaca gggcttcaag        360
agcgtggtcg ctgtcatcgg gctgcccaac gacccgagcg tgcgcatgca cgaggcgctc        420
ggatatgccc ccgcggcat gctgcgggcg ccggcttca gcacgggaa ctggcatgac         480 gtgggtttct ggcagctgga cttcagcctg ccggtaccgc ccgtccggt cctgcccgtc        540 accgagatct gatgacccgg gtaccgagct cgaatttccc cgatcgttca acatttggc        600 aataaagttt cttaagattg aatcctgttg ccggtcttgc gatgattatc atataatttc        660
tgttgaatta cgttaagcat gtaataatta acatgtaatg catgacgtta tttatgagat        720
gggtttttat gattagagtc ccgcaattat acatttaata cgcgatagaa aacaaaatat        780
agcgcgcaaa ctaggataaa ttatcgcgcg cggtgtcatc tatgttacta gatcgg           836

<210> SEQ ID NO 42
<211> LENGTH: 1000
<212> TYPE: DNA
<213> ORGANISM: Nannochloropsis oceanica

<400> SEQUENCE: 42
gtgtgtcctg cgtgttgatc agtagatgcg caagataccg tcagttagcc agtcgcgtgt         60
gatacactca tcacgaattg aaaaaaaagg gggagggagg aaacgaaggg ccaattgctt        120
acctggccgt gtgcttcatg tgtaaaacaa aatacagtat ggcttcttgt caacctgtcc        180
cccggcactt ccagcttgcc tgccaaggta ctaggcatat ttggtttcgt agaagtagag        240
tcttcatata tgaatgctgt cccggaccttc tcaagggct gcagctcgtt ggcgattggt        300
gaatctatgc ccaattcatc cgactctttg tcgggttccg agaggaggac ttgtcatgaa        360 agagatag g gctttggtct tgcacacgcc cgcgttccag cttt ccccccc gcaaccctcgc      420
```

| | |
|---|---|
| gcgtcgacca tgcgttgttg cctttgcatg acgcgcggtc ataatctact gtagatgctg | 480 |
| gcgacctttt ccttttttt catctttgaa cacaacagat atacgctgag gcgtcgggaa | 540 |
| agcgcaaaat accgcgcgct gttgacgtcc gcttattttg ttggcccgcc ccgcgctctt | 600 |
| ccttgtgcct tcgcaggtcc atctgtggat tcgcgtccca agaccaagca ccattgtctt | 660 |
| tcatagctgc catgcatggt tgtggcacgc caggggaggc gaatcccata gccaccaaac | 720 |
| ctcgtggctg tgccgagtgc cgtgcacccc aaggagtatc cttgcactca tgcggcctgc | 780 |
| gttgccttcg tgctcatgcc cccatgagac gcgcaaaggc agcaaagacc tgagctagcg | 840 |
| gaatctttga tttcacaagg catgtaaaat gtatcaaggt cctgggcgca gggcttttgc | 900 |
| ctcacgcagc aacacattcc aatcctatct cacatgtcca atccttcatt catcacctcc | 960 |
| ggccctccgc acaccacagc aactcgacca cccctaaaa | 1000 |

<210> SEQ ID NO 43
<211> LENGTH: 938
<212> TYPE: DNA
<213> ORGANISM: Nannochloropsis oceanica

<400> SEQUENCE: 43

| | |
|---|---|
| gaaagatcca agagagacga gtagagattt ttttttggg attgatgttt gtcgttcttt | 60 |
| gagttgtcgt cgagttacgc cttttgtaag aatgttccgc aggagaggag gaggatgggc | 120 |
| atgagtgagg gtgagagggc ttgcccgctt ttttttttaa aaacgctgaa gacgtggttg | 180 |
| tcaaacaaac cccccataga aacgattttg ttacggtgcg gtccagacgt cacttgaatg | 240 |
| gctccgcgga aaggccaggg agggaagggg ggagggagga aacatgaaac atgttgaacg | 300 |
| gctcaacagg gtttggggga caagagaggt agcgccctga tggactgctc cctcccctcc | 360 |
| tttccctcaa tgtctcattc atccatgctt ccccttctc tctctccct ccgttccatc | 420 |
| ccccgcgggc gtggtagtgg cgtgatggga tccactaaaa tgtacgtgta agaaaagccg | 480 |
| gtgagcttac gcttttgtga agtgggagt acgagtgttg tgtgtgtgtg tagtggtttc | 540 |
| agacccccaga cagaggcgaa gcagaaaaag cagacgatga agacgacgaa gaaatgagca | 600 |
| gtctattttt atcgtggaaa cagaagaggt gatatcgtct cgttctttgt tatcacctac | 660 |
| cccgcgtgca tgtacatgca gccttttat tttgtaatct ttcccgaaaa atcaaccgcc | 720 |
| acctcccccc cgccttctct cacccatcat cttctcctgt ttatcttcta ctttacacta | 780 |
| gatcgcatgg cacatctccc tcgcaatcca tcggtgcaac catcatcgat cccactcctc | 840 |
| cctccctccc tccctcccte ctcccctctc ttctaagaaa tccgctagct gcgaacccag | 900 |
| ctcacctacc tcatttatca gagcctcgat tcggtcct | 938 |

<210> SEQ ID NO 44
<211> LENGTH: 1000
<212> TYPE: DNA
<213> ORGANISM: Nannochloropsis oceanica

<400> SEQUENCE: 44

| | |
|---|---|
| cgcaaaaaac agacaaactt cgtcactcac cgtcgggagg gcttttgctg ctccagtagt | 60 |
| ggttggtcga cttcggccca cttttcctcc agaacaagcc cccaatactc tcgaagagct | 120 |
| gccgttgcgg gggcgagcga ccttgacgtc gcggtattta cgaagcctca tctcggctct | 180 |
| tttacaattg tttgtgttgt tactcttgtt gtgactccac accactttgg tcggatggt | 240 |
| gtcgactaga tttcgtcgtc gttgtgtgct ggcattcttt cgagcgacaa tgccttcatc | 300 |

```
aattcagagg acaggcattg tttcttcttg tgtgtgctgg ttgggcggtg aggcgctgat    360
ttgtgcctac tttgtggctt tgatacgccg cctttccgcc cttttcaccc tgtacaacca    420
cgcacagctc gagacggcta attatgcctg tatatctgcg ccccctgtgt aagggggtgtg   480 tgtttgccgc tcggatgcgt gtgtcctgac gatgtcgacg ctgcatcacc tcgcttcccg    540
ccagcaggag gtggtcgcat gggttggggc cgcacatcca cacgacaagc aacaagcccc    600
gcttcctcgg tgctcaaggc attgatgaca taccctgtat cgcgtgcctg ggtggcacga    660
ttgccatacc gtgtgcattg tgctgcctct tgtgcaggcg ggcgagggtg tggcaatacg    720
ctccttacta agatagtggc ggggctttgt tgcccgagcg gtggcacttg tcggcaacag    780
actctctggg cacgcttcac ttgccaccag caacacaagg ccaggcggcg gacattacgg    840
tgccctaaga acagaggcag cacgtgtgca cgccctaaga aatgaccgcg gtacatcagg    900
attaattccc gtcacgccgc atcctcaact cccctccctt tccacccaca accccgcta    960 ctctatcaca ggaaaccttt cctcgccgaa cacttcaaaa                         1000

<210> SEQ ID NO 45
<211> LENGTH: 1000
<212> TYPE: DNA
<213> ORGANISM: Nannochloropsis oceanica

<400> SEQUENCE: 45
tttggaagag agtttgctgt ttgtaagaga aagggaaag gggaaaacta atcgtcagga     60
ggtatgatat ggatatgaag agtgcgccgc ggaagaaaa ctagagttgt ttcattcctt    120
tgattccatt taagcaagca acagcaacgc caacagcaac cgcatttaga aaaagataga   180
gggaacagtc tgagtagaga gaatacaagt agagcggaag tgatagagtg aggcaagagg   240
gaagtatctg cggggcagga gatgggggac agattgcgca tcataaaagg agtagaaatg   300
ccattggtta gcgtcgcttt cctctgccct ctctgtcctc aaattcctat gcacccacac   360
ttctcggtcc cgtgttccac gcatgccttc ccccgtgtct ccctctccgc cttaccctct   420
cccccatctt tatccattat tagaaatagt tgtgtcgagt cgatcggatc gcagaagtat   480
gtgtacagag tgaggggga gggagaagaa gacgacggaa gttaagagga cggacatgat    540
gacggagtag aaaaagaaac gcaagcacac cagcagcggt agaaactttt aaaaaaagac    600
caaggactgg aaatctgtaa tcttggcgaa gacaaaaaaa tccacctact taatctctga    660
atcaagaaaa taacacactc actcccctcg gttttaattc tacacgtctt tctttttcttt   720 gctttgttgt atgctcgatg aagccttcca catttctgtc tcgatacttt ctggtatcct   780 tcatttttggg ctagtttact ctcacggctg tcttaatggt gccaatgtac aaagcgagaa    840
atacaaaccc ttgtgcgcct ccttttcttt cgcgacaaca tctcaagatg atgataccgc    900
agacgccgct gctacgggtg ctgctacttc tgttgctgct ccacctgctc ctcctacctt    960
tcctcctttg cagccaagtc aagcaagcgc cgatgtaaca                         1000

<210> SEQ ID NO 46
<211> LENGTH: 35
<212> TYPE: DNA
<213> ORGANISM: Artificial sequence
<220> FEATURE:
<223> OTHER INFORMATION: Primer No. 46

<400> SEQUENCE: 46
cttttttgtg aagcaatggt cgagattcga agcat                               35
```

```
<210> SEQ ID NO 47
<211> LENGTH: 35
<212> TYPE: DNA
<213> ORGANISM: Artificial sequence
<220> FEATURE:
<223> OTHER INFORMATION: Primer No. 47

<400> SEQUENCE: 47
tttcccccat cccgatcaga agaactcgtc caaca                              35

<210> SEQ ID NO 48
<211> LENGTH: 37
<212> TYPE: DNA
<213> ORGANISM: Artificial sequence
<220> FEATURE:
<223> OTHER INFORMATION: Primer No. 48

<400> SEQUENCE: 48
cttttttgtg aagcaatgac acaagaatcc ctgttac                            37

<210> SEQ ID NO 49
<211> LENGTH: 36
<212> TYPE: DNA
<213> ORGANISM: Artificial sequence
<220> FEATURE:
<223> OTHER INFORMATION: Primer No. 49

<400> SEQUENCE: 49
tttcccccat cccgatcagg cgccgggggc ggtgtc                             36

<210> SEQ ID NO 50
<211> LENGTH: 35
<212> TYPE: DNA
<213> ORGANISM: Artificial sequence
<220> FEATURE:
<223> OTHER INFORMATION: Primer No. 50

<400> SEQUENCE: 50
cttttttgtg aagcaatgag cccagaacga cgccc                              35

<210> SEQ ID NO 51
<211> LENGTH: 37
<212> TYPE: DNA
<213> ORGANISM: Artificial sequence
<220> FEATURE:
<223> OTHER INFORMATION: Primer No. 51

<400> SEQUENCE: 51
tttcccccat cccgatcaga tctcggtgac gggcagg                            37

<210> SEQ ID NO 52
<211> LENGTH: 40
<212> TYPE: DNA
<213> ORGANISM: Artificial sequence
<220> FEATURE:
<223> OTHER INFORMATION: Primer No. 52

<400> SEQUENCE: 52
cgagctcggt acccggtgtg tcctgcgtgt tgatcagtag                         40

<210> SEQ ID NO 53
<211> LENGTH: 29
<212> TYPE: DNA
<213> ORGANISM: Artificial sequence
<220> FEATURE:
<223> OTHER INFORMATION: Primer No. 53
```

<400> SEQUENCE: 53
ttttaggggg tggtcgagtt gctgtggtg                                29

<210> SEQ ID NO 54
<211> LENGTH: 24
<212> TYPE: DNA
<213> ORGANISM: Artificial sequence
<220> FEATURE:
<223> OTHER INFORMATION: Primer No. 54

<400> SEQUENCE: 54
gaaagatcca agagagacga gtag                                     24

<210> SEQ ID NO 55
<211> LENGTH: 30
<212> TYPE: DNA
<213> ORGANISM: Artificial sequence
<220> FEATURE:
<223> OTHER INFORMATION: Primer No. 55

<400> SEQUENCE: 55
aggaccgaat cgaggctctg ataaatgagg                               30

<210> SEQ ID NO 56
<211> LENGTH: 39
<212> TYPE: DNA
<213> ORGANISM: Artificial sequence
<220> FEATURE:
<223> OTHER INFORMATION: Primer No. 56

<400> SEQUENCE: 56
cctcgattcg gtcctttctt ccgcttgttg ctgccgatg                     39

<210> SEQ ID NO 57
<211> LENGTH: 35
<212> TYPE: DNA
<213> ORGANISM: Artificial sequence
<220> FEATURE:
<223> OTHER INFORMATION: Primer No. 57

<400> SEQUENCE: 57
cgagctcggt acccgcgcaa aaaacagaca aactt                         35

<210> SEQ ID NO 58
<211> LENGTH: 34
<212> TYPE: DNA
<213> ORGANISM: Artificial sequence
<220> FEATURE:
<223> OTHER INFORMATION: Primer No. 58

<400> SEQUENCE: 58
ttttgaagtg ttcggcgagg aaaggtttcc tgtg                          34

<210> SEQ ID NO 59
<211> LENGTH: 27
<212> TYPE: DNA
<213> ORGANISM: Artificial sequence
<220> FEATURE:
<223> OTHER INFORMATION: Primer No. 59

<400> SEQUENCE: 59
tttggaagag agtttgctgt tgtaag                                   27

<210> SEQ ID NO 60
<211> LENGTH: 27

```
<212> TYPE: DNA
<213> ORGANISM: Artificial sequence
<220> FEATURE:
<223> OTHER INFORMATION: Primer No. 60

<400> SEQUENCE: 60
tgttacatcg gcgcttgctt gacttgg                                              27

<210> SEQ ID NO 61
<211> LENGTH: 37
<212> TYPE: DNA
<213> ORGANISM: Artificial sequence
<220> FEATURE:
<223> OTHER INFORMATION: Primer No. 61

<400> SEQUENCE: 61
agcgccgatg taacagtgtg tcctgcgtgt tgatcag                                   37

<210> SEQ ID NO 62
<211> LENGTH: 30
<212> TYPE: DNA
<213> ORGANISM: Artificial sequence
<220> FEATURE:
<223> OTHER INFORMATION: Primer No. 62

<400> SEQUENCE: 62
cgcaaaaaac agacaaactt cgtcactcac                                           30

<210> SEQ ID NO 63
<211> LENGTH: 37
<212> TYPE: DNA
<213> ORGANISM: Artificial sequence
<220> FEATURE:
<223> OTHER INFORMATION: Primer No. 63

<400> SEQUENCE: 63
cagcccgcat caacaatggc tcgcctcttc gtcaccg                                   37

<210> SEQ ID NO 64
<211> LENGTH: 37
<212> TYPE: DNA
<213> ORGANISM: Artificial sequence
<220> FEATURE:
<223> OTHER INFORMATION: Primer No. 64

<400> SEQUENCE: 64
ctcttccaca gaagcttagt acttataccc cttcacg                                   37

<210> SEQ ID NO 65
<211> LENGTH: 39
<212> TYPE: DNA
<213> ORGANISM: Artificial sequence
<220> FEATURE:
<223> OTHER INFORMATION: Primer No. 65

<400> SEQUENCE: 65
gaccaccccc taaaaatggt tgctaaagct gcttttgcc                                 39

<210> SEQ ID NO 66
<211> LENGTH: 40
<212> TYPE: DNA
<213> ORGANISM: Artificial sequence
<220> FEATURE:
<223> OTHER INFORMATION: Primer No. 66

<400> SEQUENCE: 66
```
tctcttggat ctttcttaca gataggcctt ggcctccttg                    40

<210> SEQ ID NO 67
<211> LENGTH: 40
<212> TYPE: DNA
<213> ORGANISM: Artificial sequence
<220> FEATURE:
<223> OTHER INFORMATION: Primer No. 67

<400> SEQUENCE: 67
ccgaacactt caaaaatgag ccgccaaaag actctctttt                    40

<210> SEQ ID NO 68
<211> LENGTH: 40
<212> TYPE: DNA
<213> ORGANISM: Artificial sequence
<220> FEATURE:
<223> OTHER INFORMATION: Primer No. 68

<400> SEQUENCE: 68
aaactctctt ccaaactact tcttattgat gacgtcgatg                    40

<210> SEQ ID NO 69
<211> LENGTH: 38
<212> TYPE: DNA
<213> ORGANISM: Artificial sequence
<220> FEATURE:
<223> OTHER INFORMATION: Primer No. 69

<400> SEQUENCE: 69
gaccaccccc taaaaatgac gccgcaagcc gacatcac                      38

<210> SEQ ID NO 70
<211> LENGTH: 35
<212> TYPE: DNA
<213> ORGANISM: Artificial sequence
<220> FEATURE:
<223> OTHER INFORMATION: Primer No. 70

<400> SEQUENCE: 70
tctcttggat ctttcttact caatggacaa cgggc                         35

<210> SEQ ID NO 71
<211> LENGTH: 38
<212> TYPE: DNA
<213> ORGANISM: Artificial sequence
<220> FEATURE:
<223> OTHER INFORMATION: Primer No. 71

<400> SEQUENCE: 71
cagcccgcat caacaatgcc cgcctacacg acgacatc                      38

<210> SEQ ID NO 72
<211> LENGTH: 37
<212> TYPE: DNA
<213> ORGANISM: Artificial sequence
<220> FEATURE:
<223> OTHER INFORMATION: Primer No. 72

<400> SEQUENCE: 72
ctcttccaca gaagcctact tgtagagatt ggcgatg                       37

<210> SEQ ID NO 73
<211> LENGTH: 37
<212> TYPE: DNA
<213> ORGANISM: Artificial sequence
<220> FEATURE:
<223> OTHER INFORMATION: Primer No. 73

<400> SEQUENCE: 73
cagcccgcat caacaatgag aataccttcc cttatcc    37

<210> SEQ ID NO 74
<211> LENGTH: 35
<212> TYPE: DNA
<213> ORGANISM: Artificial sequence
<220> FEATURE:
<223> OTHER INFORMATION: Primer No. 74

<400> SEQUENCE: 74
ctcttccaca gaagcctacg tcgtgcccat gttca    35

<210> SEQ ID NO 75
<211> LENGTH: 34
<212> TYPE: DNA
<213> ORGANISM: Artificial sequence
<220> FEATURE:
<223> OTHER INFORMATION: Primer No. 75

<400> SEQUENCE: 75
gtgtgtcctg cgtgttgatc agtagatgcg caag    34

<210> SEQ ID NO 76
<211> LENGTH: 437
<212> TYPE: PRT
<213> ORGANISM: Nannochloropsis oceanica

<400> SEQUENCE: 76

Met Ser Met His Lys Leu Thr Arg Pro Ser Val Leu Ser Ile Glu Tyr
1               5                   10                  15

Pro Ser Arg Asp Tyr Thr Gly Tyr Leu Asn Leu Ala Met Ile Ile Leu
            20                  25                  30

Gly Val His Phe Ser His Ala Val Val Asp Cys Val Ser Leu Val Trp
        35                  40                  45

Arg Tyr Gly Val Gln Leu Pro Lys His Ser Leu Val Glu Val Pro Cys
    50                  55                  60

Leu Met Cys Ala Leu Ser Leu Thr Ile Asn Ile Phe Leu Ala Trp Phe
65                  70                  75                  80

Thr Glu Tyr Leu Ala Ser Arg Arg Phe Phe Pro Ser Ser Met Ala Val
                85                  90                  95

Gly Val Leu His Ser Leu Asn Cys Leu Trp Thr Leu Leu Tyr Pro Cys
            100                 105                 110

His Val Ala Trp Ser Arg Pro Asp Val Pro Leu His Thr Phe Leu Leu
        115                 120                 125

Leu Phe Trp Ser Val Ile Ala Phe Leu Lys Leu Val Ser Trp Ser His
    130                 135                 140

Thr Asn Trp Asp Leu Arg His Ala Phe Ser Arg Arg Ala Arg Lys
145                 150                 155                 160

Ser Gln Ala His Leu Pro Ala Ala Ala Leu His Glu Asp Gly Tyr Asn
                165                 170                 175

Asn Ala Lys Pro Leu Glu Ser Gly Ala Thr Arg Tyr Pro His Ser Val
            180                 185                 190

Ser Leu Ser Asn Ile Ser Phe Phe Phe Cys Pro Thr Leu Cys Tyr
        195                 200                 205

Gln Pro Asp Tyr Pro Arg Ala Pro Thr Ile Arg Leu Arg Thr Leu Ala

```
                     210                 215                 220
Ser Leu Thr Phe Arg Ile Ile Val Met Thr Ala Phe Ala Gly Phe Ile
225                 230                 235                 240

Ile Asp Gln Gln Ile His Pro Ile Ile Gln Asn Thr Met Ser His Val
                245                 250                 255

Asp Ser Leu Asp Leu Leu Lys Ala Leu Gly Glu Leu Leu Arg Leu Ala
            260                 265                 270

Ile Pro Ser Thr Phe Val Trp Leu Ile Phe Phe Tyr Val Tyr Phe His
        275                 280                 285

Cys Thr Leu Asn Leu Phe Ala Glu Leu Thr Arg Phe Gly Asp Arg Leu
    290                 295                 300

Phe Phe Lys Asp Trp Trp Asn Ser Thr Ser Phe Ser Arg Tyr Trp Arg
305                 310                 315                 320

Thr Trp Asn Leu Pro Val His Gln Phe Val Val Arg His Val Tyr Phe
                325                 330                 335

Pro Leu Leu Arg Ala Gly Ala Ser Lys Met Thr Ala Asn Val Ala Val
            340                 345                 350

Phe Ala Val Ser Ala Phe Phe His Glu Leu Leu Ile Ser Ile Pro Cys
        355                 360                 365

His Val Val Arg Leu Trp Ala Phe Leu Ala Met Met Gly Gln Ile Pro
    370                 375                 380

Leu Ile Tyr Leu Thr Asp Gln Leu Glu Lys Thr Leu Phe Lys Glu Thr
385                 390                 395                 400

Gln Ala Gly Asn Tyr Thr Phe Trp Leu Ile Phe Cys Ile Phe Gly Gln
                405                 410                 415

Pro Met Ala Val Leu Leu Tyr Tyr Ala Asp Phe Ser Ala Arg Thr Thr
            420                 425                 430

Ser Glu Ser Ala Leu
            435

<210> SEQ ID NO 77
<211> LENGTH: 1314
<212> TYPE: DNA
<213> ORGANISM: Nannochloropsis oceanica

<400> SEQUENCE: 77
atgtctatgc acaaactgac tcgaccgagc gtgctgtcca ttgagtatcc ctcgcgggat      60
tatacgggtt atttgaacct ggcaatgatc atcctcggtg tccactttc ccacgccgta     120 gtcgactgcg tctcgctggt gtggcggtac ggagtgcagc tcccgaagca ttctctggtg     180
gaggtgccct gcctcatgtg cgcgctctcc ctcaccatca acatcttctt ggcttggttc     240
accgaatacc tcgcctcccg tgcttcttc ccctcctcga tggcggtagg tgtgctgcat     300
tccctgaact gccatggac gctgctctac ccctgccacg tggcatggag ccggccggac     360
gtgcctctgc acacgttctt gttgctattt tggagtgtga tcgccttctt aaagctcgtc     420
tcctggtccc acactaattg ggatcttcga catgctttct tctcccggcg cgcccgcaag     480
tctcaggctc acctgccagc agcggccctt cacgaagacg gctacaacaa tgccaagccc     540
ctcgagagcg cgccacgcg gtacccgcac tcggtctcac taagcaacat aagcttcttc     600
ttcttctgtc ccactctctg ctaccagccc gactaccac gcgcgccaac gattcgattg     660
cggacactcg cctcgctcac ctttcgtatc atcgtcatga cggcctttgc gggcttcatc     720
atcgaccagc agatccaccc catcatccag aacaccatga gccacgtcga tagcctcgat     780
ctcctcaagg ccctgggtga gctgctccgc cttgccatcc cctccacctt cgtctggctc     840
```

```
attttcttct acgtctactt ccactgcacc ctcaatcttt tcgcggaatt aacgcgtttc      900
ggggatcgat tgtttttcaa ggattggtgg aacagcacca gcttctcccg ctattggcga      960
acttggaatc ttcccgtcca tcagtttgtc gtccgtcatg tgtacttccc cttgctacgc     1020 gcggggcgt  ctaaaatgac ggccaacgtc gccgttttcg ctgtctcggc cttcttccac     1080
gagctgctga tctcgatacc ctgccacgtc gtgcggctgt gggcgttttt ggccatgatg     1140
ggccagatcc ctctcatcta ccttacggac cagctggaga aaaccttgtt caaggaaacg     1200
caggcaggga attacacctt ctggcttatc ttctgtatct tcggacagcc aatggcagtg     1260
ctcttgtact atgctgactt ctctgcccgc actaccagcg agagcgctct ttag           1314
```